(12) United States Patent
Atashbar et al.

(10) Patent No.: US 11,525,063 B2
(45) Date of Patent: Dec. 13, 2022

(54) FLUORESCENT OXYGEN SENSING INK

(71) Applicants: The Board of Trustees of Western Michigan University, Kalamazoo, MI (US); Purdue Research Foundation, West Lafayette, IN (US)

(72) Inventors: Massood Zandi Atashbar, Portage, MI (US); Binu Baby Narakathu, Portage, MI (US); Dinesh Maddipatla, Kalamazoo, MI (US); Babak Ziaie, West Lafayette, IN (US); Manuel Ochoa, Lafayette, IN (US); Rahim Rahimi, West Lafayette, IN (US)

(73) Assignees: The Board of Trustees of Western Michigan University, Kalamazoo, MI (US); Purdue Research Foundation, West Lafayette, IN (US)

( * ) Notice: Subject to any disclaimer, the term of this patent is extended or adjusted under 35 U.S.C. 154(b) by 892 days.

(21) Appl. No.: 16/288,819

(22) Filed: Feb. 28, 2019

(65) Prior Publication Data
US 2019/0264049 A1 Aug. 29, 2019

Related U.S. Application Data

(63) Continuation of application No. PCT/US2018/020284, filed on Feb. 28, 2018.
(Continued)

(51) Int. Cl.
*C09D 11/00* (2014.01)
*C09D 11/14* (2006.01)
(Continued)

(52) U.S. Cl.
CPC ........ *C09D 11/14* (2013.01); *A61F 13/00012* (2013.01); *A61F 13/00034* (2013.01);
(Continued)

(58) Field of Classification Search
USPC .......... 106/31.01, 31.13, 31.27, 31.28, 31.32
See application file for complete search history.

(56) References Cited

U.S. PATENT DOCUMENTS 5,792,090 A 8/1998 Ladin
5,837,042 A * 11/1998 Lent ........................ G06K 7/12
106/31.15
(Continued)

FOREIGN PATENT DOCUMENTS

WO 9710307 3/1997
WO 0163264 A1 8/2001
(Continued)

OTHER PUBLICATIONS

C. K. Sen, G. M. Gordillo, S. Roy, R. Kirsner, L. Lambert, T.K. Hunt, F.Gottrup, G. C. Gurtner, and M. T. Longaker, "Human skin wounds: a major and snowballing threat to public health and the economy." Wound repair and regeneration: official publication of the Wound Healing Society [and] the European Tissue Repair Society, vol. 17, No. 6, pp. 763-71, 2009.
(Continued)

*Primary Examiner* — James E McDonough
(74) *Attorney, Agent, or Firm* — Price Heneveld LLP

(57) ABSTRACT

A fluorescent oxygen sensing ink includes at least one organic solvent, at least one polymer binder disposed in the organic solvent, and an oxygen-sensitive fluorescent dye disposed in the organic solvent. The oxygen-sensitive fluorescent dye and the at least one polymer can interact to form a moisture-resistant film. The fluorescent oxygen sensing ink can be incorporated into an oxygen sensing wound dressing.

22 Claims, 26 Drawing Sheets

Related U.S. Application Data

(60) Provisional application No. 62/636,560, filed on Feb. 28, 2018.

(51) Int. Cl.
  G01N 33/00 (2006.01)
  A61F 13/00 (2006.01)
  C09D 11/033 (2014.01)
  G01N 31/22 (2006.01)
  C09D 1/00 (2006.01)
  C09D 4/00 (2006.01)
  C09D 5/00 (2006.01)
  C09K 3/00 (2006.01)

(52) U.S. Cl.
  CPC ...... A61F 13/00051 (2013.01); C09D 11/033 (2013.01); G01N 31/225 (2013.01); G01N 33/0036 (2013.01)

(56) References Cited

U.S. PATENT DOCUMENTS

| | | | |
|---|---|---|---|
| 6,190,612 | B1 | 2/2001 | Berger et al. |
| 6,767,342 | B1 | 7/2004 | Cantwell |
| 7,833,480 | B2 | 11/2010 | Blazewicz et al. |
| 8,313,710 | B2 | 11/2012 | Kane |
| 9,204,999 | B2 | 12/2015 | Barta et al. |
| 9,459,241 | B2 | 10/2016 | Khan et al. |
| 9,474,654 | B2 | 10/2016 | Heagle et al. |
| 9,522,177 | B2 | 12/2016 | Barrett et al. |
| 9,538,944 | B2 | 1/2017 | Rao et al. |
| 9,554,945 | B2 | 1/2017 | Coffey |
| 9,572,968 | B2 | 2/2017 | Dorian et al. |
| 9,655,840 | B2 | 5/2017 | Givskov et al. |
| 2010/0150991 | A1 | 6/2010 | Bernstein |
| 2012/0046644 | A1 | 2/2012 | Ziaie et al. |
| 2015/0202399 | A1 | 7/2015 | Ziaie et al. |
| 2017/0016865 | A1 | 1/2017 | Khan et al. |
| 2017/0143881 | A1 | 5/2017 | Topaz |
| 2017/0176332 | A1 | 6/2017 | Scolan et al. |
| 2018/0249952 | A1 | 9/2018 | Ziaie et al. |

FOREIGN PATENT DOCUMENTS

| | | | |
|---|---|---|---|
| WO | 2009037477 A1 | 3/2009 | |
| WO | WO-2009037477 A1 * | 3/2009 | ........... C07D 471/04 |

OTHER PUBLICATIONS

R.O.Y.W. Tamuzzer and G.S. Schultz, "Biochemical analysis of acute and chronic wound environments," Wound Repair and Regeneration, vol. 4, pp. 321-325, 1996.

M. E. Lait and L. N. Smith, "Wound management: a literature review," Journal of Clinical Nursing, vol. 7, No. 1, pp. 11-17, 11998.

G. Chaby, P.Senet, M. Vaneau, P.Martel, J.-C. Guillaume, S. Meaume, L. Téot, C. Debure, A. Dompmartin, H. Bachelet, H. Carsin, V. Matz, J. L. Richard, J. M. Rochet, N. Sales-Aussias, A. Zagnoli, C. Denis, B. Guillot, and O. Chosidow, "Dressings for acute and chronic wounds: a systematic review." Archives of dermatology, vol. 143, No. 10, pp. 1297-304, 102007.

N. Mehmood, A.Hariz, R. Fitridge, and N.H. Voelcker, "Applications of modern sensors and wireless technology in effective wound management." Journal of biomedical materials research. Part B, Applied biomaterials, vol. 102, No. 4, pp. 885-95, 52014.

M. Ochoa, R. Rahimi, and B. Ziaie, "Flexible Sensors for Chronic Wound Management," IEEE Reviews in Biomedical Engineering, vol. 7, pp. 73-86, 12014.

S. Schreml, R. M. Szeimies, L. Prantl, S. Karrer, M. Landthaler, and P. Babilas, "Oxygen in acute and chronic wound healing " The British journal of dermatology, vol. 163, No. 2, pp. 257-268, 82010.

P. Kranke, M. H. Bennett, M. Martyn-St James, A. Schnabel, and S.

E. Debus, "Hyperbaric oxygen therapy for chronic wounds." The Cochrane database of systematic reviews, vol. 4, No. 4, p. CD004123,12012.

M. A. Howard, R. Asmis, K. K. Evans, and T. A. Mustoe, "Oxygen and wound care: A review of current therapeutic modalities and future direction," Wound Repair and Regeneration, vol. 21, No. 4, pp. 503-511, 72013.

G.M. Gordillo, R.Schlanger, W.a. Wallace, V. Bergdall, R. Bartlett, and C.K. Sen, "Protocols for topical and systemic oxygen treatments in wound healing." Methods in enzymology, vol. 381, No. 1968, pp. 575-585, 12004.

A. Russo, B. Y. Ahn, J. J. Adams, E. B. Duoss, J. T. Bernhard, and J. A. Lewis, "Pen-on-paper flexible electronics." Advanced materials (Deerfield Beach, Fla.), vol. 23, No. 30, pp. 3426-3430, 82011.

C.-M. Cheng, A.D. Mazzeo, J. Gong, A.W. Martinez, S.T. Phillips, N. Jain, and G.M. Whitesides, "Millimeter-scale contact printing of aqueous solutions using a stamp made out of paper and tape."Lab on a chip, No. 1, pp. 3201-3205, 102010.

A. W. Martinez, S. T. Phillips, M. J. Butte, and G. M. Whitesides, "Patterned paperas a platform for inexpensive, low-volume portable bioassays."Angewandte Chemie (International ed. in English), vol. 46, No. 8, pp. 1318-1320,12007.

Z. Ding, P.Wei, G. Chitnis, and B. Ziaie, "Ferrofluid-Impregnated Paper Actuators," Journal of Microelectromechanical Systems, vol. 20, No. 1, pp. 59-64, Feb. 2011.

M. Ochoa, G. Chitnis, and B. Ziaie, "Laser-micromachined cellulose acetate adhesive tape as a low-cost smart material," Journal of Polymer Science Part B: Polymer Physics, vol. 51, No. 17, pp. 1263-1267, 92013.

B. M. Smith, L. D. Desvigne, J. B. Slade, J. W. Dooley, and D. C. Warren, "Transcutaneous oxygen measurements predict healing of leg wounds with hyperbaric therapy." Wound repair and regeneration: official publication of the Wound Healing Society [and] the European Tissue Repair Society, vol. 4, No. 2, pp. 224-229, 1996.

D. Queen, J. H. Evans, J. D. Gaylor, J. M. Courtney, and W.H. Reid,"An invitro assessment of wound dressing conformability." Biomaterials, vol. 8, No. 5,pp. 372-376, 91987.

J. Seo, "Making monosaccharide and disaccharide sugar glasses by using microwave oven," Journal of Non-Crystalline Solids, vol. 333, No. 1, pp. 111-114, Jan. 2004.

W. Li, D. C. Rodger, A. Pinto, E. Meng, J. D. Weiland, M. S. Humayun, and Y.-C. Tai, "Parylene-based integrated wireless single-channel neurostimulator," Sensors and Actuators A: Physical, vol. 166, No. 2, pp. 193-200,Apr. 2011.

H.-S. Noh, Y. Huang, and P. J. Hesketh, "Parylene micromolding, a rapid and low-cost fabrication method for parylene microchannel," Sensors and Actuators B: Chemical, vol. 102, No. 1, pp. 78-85, Sep. 2004.

D. C. Rodger, A. J. Fong, W. Li, H. Ameri, A. K. Ahuja, C. Gutierrez, I. Lavrov, H. Zhong, P.R. Menon, E. Meng, J. W. Burdick, R. R. Roy, V.R. Edgerton, J. D. Weiland, M. S. Humayun, and Y.-C. Tai, "Flexible parylene-based multielectrode array technology for high-density neural stimulation and recording," Sensors and Actuators B: Chemical, vol. 132, No. 2, pp. 449-460, 62008.

D. Armani, C. Liu, and N. Aluru, "Re-configurable fluid circuits by PDM Selastomer micromachining," in Twelfth IEEE International Conference on Micro Electro Mechanical Systems. IEEE, 1999, pp. 222-227.

K. P. Cooper and R. F.Wachter, "High-rate, roll-to-roll nanomanufacturing of flexible systems," vol. 8466, No. 202, p. 846602,Oct. 2012.

S.-H. Do, B. Batchelor, H.-K. Lee, and S.-H. Kong, "Hydrogen peroxide decomposition on manganese oxide (pyrolusite): kinetics, intermediates, and mechanism."Chemosphere, vol. 75, No. 1, pp. 8-12, 32009.

R.H. Burdon,"Superoxide and hydrogen peroxide in relation to mammalian cell proliferation," Free Radical Biology and Medicine, vol. 18, No. 4, pp. 775-794, 41995.

B. Mosadegh, C.-H. Kuo, Y.-C. Tung, Y.-S. Torisawa, T. Bersano-Begey, H. Tavana, and S. Takayama, "Integrated elastomeric components for autonomous regulation of sequential and oscillatory flow switching in microfluidic devices," Nature Physics, vol. 6, No. 6, pp. 433-437, 2010.

(56) References Cited

OTHER PUBLICATIONS

R. Rahimi, M. Ochoa, and B. Ziaie,"A low-cost flexible electrochemical sensor for monitoring silver ion concentration in alginate wound dressings," in Proc. Sensors'13, 2013.
A. Stojadinovic, J. W. Carlson, G. S. Schultz, T. A. Davis, and E. A. Elster, "Topical advances in wound care." Gynecologic oncology, vol. 111, No. 2 Suppl, pp. 70-80, Nov. 2008.
A. A. Tandara and T. A. Mustoe, "Oxygen in wound healing—more than a nutrient." World journal of surgery, vol. 28, No. 3, pp. 294-300, Mar. 2004.
C. K. Sen, "Wound healing essentials: let there be oxygen." Wound repair and regeneration, vol. 17, No. 1, pp. 1-18, 2010.
D. M. Castilla, Z.-J. Liu, and O. C. Velazquez, "Oxygen: Implications for Wound Healing," Advances in Wound Care, vol. 1, No. 6, pp. 225-230, Dec. 2012.
N. S. Greaves, S. a. Iqbal, M. Baguneid, and A. Bayat, "The role of skin substitutes in the management of chronic cutaneous wounds." Wound repair and regeneration : official publication of the Wound Healing Society [and] the European Tissue Repair Society, vol. 21, No. 2, pp. 194-210, 2013.
H. Klank, J. P. J. P. Kutter, and O. Geschke, "CO(2)-laser micromachining and back-end processing for rapid production of PMMA-based microfluidic systems." Lab ona Chip, vol. 2, No. 4, pp. 242-246, Nov. 2002.
G. Chitnis and B. Ziaie, "Waterproof Active Paper via Laser Surface Micropatterning of Magnetic Nanoparticles." ACS applied materials & interfaces, vol. 4, No. 9, pp. 4435-4439, Sep. 2012.
M. Ochoa, R. Rahimi, and B. Ziaie, "Laser-Enabled Fabrication Technologies for Low-Cost Flexible/Conformal Cutaneous Wound Interfaces," in Stretchable Bioelectronics for Medical Devices and Systems, J. A. Rogers, R. Shaffari, and D.-H. Kim, Eds. Springer International Publishing, 2016, ch. 11, pp. 207-226.
J. A. McGrath, R. A. J. Eady, and F. M. Pope, "Anatomy and Organization of Human Skin," in Rook's Textbook of Dermatology Malden, Massachusetts, USA: Blackwell Publishing, Inc., 2004, pp. 45-128.
C. Mørk, K. Kvernebo, C. L. Asker, and E. G. Salerud, "Reduced skin capillary density during attacks of erythromelalgia implies arteriovenous shunting as pathogenetic mechanism," Journal of Investigative Dermatology, vol. 119, No. 4, pp. 949-953, 2002.
L. A. Schneider, A. Korber, S. Grabbe, and J. Dissemond, "Influence of pH on wound-healing: a new perspective for wound-therapy?" Archives of dermatological research, vol. 298, No. 9, pp. 413-420, Feb. 2007.
R. G. Frykberg and J. Banks, "Challenges in the Treatment of Chronic Wounds," Advances in wound care, vol. 4, No. 9, pp. 560-582, 2015.
G. S. Schultz, R. G. Sibbald, V. Falanga, E. A. Ayello, C. Dowsett, K. Harding, M. Romanelli, M. C. Stacey, L. Teot, and W. Vanscheidt, "Wound bed preparation: a systematic approach to wound management," Wound Repair and Regeneration, vol. 11, pp. 1-28, Mar. 2003.
T. Abdelrahman and H. Newton, "Wound dressings: principles and practice," Surgery (Oxford), vol. 29, No. 10, pp. 491-495, Oct. 2011.
D. Queen, H. Orsted, H. Sanada, and G. Sussman, "A dressing history." International wound journal, vol. 1, No. 1, pp. 59-77,Apr. 2004.
S.-F. Lo, M. Hayter, C.-J. Chang, W.-Y. Hu, and L.-L. Lee, "A systematic review of silver-releasing dressings in the management of infected chronic wounds." Journal of clinical nursing, vol. 17, No. 15, pp. 1973-1985, Aug. 2008.
C. L. Hess, M. A. Howard, and C. E. Attinger, "A review of mechanical adjuncts in wound healing: hydrotherapy, ultrasound, negative pressure therapy, hyperbaric oxygen, and electrostimulation." Annals of plastic surgery, vol. 51, No. 2, pp. 210-218, Aug. 2003.

J. A. Flegg, H. M. Byrne, and D. L. S. McElwain, "Mathematical model of hyperbaric oxygen therapy applied to chronic diabetic wounds." Bulletin of mathematical biology, vol. 72, No. 7, pp. 1867-1891, Oct. 2010.
H. K. Said, J. Hijjawi, N. Roy, J. Mogford, and T. Mustoe, "Transdermal sustained-delivery oxygen improves epithelial healing in a rabbit ear wound model." Archives of surgery (Chicago, Ill. : 1960), vol. 140, No. 10, pp. 998-1004, Oct. 2005.
G. M. Gordillo, S. Roy, S. Khanna, R. Schlanger, S. Khandelwal, G. Phillips, and C. K. Sen, "Topical oxygen therapy induces vascular endothelial growth factor expression and improves closure of clinically presented chronic wounds." Clinical and experimental pharmacology & physiology, vol. 35, No. 8, pp. 957-964,Aug. 2008.
D. Kemp and M. Hermans, "An evaluation of the efficacy of Transdermal Continuous Oxygen Therapy in patients with recalcitrant diabetic foot ulcer" Journal of Diabetic Foot Complications, vol. 3, No. 1, pp. 6-12, 2011.
P. Banks and C. Ho, "A novel topical oxygen treatment for chronic and difficult-to-heal wounds: case studies," The journal of spinal cord medicine, vol. 31, No. 3, pp. 297-301, 2008.
Ogenix, "EPIFLO® Transdermal Continuous Oxygen Therapy [TCOT] for Wound Healing," 2012. [Online]. Available: http://www.ogenix.com/product-overview/.
Inotec AMD Limited, "Home Page," 2016. [Online]. Available: http://www. inotecamd.com/home-page.
OxyBand Technologies, "OxyBand Technologies—Topical Oxygen Technol-ogy," 2016. [Online]. Available: http://oxyband.com/OxyBand/Images/misc/ OxyBand-Wound-Dressing-1024x837px.jpg.
P. Boisseau and B. Loubaton, "Nanomedicine, nanotechnology in medicine," Comptes Rendus Physique, vol. 12, No. 7, pp. 620-636, Sep. 2011.
M. Ochoa, C. Mousoulis, and B. Ziaie, "Polymeric microdevices for transdermal and subcutaneous drug delivery." Advanced drug delivery reviews, vol. 64, No. 14, pp. 1603-1616, Nov. 2012.
N. Mehmood, A. Hariz, R. Fitridge, and N. H. Voelcker, "Applications of modern sensors and wireless technology in effective wound management." Journal of biomedical materials research. Part B, Applied biomaterials, pp. 1-11, Oct. 2013.
T. R. Dargaville, B. L. Farrugia, J. a. Broadbent, S. Pace, Z. Upton, and N. H. Voelcker, "Sensors and imaging for wound healing: a review." Biosensors & bioelectronics, vol. 41, pp. 30-42, Mar. 2013.
M. D. Kerstein, E. Gemmen, L. van Rijswijk, C. H. Lyder, T. Phillips, G. Xakellis, K. Golden, and C. Harrington, "Cost and Cost Effectiveness of Venous and Pressure Ulcer Protocols of Care," Disease Management and Health Outcomes, vol. 9, No. 11, pp. 651-636, 2001.
B. Derby, "Inkjet Printing of Functional and Structural Materials: Fluid Property Requirements, Feature Stability, and Resolution," Annual Review of Materials Research, vol. 40, No. 1, pp. 395-414, Jun. 2010.
S. Hengsbach and A. D. Lantada, "Rapid prototyping of multi-scale biomedical microdevices by combining additive nanufacturing technologies " Biomedical microdevices, vol. 16, No. 4, pp. 617-627,Aug. 2014.
T. E. Wright, W. G. Payne, F. Ko, D. Ladizinsky, N. Bowlby, R. Neeley, B. Mannari, and M. C. Robson, "The Effects of an Oxygen—Generating Dressing on Tissue Infection and Wound Healing," Journal Of Applied Research, vol. 3, No. 4, pp. 363-370, 2003.
D. W. Brett, "A Review of Moisture-Control Dressings in Wound Care," Journal of Wound, Ostomy and Continence Nursing, vol. 33, No. 6 Suppl, pp. S3-S8, Nov. 2006.
J. Viventi, D.-H. Kim, J. D. Moss, Y.-s. Kim, J. A. Blanco, N. Annetta, A. Hicks, J. Xiao, Y. Huang, D. J. Callans, J. A. Rogers, and B. Litt, "A conformal, bio-interfaced class of silicon electronics for mapping cardiac electrophysiology." Science translational medicine, vol. 2, No. 24, p. 24ra22,Mar. 2010.
J. A. Rogers, T. Someya, and Y. Huang, "Materials and mechanics for stretchable electronics." Science (New York, N. Y.), vol. 327, No. 5973, pp. 1603-1607, Mar. 2010.

(56) References Cited

OTHER PUBLICATIONS

S. Wang, M. Li, and Q. Lu, "Filter Paper with Selective Absorption and Separation of Liquids that Differ in Surface Tension," ACS Applied Materials & Interfaces, vol. 2, No. 3, pp. 677-683, Mar. 2010.
M. I. Tiwana, S. J. Redmond, and N. H. Lovell, "A review of tactile sensing technologies with applications in biomedical engineering," Sensors and Actuators A: Physical, vol. 179, pp. 17-31, Jun. 2012.
H. Yousef, M. Boukallel, and K. Althoefer, "Tactile sensing for dexterous in-hand manipulation in robotics—A review," Sensors and Actuators A: Physical, vol. 167, No. 2, pp. 171-187, Jun. 2011.
R. R. Sondergaard, M. Hösel, and F. C. Krebs, "Roll-to-Roll fabrication of large area functional organic materials," Journal of Polymer Science Part B: Polymer Physics, vol. 51, No. 1, pp. 16-34, Jan. 2013.
K. Jain, M. Klosner, M. Zemel, and S. Raghunandan, "Flexible Electronics and Displays: High-Resolution, Roll-to-Roll, Projection Lithography and Photoablation Processing Technologies for High-Throughput Production," Proceedings of the IEEE, vol. 93, No. 8, pp. 1500-1510, Aug. 2005.
K. Burczak, E. Gamian, and A. Kochman, "Long-term in vivo performance and biocompatibility of poly(vinyl alcohol) hydrogel macrocapsules for hybrid-type artificial pancreas," Biomaterials, vol. 17, No. 24, pp. 2351-2356, Jan. 1996.
C.-H. Chen, A. Torrents, L. Kulinsky, R. D. Nelson, M. J. Madou, L. Valde-vit, and J. C. LaRue, "Mechanical characterizations of cast Poly(3,4-ethylenedioxythiophene):Poly(styrenesulfonate)/Polyvinyl Alcohol thin films," Synthetic Metals, vol. 161, No. 21-22, pp. 2259-2267, Nov. 2011.
D. Garlotta, "A literature review of poly (lactic acid)," Journal of Polymers and the Environment, vol. 9, No. 2, 2001.
S. Mueller, B. Kruck, and P. Baudisch, "LaserOrigami: laser-cutting 3D objects," in Proceedings of the SIGCHI Conference on Human Factors in Computing Systems, 2013, pp. 2585-2592.
A. Toossi, M. Daneshmand, and D. Sameoto, "A low-cost rapid prototyping method for metal electrode fabrication using a CO02 laser cutter," Journal of Micromechanics and Microengineering, vol. 23, No. 4, p. 047001, Apr. 2013.
J. Yuan, J. Chen, and C. He, "Research of micro removing copper foil of FCCL assisted with laser," in 2011 IEEE International Conference on Mechatronics and Automation. IEEE, Aug. 2011, pp. 749-754.
A. K. Yetisen, M. S. Akram, and C. R. Lowe, "Paper-based microfluidic point-of-care diagnostic devices." Lab on a chip, vol. 13, No. 12, pp. 2210-2251, Jun. 2013.
G. Chitnis, T. Tan, and B. Ziaie, "Laser-assisted fabrication of batteries on wax paper," Journal of Micromechanics and Microengineering, vol. 23, No. 11, p. 114016(5pp), Nov. 2013.
G. Chitnis, Z. Ding, C.-L. Chang, C. A. Savran, and B. Ziaie, "Laser-treated hydrophobic paper: an inexpensive microfluidic platform." Lab ona chip, vol. 11, No. 6, pp. 1161-1165, Mar. 2011.
L. S. Nair and C. T. Laurencin, "Polymers as biomaterials for tissue engineering and controlled drug delivery." Advances in biochemical engineering/biotechnology, vol. 102, No. Oct. 2005, pp. 47-90, Jan. 2006.
P. B. Maurus and C. C. Kaeding, "Bioabsorbable implant material review," Operative Techniques in Sports Medicine, vol. 12, No. 3, pp. 158-160, Jul. 2004.
A. W. Martinez, S. T. Phillips, N. Nie, C.-M. Cheng, E. Carrilho, B. J. Wiley, and G. M. Whitesides, "Programmable diagnostic devices made from paper and tape." Lab ona chip, vol. 10, No. 19, pp. 2499-2504, Oct. 2010.
C. Rivet, H. Lee, A. Hirsch, S. Hamilton, and H. Lu, "Microfluidics for medical diagnostics and biosensors," Chemical Engineering Science, vol. 66, No. 7, pp. 1490-1507, Apr. 2011.
D. Nilsson, "An all-organic sensor-transistor based on a novel electrochemical transducer concept printed electrochemical sensors on paper," Sensors and Actuators B: Chemical, vol. 86, pp. 193-197, Sep. 2002.
P. Spicar-Mihalic, B. Toley, J. Houghtaling, T. Liang, P. Yager, and E. Fu, "CO 2 laser cutting and ablative etching for the fabrication of paper-based devices," Journal of Micromechanics and Microengineering, vol. 23, No. 6, p. 067003, Jun. 2013.
W. K. T. Coltro, D. P. de Jesus, J. A. F. da Silva, C. L. do Lago, and E. Carrilho, "Toner and paper-based fabrication techniques for microfluidic applications," ELECTROPHORESIS, vol. 31, No. 15, pp. 2487-2498, Jul. 2010.
R. Rahimi, S. S. Htwe, M. Ochoa, A. Donaldson, M. Zieger, R. Sood, A. Tamayol, A. Khademhosseini, A. Ghaemmaghami, and B. Ziaie, "Paper-based in-vitro model for on-chip investigation of the human respiratory system," Lab Chip, 2016.
M. Ochoa, R. Rahimi, T. L. Huang, N. Alemdar, A. Khademhosseini, M. R. Dokmeci, and B. Ziaie, "A paper-based oxygen generating platform with spatially defined catalytic regions," Sensors and Actuators B: Chemical, vol. 198, pp. 472-478, Jul. 2014.
Xing Liang and S. Boppart, "Biomechanical Properties of In Vivo Human Skin From Dynamic Optical Coherence Elastography," IEEE Transactions on Biomedical Engineering, vol. 57, No. 4, pp. 953-959, Apr. 2010.
R. H. Müller and D. L. Clegg, "Automatic Paper Chromatography," Analytical Chern-istry, vol. 21, No. 9, pp. 1123-1125, Sep. 1949.
L. Jeong, l.-S. Yeo, H. N. Kim, Y. I. Yoon, D. H. Jang, S. Y. Jung, B.-M. Min, and W. H. Park, "Plasma-treated silk fibroin nanofibers for skin regeneration," International Journal of Biological Macromolecules, vol. 44, No. 3, p. 222-228, Apr. 2009.
S. C. Jin, H. S. Baek, Y. I. Woo, M. H. Lee, J.-S. Kim, J.-C. Park, Y. H. Park, D. K. Rah, K.-H. Chung, S. J. Lee, and I. H. Han, "Beneficial effects of microwave-induced argon plasma treatment on cellular behaviors of articular chondrocytes onto nanofibrous silk fibroin mesh," Macromolecular Research, vol. 17, No. 9, pp. 703-708, Sep. 2009.
V. P. Ribeiro, L. R. Almeida, A. R. Martins, I. Pashkuleva, A. P. Marques, A. S. Ribeiro, C. J. Silva, G. Bonifácio, R. A. Sousa, R. L. Reis, and A. L. Oliveira, "Influence of different surface modification treatments on silk biotextiles for tissue engineering applications," Journal of Biomedical Materials Research Part B: Applied Biomaterials, vol. 104, No. 3, pp. 496-507, Apr. 2016.
S. Özkar, "Enhancement of catalytic activity by increasing surface area in heterogeneous catalysis," Applied Surface Science, vol. 256, No. 5, pp. 1272-1277, Dec. 2009.
D. B. Broughton and R. Wentworth, "Mechanism of Decomposition of Hydrogen Peroxide Solutions with Manganese Dioxide. I," J. Am. Chem. Soc., vol. 69, No. 4, pp. 741-744, 1947.
D. B. Broughton, R. Wentworth, and M. Laing, "Mechanism of Decomposition of Hydrogen Peroxide Solutions with Manganese Dioxide. II," J. Am. Chem. Soc., vol. 69, No. 4, pp. 744-747, 1947.
B. Ziaie, "A Flexible Smart Wound Dressing with Integrated On-Demand O2-Release and Sensing Capability," NetFlex Smart Dressing Project, Dec. 15, 2015.
M. Ochoa, C.K. yoon, and B. Ziaie, "Laser-fabricated, self-forming swimmers with catalytic propulsion and magnetic navigation," J microelectomech S, under review.
R. Rahimi, S.S. Htwe, M. Ochoa, A. Donaldson, M. Zieger, R. Sood, A. Tamayol, A. Khademhosseini, A. Ghaemmaghami, and B. Ziaie, "Paper-based in-vitro model for on-chip investigation of the human respiratory system," Lab Chip, accepted.
R. Rahimi, M. Ochoa, and B. Ziaie, "Direct laser writing of porous-carbon/silver nanocomposite for flexible electronics," ACS Appl. Mater. Interfaces, vol. 8, No. 26, pp. 16907-16913, Jul. 2016.
M. Ochoa, H. Jiang, J.H. Park, A. Otte, R. Pinal, and B. Ziaie, "Nanoparticle-enabled wireless monitoring and characterization of physical degradation kinetics in pharmaceutical gelatin films," Sens. Actuators A: Phys., vol. 241, 2016, pp. 238-244.
R. Rahimi, M. Ochoa, T. Parupudi, X. Zhao, I.K. Yazdi, M.R. Dokmeci, A. Tamayol, A. Khademhosseini.and B. Ziaie, "A low-cost flexible pH sensor array for wound assemssment," Sens. Actuators B:Chem., vol. 229, 2016, pp. 609-617.
W. Yu, R. Rahimi, M. Ochoa, R. Pinal, and B. Zizie, "A smart capsule with Gl-tract-location-specific payload release," IEEE Trans. Biomed. Eng., vol. 62, No. 9, 2015, pp. 2289-2295.
R. Rahimi, M. Ochoa, A. Donaldson, T. Parupudi, M. R. Dokmeci, A. Khademhosseini, A. Ghaemmaghami, and B. Ziaie, "A Janus-

(56) References Cited

OTHER PUBLICATIONS paper PDMS platform for air-liquid interface cell culture applications," J. Micromech. Microeng., vol. 25, 2015, 055015.

R. Rahimi, M. Ochoa, W. Yu, and B. Ziaie, "Highly stretchable and sensitive unidirectional strain sensor via laser carbonization," ACS Appl. Mater. Interfaces, vol. 7, No. 8, 2015, pp. 4463-4470.

R. Rahimi, M. Ochoa, W. Yu, and B. Ziaie, "A sewing-enabled stitch-and-transfer method for robust, ultra-stretchable, conductive interconnects," J. Micromech. Microeng., vol. 24, 2014, 095018.

A. H. Najafabadi, A. Tamayol, N. Annabi, M. Ochoa, R. Rahimi, P. Mostafalu, M. Akbari, M. Nikkhah, M. R. Dokmeci, S. Sonkusale, B. Ziaie, A. Khademhosseini, "Biodegradable nanofibrous polymeric substrates for generating elastic and flexible electronics," Adv. Mater., vol. 26, No. 33, pp. 5823-5830, Sep. 2014.

M. Ochoa, R. Rahimi, and B. Ziaie, "Flexible Sensors for Chronic Wound Management," IEEE Rev. Biomed. Eng., 2014.

P.-A. Vidi, T. Maleki, M. Ochoa, L. Wang, S. M. Clark, J. F. Leary, and S. A. Lelièvre, "Disease-on- a-Chip: Mimicry of Tumor Growth in Mammary Ducts," Lab Chip, vol. 14, No. 1, pp. 172-177, 2014.

M. Ochoa, R. Rahimi, Tiffany L. Huang, N. Alemdar, A. Khademhosseini, M. R. Dokmeci, and B. Ziaie, "A paper-based oxygen generating platform with spatially-defined catalytic regions for chronic wound treatment," Sens. Actuators B: Chem, vol. 198, pp. 472-478, Jul. 2014.

M. Ochoa, G. Chitnis, and B. Ziaie, "Laser-micromachined cellulose acetate adhesive tape as a low-cost smart material," Jm Polymm Scim B Polym. Phys., vol. 51, No. 17, 2013, pp. 1263-1267.

M. Ochoa, P. Wei, A. J. Wolley, K. J. Otto, and B. Ziaie, "A hybrid PDMS-Parylene subdural multi-electrode array," Biomed. Microdevices, Jan. vol. 15, No. 3, 2013, pp. 437-443.

M. Ochoa, C. Mousoulis, and B. Ziaie, "Polymeric microdevices for transdermal and subcuta- neous drug delivery," Adv. Drug Delivery Rev., vol. 64, No. 14, 2012, pp. 1603-1616.

M. Ochoa and B. Ziaie, "A fermentation-powered thermopneumatic pump for biomedical applications," Lab Chip, vol. 12, No. 20, 2012, pp. 4044-4048.

M. Ochoa and B. Ziaie, "Analysis of novel methods to determine the accuracy of the OmniPod insulin pump: a key component of the artificial pancreas system.," J. Diabetes Sci. Technol., vol. 5, No. 6, 2011, pp. 1519-1520.

C. Mousoulis, M. Ochoa, D. Papageorgiou, and B. Ziaie, "A skin-contact-actuated micropump for transdermal drug delivery," IEEE Trans Biomed. Eng., vol. 58, 2011, pp. 1492-1498.

H. Jiang, R. Rahimi, M. Ochoa, T. Parupudi, and B. Ziaie,"A pH-regulated drug delivery device for targeting infected regions in chronic dermal wounds," in Proceedings of MicroTAS '16, 2016.

M. Ochoa, C. K. Yoon, and B. Ziaie, "Flexible self-forming swimmers with catalytic propulsion and magnetic navigation," in MEMS 2016, Shanghai, China, 2016, pp. 1161-1164.

R. Rahimi, M. Ochoa, M. Zieger, R. Sood, and B. Ziaie, "A wireless strain sensor for wound monitoring with direct laser-defined patterning on a commercial dressing," in MEMS 2016, Shanghai, China, 2016, pp. 481-484.

J. Zhou, A. Kim, M. Ochoa, H. Jiang, and B. Ziaie, "An ultrasonically powered micropump for on-demand in-situ drug delivery," in MEMS 2016, Shanghai, China, 2016, pp. 349-352.

C. K. Yoon, A. Kim, M. Ochoa, T. Parupudi, and B. Ziaie, "A low-cost wearable radiation sensor based on dose response viability of yeast cells," in MEMS 2016, Shanghai, China, 2016, pp. 1066-1069.

M. Ochoa, J. Zhou, R. Rahimi, V. Badwaik, D. Thompson, and B. Ziaie, "Rapid 3D-print-and- shrink fabrication of biodegradable microneedles with complex geometries," in Transducers 2015, Anchorage, AK, 2015.

H. Jiang, M. Ochoa, J.H. Park, A. Otte, R. Pinal, and B. Ziaie, "Wireless screening of degrada-tion kinetics in pharmaceutical gelatin films," in Transducers 2015, Anchorage, AK, 2015.

R. Rahimi, M. Ochoa, W. Yu, and B. Ziaie, "A highly stretchable pH sensor array using elastomer-embedded laser carbonized patterns," in Transducers 2015, Anchorage, AK, 2015.

R. Rahimi, M. Ochoa, W. Yu, and B. Ziaie, "A low-cost fabrication technique for direct sewing stretchable interconnetions for wearable electronics," in Transducers 2015, Anchorage, AK, 2015.

L. Ben-Yehoshua, M. Ochoa, and B. Ziaie, "Rapid fabrication of 3D elastomeric structures via laser-machining and vacuum deformation," in Transducers 2015, Anchorage, AK, 2015.

Z.B. Hughes, R. Rahimi, M. Ochoa, and B. Ziaie, "Rapid prototyping of piezoresistive mems sensors via a single-step laser carbonization and micromachining process," in Transducers 2015, Anchorage, AK, 2015.

M. Ochoa, H. Jiang, R. Rahimi, and B. Ziaie, "Laser treated glass platform with rapid wicking- driven transport and particle separation capabilities," in MEMS 2015, Estoril, Portugal, 2015.

R. Rahimi, M. Ochoa, W. Yu, and B. Ziaie, "A facile fabrication technique for stretchable interconnects and transducers via laser carbonization," in MEMS 2015, Estoril, Portugal, 2015.

T.S. Zhang, A. Kim, M. Ochoa, and B. Ziaie, "Controllable 'somersault' magnetic soft robotics," in MEMS 2015, Estoril, Portugal, 2015.

R. Rahimi, M. Ochoa, J. Zhou, A. Tamayol, M.R. Dokmeci, A. Khademhosseini, A. Ghaem-maghami, and B. Ziaie, "A hybrid PDMS/paper passive pump for slow-release/delivery of drugs in chronic dermal wounds," in µTAS 2015, San Antonio, TX, 2015.

R. Rahimi, M. Ochoa, M. R. Dokmeci, A. Khademhosseini, and B. Ziaie, "A Janus-paper PDMS platform for lab-on-a-chip applications," in Hilton Head 2014: A Solid-State Sensors, Actuators and Microsystems Workshop, 2014.

R. Rahimi, M. Ochoa, W. Yu, and B. Ziaie, "A sewing-enabled stitch-and-transfer method for robust, ultra-stretchable, conductive interconnects," in Hilton Head 2014: A Solid-State Sensors, Actuators and Microsystems Workshop, 2014.

M. Ochoa, R. Rahimi, N. Alemdar, M. R. Dokmeci, A. Khademhosseini, and B. Ziaie, "A flexible, laser-defined, paper platform for localized oxygen generation and delivery," in Proc. Transducers 2013, Actuators and Microsystems, 2013.

M. Ochoa, R. Rahimi, R. Shi, and B. Ziaie, "An impact sensing platform for spinal cord injury experiments," in Proc. Sensors'13, 2013.

R. Rahimi, M. Ochoa, and B. Ziaie, "A low-cost flexible electrochemical sensor for monitoring silver ion concentration in alginate wound dressings," in Proc. Sensors '13, 2013.R. Rahimi, M. Ochoa, and B. Ziaie, "A low-cost flexible electrochemical sensor for monitoring silver ion concentration in alginate wound dressings," in Proc. Sensors '13, 2013.

M. Ochoa, C. Mousoulis, and B. Ziaie, "A sequential-dosage fluorocarbon-actuated microp-ump," in Proceedings of MicroTAS '11, 2011, pp. 1807-1809.

C. Mousoulis, M. Ochoa, and B. Ziaie,"A skin-contact-actuated dispenser/pump for transder-mal drug delivery," in Proceedings of MicroTAS '10, 2010, pp. 749-751.

M. Ochoa, R. Rahimi, and B. Ziaie, "Laser-Enabled Fabrication Technologies for Low-Cost Flexible/Conformal Cutaneous Wound Interfaces," in Stretchable Bioelectronics for Medical Devices and Systems, J. A. Rogers, R. Ghaffari, and D.-H. Kim, Eds. Springer International Publishing, 2016, pp. 207-226.

M. Ochoa. "A piezoelectrically actuated titanium micropump for drug delivery." (Master's thesis) ProQuest Dissertations and Theses, pp. 82. 2012.

Manuel Ochoa, "Laser-Processed Parchment Paper for Fabrication of Chronic Wound Dressings With Selective Oxygenation," Dec. 1, 2016, 120 pages.

Babak Ziaie, "A Flexible Smart Wound Dressing with Integrated On-Demand 02-Release and Sensing Capability," Dec. 15, 2015, 6 pages.

Zhang et al., An O2 Self-Supplementing and Reactive-Oxygen-Species-Circulating Amplified Nanoplatform via H20/H202 Splitting for Tumor Imaging and Photodynamic Therapy, 2017, 14 pages.

(56) References Cited

OTHER PUBLICATIONS

Santoro et al., "Development of oxygen and temperature sensitive membranes using molecular probes as ratiometric sensor," May 12, 2016, 9 pages.
Santoro et al., "Monitoring oxygen permeating through polymeric packaging films using a ratiometric luminescent sensor," May 24, 2016, 8 pages.
Zhao et al., "Morphology impact on oxygen sensing ability of Ru(dpp)3CI2 containing biocompatible polymers," Apr. 11, 2015, 6 pages.
Li et al., "Non-invasive transdermal two-dimensional mapping of cutaneous oxygenation with a rapid-drying liquid bandage," Oct. 1, 2014, 17 pages.
De Smet et al., "Oxygen therapies and their effects on wound healing," 2017, 18 pages.
Jeong et al., "Plasma-treated silk fibroin nanofibers for skin regeneration," Dec. 25, 2008, 7 pages.
Mostafalu et al., "Smat flexible wound dressing with wireless drug delivery," 2015, 4 pages.
Dissemond et al., "Topical oxygen wound therapies for chronic wounds: a review," Feb. 2015, 9 pages.
Gottrup, "Use of Oxygen Therapies in Wound Healing," 2017, 44 pages.
Mostafalu et al., "Wireless Flexible Smart Bandage for Continuous Monitoring of Wound Oxygenation," Oct. 2015, 8 pages.

\* cited by examiner

FLUORESCENT OXYGEN SENSING INK

CROSS-REFERENCE TO RELATED APPLICATIONS

This application claims the benefit of 35 U.S.C. § 119(e) of U.S. Provisional Patent Application No. 62/636,560 filed on Feb. 28, 2018, entitled, "FLUORESCENT OXYGEN SENSING INK," the contents of which are incorporated herein by reference in its entirety.

This application is a continuation of PCT Patent Application Serial No. PCT/US2018/020284, filed on Feb. 28, 2018, entitled, "FLUORESCENT OXYGEN SENSING INK," the contents of which are incorporated herein by reference in their entirety.

STATEMENT REGARDING FEDERALLY SPONSORED RESEARCH OR DEVELOPMENT

This invention was made with government support in part by NextFlex (P.C. 1.0) under Air Force Research Laboratory Cooperative Agreement No. FA8650-15-2-5401. The government has certain rights in the invention.

BACKGROUND

Chronic non-healing wounds (e.g., diabetic foot and bed sores) impact over 6.5 million Americans per year, costs in excess of $25 billion to treat on an annual basis, and are on the rise due to increasing levels of obesity and diabetes compounded by an aging population. Current treatments are expensive, labor intensive, and generic, relying on regular cleaning, debridement, oxygen therapy, and topical or systemic administration of antibiotics. Commercially-available dressings (e.g., alginate, hydrogels, hydro-colloids, foams, etc.) have not proven to be significantly effective in reducing the burden. An ideal dressing integrates sensors (pH, oxygen, and inflammatory mediators), drug/cell delivery (antibiotics, growth factors, stem cells, and oxygen), and electronic intelligence to drastically improve wound care by measuring individual responses and enabling appropriate adjustments to therapy.

Suboptimal oxygenation of the wound bed is a major healing inhibitor in chronic wounds. Unlike acute injuries that receive sufficient oxygen via a functional blood vessel network, chronic wounds often suffer from the lack of a proper vascular network; thus being incapable of providing sufficient oxygen for tissue growth. While the lack of oxygen may trigger vascular regeneration, the severity and depth of wounds can prevent adequate regeneration, causing wound ischemia. Modern medical treatment of hypoxic chronic wounds typically employs hyperbaric oxygen therapy, which requires bulky equipment and often exposes large areas of the body to unnecessarily elevated oxygen concentrations that can damage healthy tissue. A more practical approach is topical oxygen therapy (TOT) in which the dressing itself can generate the required oxygen.

SUMMARY

In one aspect of the present disclosure, a fluorescent oxygen sensing ink includes at least one organic solvent, at least one polymer binder disposed in the at least one organic solvent, and an oxygen-sensitive fluorescent dye disposed in the at least one organic solvent. The oxygen-sensitive fluorescent dye and the at least one polymer can interact to form a moisture-resistant film.

In another aspect, an oxygen sensing wound dressing is provided. The oxygen sensing wound dressing includes a substrate, at least one fluid channel bonded to the substrate, and an oxygen sensing ink printed on the substrate. The oxygen sensing ink can include at least one organic solvent, at least one polymer binder, and an oxygen-sensitive dye capable of fluorescing in the presence of oxygen.

In yet another aspect, a method of fabricating an oxygen sensor is provided. The method can include providing a substrate and providing an oxygen sensing ink. The oxygen sensing ink can include at least one organic solvent, at least one polymer binder, and an oxygen-sensitive fluorescent dye. The oxygen sensing ink can be printed on a surface of the substrate.

These and other features, advantages, and objects of the present disclosure will be further understood and appreciated by those skilled in the art by reference to the following specification, claims, and appended drawings.

DETAILED DESCRIPTION

One aspect of the present disclosure is an ink that can be utilized to fabricate "smart" dressings for chronic wounds. A fluorescent oxygen sensing ink includes an organic solvent, a polymer binder such as ethyl cellulose, and a fluorescent dye that is dispersed or dissolved in the solution. The ink can be printed on a thin flexible substrate such as paper, and the ink forms a moisture resistant flexible film that can be utilized in an oxygen sensor. The smart dressing measures the amount of oxygen present in a wound and pumps more oxygen as necessary. The smart dressing integrates oxygen delivery and sensing onto a single low-cost, manufacturable, flexible dressing. The smart dressing may be fabricated on a biocompatible substrate (e.g. paper) that incorporates patterned catalytic oxygen generating regions and an array of oxygen sensors connected to an electronic readout module. The use of a paper substrate provides structural stability and flexibility while simultaneously offering printability, selective gaseous filtering, and physical/chemical protection. However, it will be understood that the smart dressing is not limited to paper substrates, and virtually any hydrophobic to partially hydrophilic substrate may be utilized.

Figure 1:
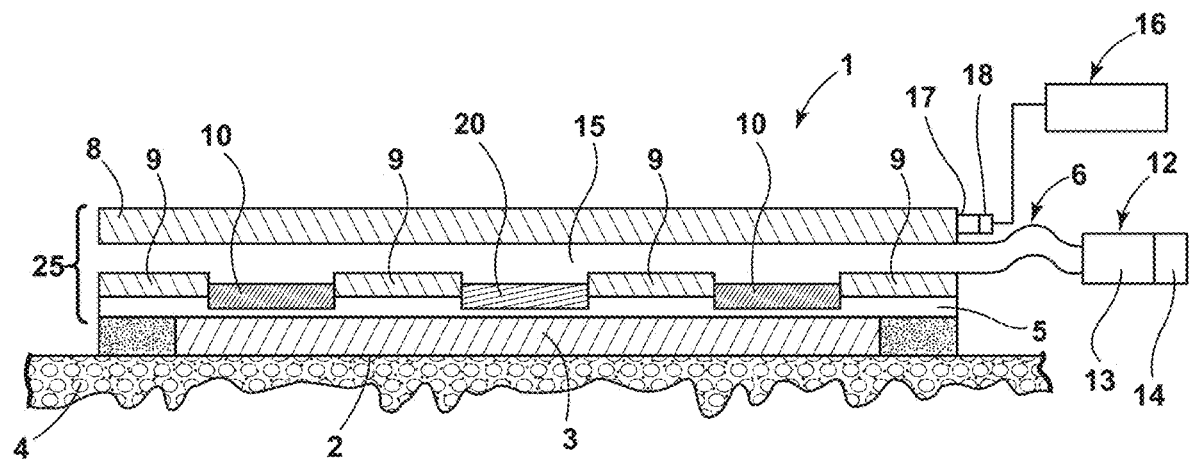
FIG. 1 is a schematic cross-sectional view of a smart wound dressing with integrated oxygen sensing and delivery according to one aspect of the present disclosure.

With reference to FIG. 1, a smart dressing 1 according to one aspect of the present disclosure includes a substrate layer 5 forming a backbone onto which one or more oxygen generating modules 10 and oxygen sensing modules 20 are printed. A fluid conduit 6 is fluidly connected to a pump/reservoir unit 12 including a reservoir 13 and pump 14. A network of low-profile and flexible microfluidic channels 15 are formed by polydimethylsiloxane (PDMS) layers 8 and 9 that are bonded to the substrate layer 5. The microfluidic channels 15 guide and deliver hydrogen peroxide from fluid conduit 6 to the oxygen generating modules 10. A wound-facing side 2 of smart dressing 1 can include a collagen-glycosaminoglycan biodegradable matrix 3 (such as INTEGRA®, which may be purchased from Integra Life Sciences Corp.), which provides a scaffold for cellular invasion and capillary growth while permitting oxygen exchange between the oxygen generating modules 10 and the oxygen sensing modules 20 and a wound bed 4. The matrix 3 is retained in the wound 4 after initial application. The sensing modules/generating modules 20, 10 together with the substrate layer 5 and PDMS layers 8, 9 form a module 25 that can be delaminated from the matrix 3 and replaced periodically.

As discussed in more detail below, other aspects of the present disclosure include reliable processes for inkjet printing the oxygen generating and oxygen sensing modules 10, 20 as well as suitable lamination and bonding techniques (e.g., plasma, adhesives) for integrating the various layers of the smart dressing 1. An electronic readout and control module 16 can be connected to an edge 17 of the smart dressing 1 via an edge-mounted connector 18 and the reservoir/pump unit 12. The smart dressing 1 can be connected to the reservoir/pump unit 12 via fluid conduit 6 to supply H$_2$O$_2$ through the microfluidic channels 15. The reservoir/pump unit 12 may be fabricated via soft micromolding techniques or other suitable processes.

Substrate layer 5 may include laser-treated parchment paper. In particular, laser-treated parchment paper may possess high mechanical strength (e.g., >70 MPa) to withstand human motion, high elastic modulus when dry (e.g., >300 kPa) for easy handling during fabrication, low elastic modulus (e.g., <50 kPa) when wet for interfacing with similarly soft tissue, permeability to gas and not water at low pressures, and permeable to oxygen diffusion. When laser-rastered, the surface energy of the paper increases.

According to an aspect of the present disclosure, the substrate layer 5 may be any rastered or unrastered paper or coated paper, such as parchment paper, wax coated paper, or chromatography paper; any polyester films such as polyethylene terephthalate (PET) or polyethylene-naphthalate (PEN); any polyimide films such as KAPTON™, UPILEX™; any polyurethane plastics/thermoplastic elastomer materials such as thermoplastic polyurethane; any silicone-based organic polymers such as polydimethylsiloxane (PDMS) and ECOFLEX™; or Tyvek®.

One aspect of the present disclosure is a fluorescent oxygen sensing ink and process for printing the ink. The oxygen sensing ink can be an ink system that generally includes a solvent, an oxygen-sensitive dye, and a polymer binder. The solvent may include aqueous buffers or an organic solvent such as ethanol, dimethyl sulfoxide (DMSO), dimethyl formamide, isopropyl alcohol, acetone, toluene, or mixtures thereof. The oxygen-sensitive dye may be a fluorescent dye selected from the group including complexes of ruthenium, osmium tetroxide, rhodium acetate, chromium, palladium or other dyes that fluoresce when exposed to UV/visible light in the presence of oxygen. The ink may comprise any polymer based material that provides uniform dispersion or is completely soluble in the ink system for different additive print manufacturing processes such as screen, gravure, flexography, inkjet, and aerosol jet. The particle size of the polymers dispersed in the ink system are dependent on the nozzle size of the inkjet heads if inkjet printing processes are utilized. For example, if the nozzle diameter is 21 μm, then the particle size should be less than about 0.2 μm to avoid agglomeration and clogging of print head nozzles. For printing, the surface tension of the ink is preferably less than the surface energy of the substrate to adhere well. The surface energy of the substrate (e.g. paper) can be modified by employing UV, corona, plasma, sintering, or laser engraving processes to increase a surface energy of the substrate. The surface characteristics of the substrate can be modified as desired without adversely affecting or damaging the other characteristics/properties of the substrate. The fluorescent oxygen sensing ink according to the present disclosure can be printed on any hydrophobic to partially hydrophilic substrates. However, the oxygen sensing ink typically cannot be printed on a substrate that is completely hydrophilic. An oxygen sensing ink according to the present disclosure does not necessarily require any transparent or translucent substrate or any additional protective coating materials.

As noted above, an oxygen sensing ink according to the present disclosure includes one or more polymer binders that may include alkyl substituted cellulose materials. These alkyl substituted cellulose materials may be represented by Formula (I):

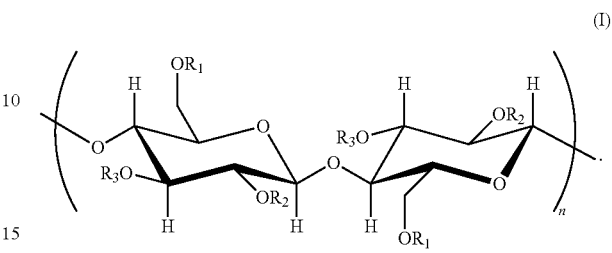

In Formula (I), $R_1$, $R_2$, and $R_3$ may each independently be hydrogen or an alkyl group having 1-8 carbons including, for example, methyl, ethyl, propyl, isopropyl, n-butyl, sec-butyl, pentyl, or combinations thereof. In some aspects, the polymer binder is ethyl cellulose. Ethyl cellulose has the following chemical structure where $R_1$ is ethyl, $R_2$ is ethyl, and $R_3$ is hydrogen as represented by Formula (II):

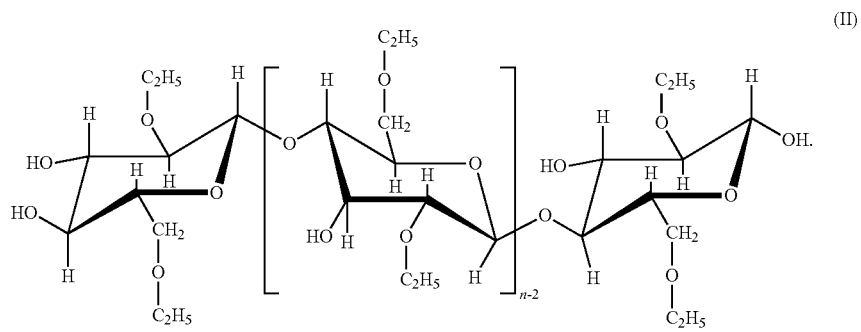

Ethyl cellulose does not contain any sulphonic or phosphonic groups or naphthylene groups. Cellulose containing repeating anhydroglucose rings having hydroxyl groups at the 2', 3', and 6' positions can be treated with an alkaline solution resulting in an alkali cellulose which in turn can be reacted with ethyl chloride to yield ethyl cellulose. In this reaction some hydroxyl (—OH) groups are replaced by ethoxyl (—OC$_2$H$_5$) groups. In some aspects, the degree of substitution of the 2', 3', and 6' hydroxyl groups may be from about 1.0 to about 3.0, from about 1.2 to about 2.6, from about 2.3 to about 3.0, or from about 1.8 to about 2.2. In other aspects, the degree of substitution may be greater than 10%, greater than 20%, greater than 30%, greater than 40%, greater than 50%, greater than 60%, greater than 70%, greater than 80%, greater than 90%, greater than 95%, greater than 98%, greater than 99% where the percentage is relative to the substitution of the 2', 3', and 6' cellulosic hydroxyl groups, or the hydroxyl groups may be quantitatively substituted with ethoxyl or other alkoxy groups. Not to be bound by theory but the increasing reactivity of the 2', 3', and 6' hydroxyl groups, respectively, will affect the substitution position as would be appreciated by one skilled in the art.

Ethyl cellulose can act as a water barrier film and provide moisture resistance. In contrast, other polymers, such as nitrocellulose, dissolve in water, and have poor moisture resistance. In other words, ethyl cellulose has hydrophobicity. Also, ethyl cellulose can provide suitable film formation, adhesion, high mechanical flexibility, and may allow for greater film coverage compared to some other cellulose derivatives. For example, nitrocellulose requires additional materials including synthetic resins (such as alkylated resins, maleic resins, ketone resins, urea resins, polyurethane resins, polyacrylates, and polyester and polyacrylate resins containing hydroxyl groups) and plasticizers (diisobutyl phthalate (DIBP), dicyclohexyl phthalate (DCHP), epoxidized soya oil (ESO), triphenyl phosphate) to be added to the oxygen sensing ink system in order to provide uniform film formation, adhesion, and/or flexibility to the printed layer of dye.

Although polydimethylsiloxane (PDMS) or polystyrene may be utilized as a polymer binder in some of the oxygen sensing ink formulations of the present disclosure, according to one aspect of the present disclosure, PDMS or polystyrene disperses in the ink system and bind to the ruthenium ("Ru'") dye. In contrast, ethyl cellulose can completely dissolve in the ink system, rather than be dispersed, and bind with the ruthenium dye to form a moisture resistant, flexible, continuous, and uniform film. In general, binders such as ethyl cellulose that dissolve completely or nearly completely in the ink system can provide better film formation, adhesion, and flexibility than binders that disperse in the ink system. An ink system according to the present disclosure can require minimal materials and simple fabrication steps, and can form a continuous uniform film with suitable adhesion and flexibility. According to one aspect of the present disclosure, the polymer binder can be selected from alkyl cellulose material, silicone-based polymers (such as polydimethylsiloxane (PDMS)), Ecoflex™, or polystyrene.

According to one example, the oxygen sensing ink system according to the present disclosure may include 98 weight percent (wt %) of an organic solvent, 1 weight percent of dye, and 1 weight percent of a polymer binder that is preferably completely dissolved in the ink system. The ink compositions can be varied as per the requirements of the additive printing processes.

According to one aspect of the present disclosure, an oxygen sensing ink system includes from about 75 wt % to about 99 wt % solvent, from about 0.1 wt % to about 5 wt % fluorescent dye, and from about 0.1 wt % to about 20 wt % polymer binder.

Figure 2:
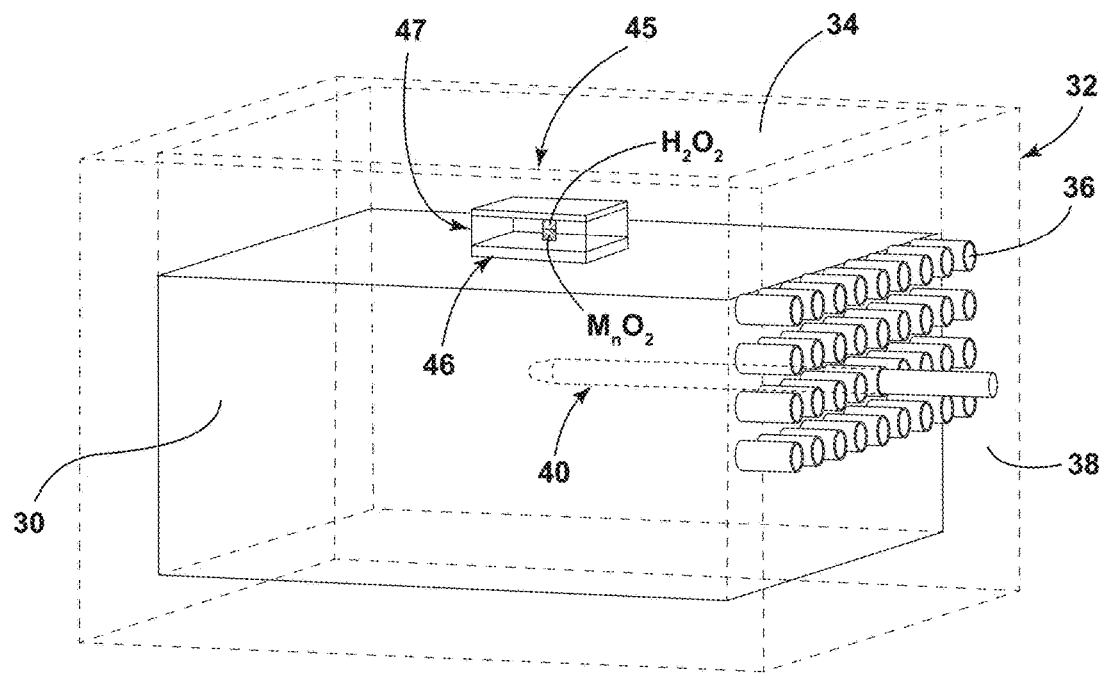
FIG. 2 is a schematic isometric view of a test setup for measuring oxygen diffusion into agarose gel.

To evaluate the ability to increase the oxygen concentration in a wound bed, oxygen diffusion was investigated on a surrogate wound bed (FIG. 2) comprising a sample of 0.3% agarose gel. An acrylic chamber 32 with open top 34 was assembled to hold the agarose gel sample 30. The chamber 32 includes an array of 2 mm holes 36 through a side wall 38 to allow insertion of an oxygen probe 40. Prior to testing, 0.3% agarose gel is prepared and stored in a hypoxic environment until ready for use. During testing, the agarose gel 30 is placed in the chamber 32. An oxygenation platform 45 was constructed by bonding laser-machined parchment paper 46 to PDMS 47 patterned with a chamber ($3\times3\times2$ mm$^3$) and a guide channel ($18\times1\times2$ mm$^3$). The laser-treated region within the chamber was a $3\times3$ mm$^2$ catalyst spot (deposited as described above). The chamber was filled with 30% $H_2O_2$ through the guide channel using a syringe pump to begin oxygen generation.

The oxygenation platform 45 was placed on top of (in contact with) the gel 30. The chamber 32 was then sealed with a Parafilm barrier to prevent significant oxygenation from the atmosphere. The same oxygen probe 40 is then inserted into a hole 36 of the chamber 32, penetrating the gel 30 until the tip is positioned 3 mm directly below the catalyst spot of the parchment paper 46. For this test the oxygen probe 40 was covered with a protector needle (not shown) to prevent mechanical damage to the probe 40 during insertion. The remaining holes 36 in the chamber 34 were sealed with adhesive tape to prevent oxygen diffusion from the atmosphere. The oxygen concentration in the gel 30 was monitored over time.

Referring again to FIG. 1, in clinical applications, the oxygenation platform may have an interfacial material between the substrate layer 5 and the wound to create intimate contact with the wound bed 4. To simulate this, the above experiment utilizing the evaluation set-up of FIG. 2 was repeated with a commercial dermal regeneration matrix (Integra®, available from Integra Life Sciences Corp.) as the interface between the parchment paper 46 and the agarose gel 30. The dermal regeneration matrix is 900 µm thick and is composed of cross-linked bovine tendon collagen and glycosaminoglycan that is indicated for the treatment of acute and chronic wounds, including diabetic skin ulcers. A 1 cm×1 cm sample of the Integra® dermal regeneration matrix was cut with a razor blade and sandwiched between the oxygenation platform 45 and the agarose gel 30. The rest of the experiment proceeded as above. As a control experiment, this test was repeated with empty microfluidics (i.e., no $H_2O_2$).

To investigate the range of spatial effect of an oxygenation spot on a gel substrate, the oxygenation experiments were repeated for multiple locations, and the rate of oxygenation was plotted as a function of both vertical and horizontal distance from the oxygen generation spot.

Figure 3:
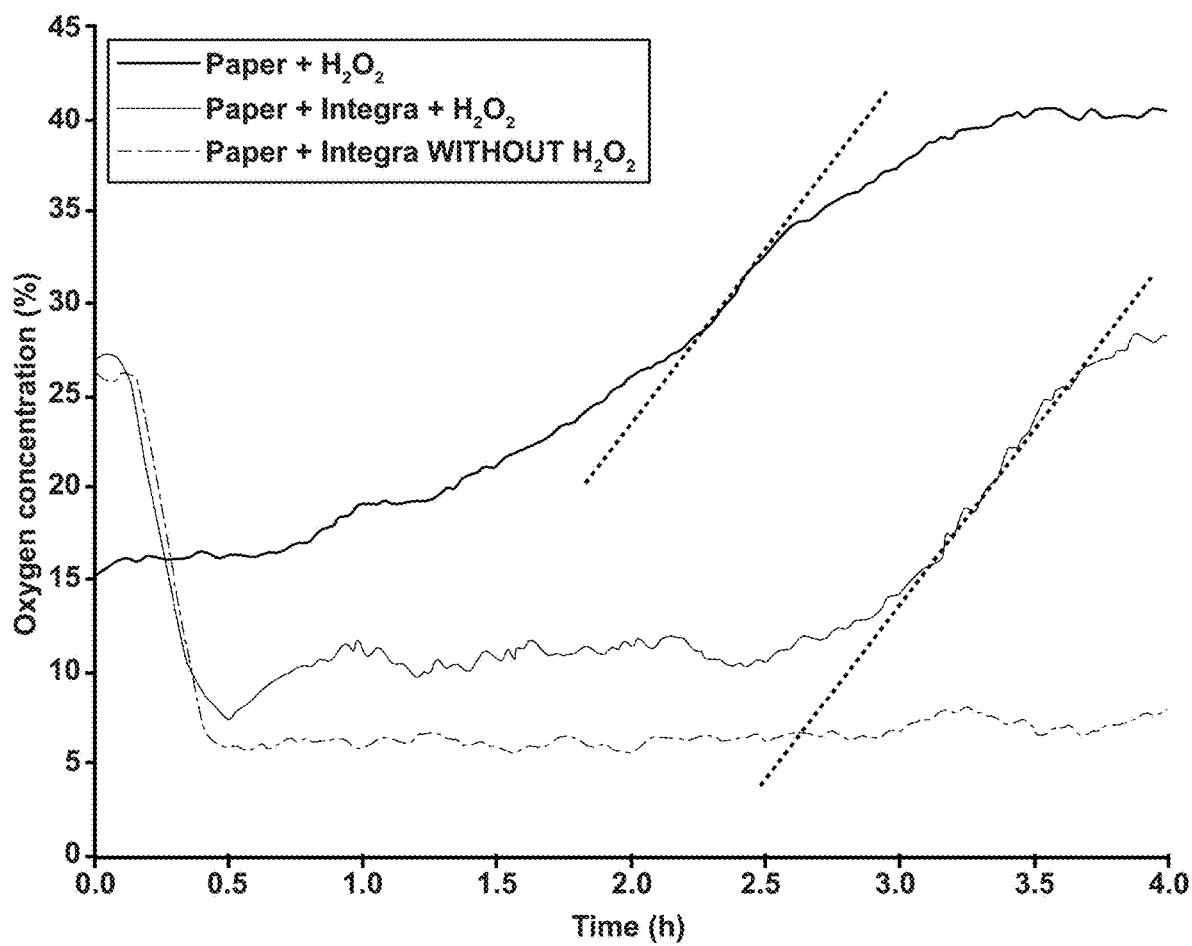
FIG. 3 is a graph showing oxygen generation and diffusion into agarose gel.

The results from the diffusion experiments into agarose gel 3 mm deep are presented in FIG. 3. For the case without a dermal regeneration matrix (Paper+$H_2O_2$), the solid bold line curve shows a monotonically-increasing oxygen level (from a partially hypoxic level of 15% to 40% 3 hours later) in the agarose gel 3 mm below an oxygenation spot. The curves show saturation in the oxygen level since for these experiments, a fixed amount of $H_2O_2$ was used (rather than a continuous flow). Although the level shown is not 100% saturation, the results do show that the platform is able to successfully raise the oxygen concentration 3 mm within the gel 30 to levels which are far from hypoxic. Therefore, if the gel 30 were a wound bed, it would be reasonable to expect improved healing as deep as 3 mm (or more) as a result of the oxygenation platform 45.

The two remaining curves represent the tests with the Integra® dermal regeneration matrix and show a different trend. In particular, the solid thin line curve, corresponding to the setup with the Integra® dermal regeneration matrix, the oxygenation platform 45, and peroxide-filled microfluidics (Paper+Integra®+$H_2O_2$) contains an initial shallow slope. This lag in the increase of oxygenation may be attributable to the extra time required for oxygen to diffuse through the Integra® dermal regeneration matrix layer. After 2.5 hours, however, the solid thin line curve (Paper+Integra®+$H_2O_2$) exhibits its highest rate of change in oxygen concentration (slope of 18.9% per hour), which is is similar to the highest rate (17.1% per hour) of the sample without dermal regeneration matrix (Paper+$H_2O_2$). The rate of change of the oxygen concentration suggests that although the dermal regeneration matrix causes an initial lag in oxygen diffusion, the eventual diffusion rate of oxygen approaches that of the oxygen generation platform 45 used alone. For comparison, the oxygen level does not increase during this time for the sample (dashed line curve) that does not contain peroxide in the microfluidics (Paper+Integra® WITHOUT $H_2O_2$).

One feature of the curves that should be clarified is the initial drop in oxygen for the two samples that include the Integra® dermal regeneration matrix. For both of these cases, the data shows an initially normoxic oxygen level. This corresponds to the reading of the oxygen probe 40 in atmosphere, prior to insertion into the gel 30 (at time 0). Following insertion, the oxygen concentration drops steadily. Although a quick drop in oxygen concentration (to hypoxic levels in the gel) might be expected, the curves show a 20-30 minute steady decay which may be attributed to atmospheric oxygen trapped in the oxygen probe 40 protector needle (described in the experimental setup above) which needs time to diffuse into the gel 30. After 30 minutes, however, the curves reach their minimum values (the oxygen level in the hypoxic gel, ≤15% $O_2$).

Figure 4:
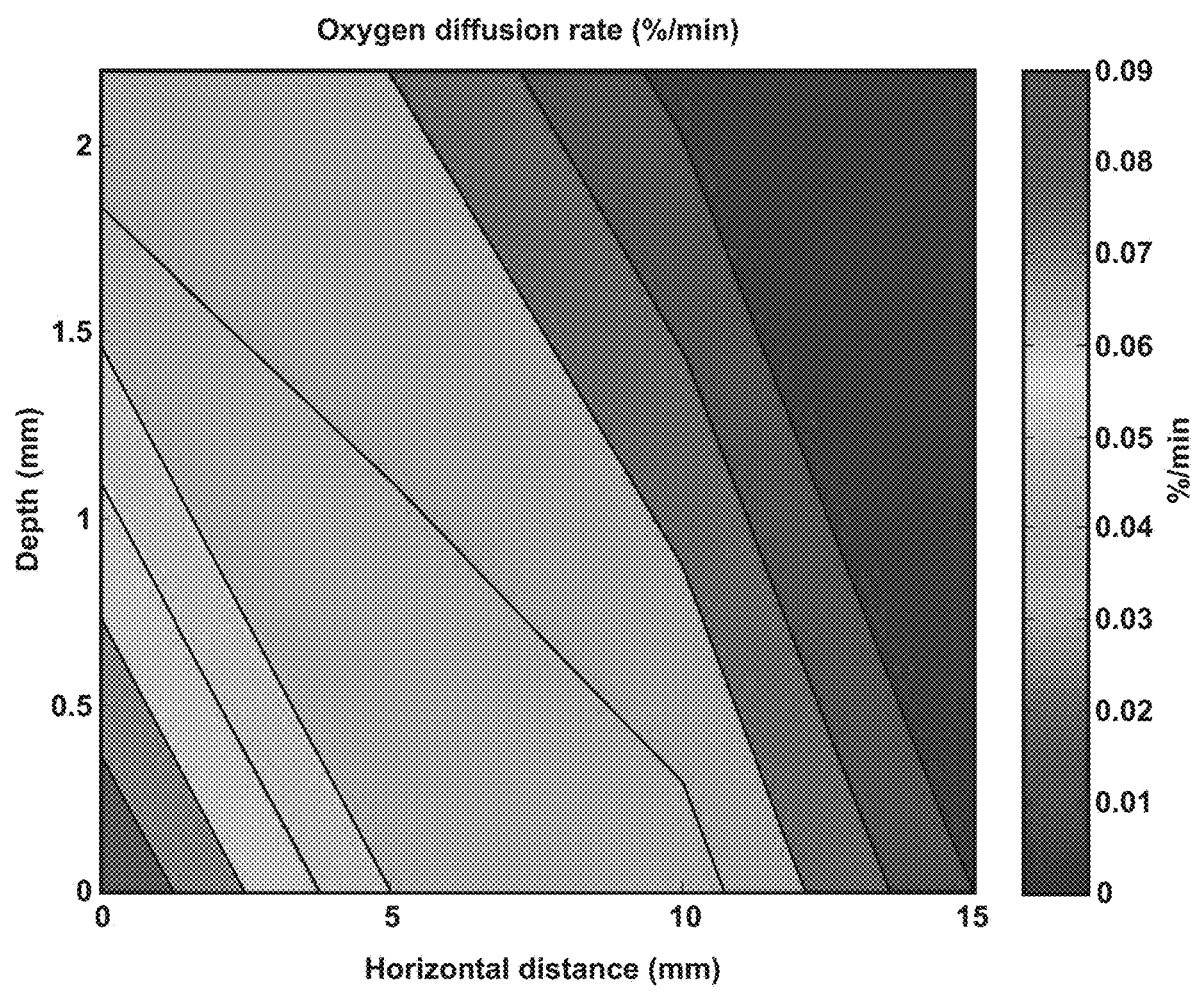
FIG. 4 is a graph showing 3D distribution of oxygen diffusion rate inside agarose gel from a single oxygen generation spot.

FIG. 4 shows the 3D spatial oxygen concentration by diffusing through a 0.9 mm thick dermal regeneration matrix into the hypoxic gel. The maximum oxygen diffusion rate is 0.09%/min (percentage per minute) at the surface of the gel just below the catalyst spot (0 mm depth and 0 mm horizontal distance); while the minimum oxygen diffusion rate is 0.004%/min at the position of 2.2 mm depth and 15 mm horizontal distance inside the gel. The oxygen diffusion rate shows a normal distribution in both the depth and horizontal directions. Within the 80% area under the normal curve, the critical oxygen diffusion rate is calculated by 0.09/e=0.03%/min. The oxygen generated from a 3×3 $mm^2$ catalyst spot can therefore cover a range with the radius of 10 mm following the surface and the depth of 2.2 mm directly beneath it. The oxygen concentration distribution through a single oxygen generation source can provide an experimental baseline for designing an oxygen generation platform with multiple sources to achieve an efficient (optimal) oxygen delivery rate for a large scale chronic wound.

Another aspect of the present disclosure is a mass-reproducible technique for creating PDMS micro channels and bonding them to parchment paper patterned with selective catalyst and oxygen-sensitive dye deposited. A repeatable bonding procedure between PDMS and parchment paper can provide for high-volume production. Several mass production technologies, such as screen printing, inkjet printing, lamination, etc., may be utilized to produce smart dressings according to the present disclosure.

PdTFPP (5,10,15,20-Tetrakis(pentafluorophenyl)-21H, 23H-porphine palladium(II)) and $Ru(dpp)_3Cl_2$ (Tris(4,7-diphenyl-1,10-phenanthroline) ruthenium II dichloride) are suitable candidates for oxygen sensing materials due to their ability to indicate the presence of oxygen. When the fluorescent dyes are exposed to UV/visible light (for example 455 nm blue light) in the presence of oxygen, the oxygen atoms strike the fluorescing complex and cause a change in energy which quenches its fluorescence. A higher oxygenated environment creates a higher possibility for such collisions to happen between oxygen atoms and the fluorescent complex, resulting in a lower fluorescence level.

The fluorescent properties of two materials being encapsulated in both poly-styrene and PDMS (polydimethylsiloxane) polymer binder materials were measured to determine the suitability of the materials in an oxygen sensing system. PdTFPP was purchased from Sigma-Aldrich and $Ru(dpp)_3Cl_2$ was purchased from Cayman Chemical. A dye solution of the material was made by dissolving 1 mg of PdTFPP or $Ru(dpp)_3Cl_2$ powder into 1 mL of chloroform. For PdTFPP, 1 mg of powder was also dissolved into 1 mL of heptane for testing. Poly-styrene (PS) sensing patches were prepared by mixing PS and dissolved dye solution at a ratio of 1:10 by weight. Then 20 μL of mixed solution was cast onto filter paper to form a patch with a diameter of 8 mm. The patch was left in the nitrogen chamber for drying for 24-hours before testing. The PDMS encapsulated sensing patches were fabricated by firstly depositing dye solution onto the filter paper. PDMS was then added to the filter paper after the removal of the solvent. The same amount of dye was used for all samples. The fluorescence spectrum was measured using a UV spectrophotometer. A zero oxygen solution was prepared by nitrogen bubbling a 0.15 mol/L $Na_2SO_3$ solution for 30 minutes.

Figure 5A:
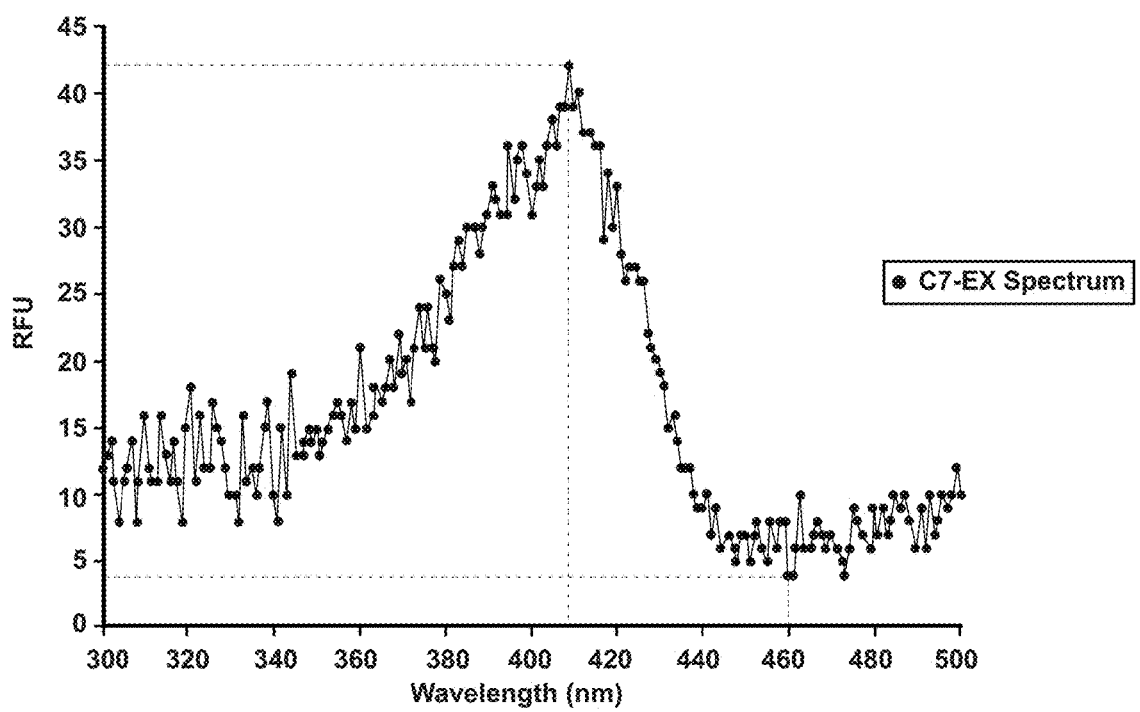
FIG. 5A is a graph showing an excitation spectrum (RFU) for PdTFPP dissolved in chloroform.
Figure 5B:
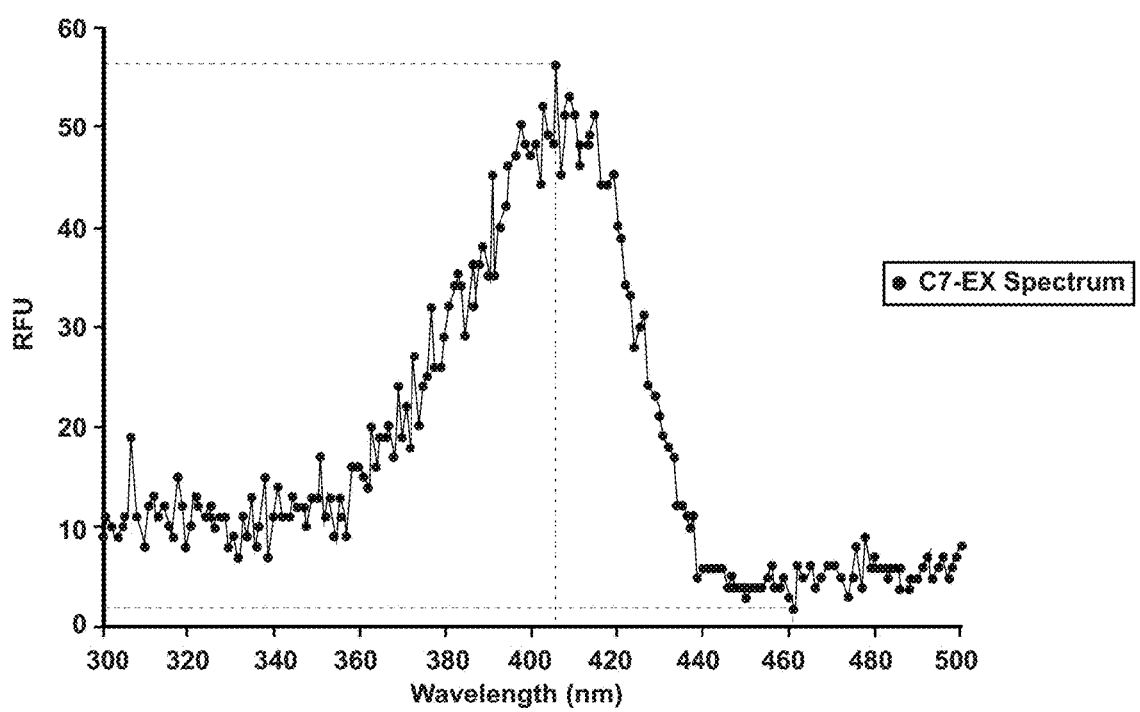
FIG. 5B is a graph showing an excitation spectrum (RFU) for PdTFPP dissolved in chloroform (dried for 10 minutes)
Figure 5C:
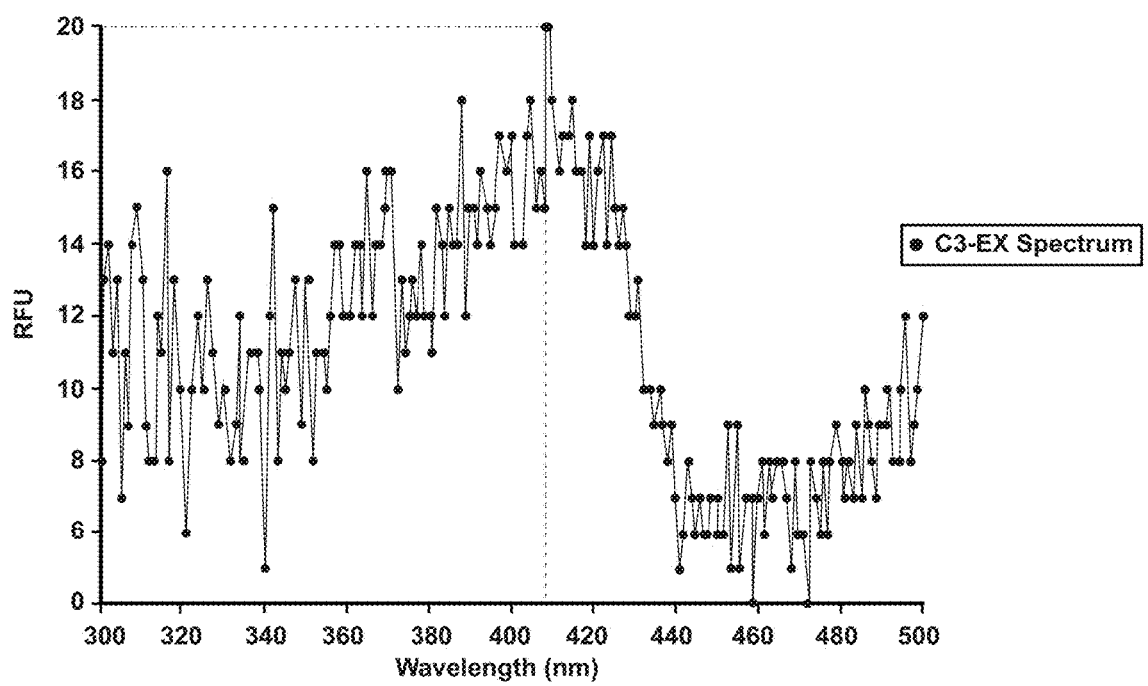
FIG. 5C is a graph showing an excitation spectrum (RFU) for PdTFPP dissolved in heptane.
Figure 5D:
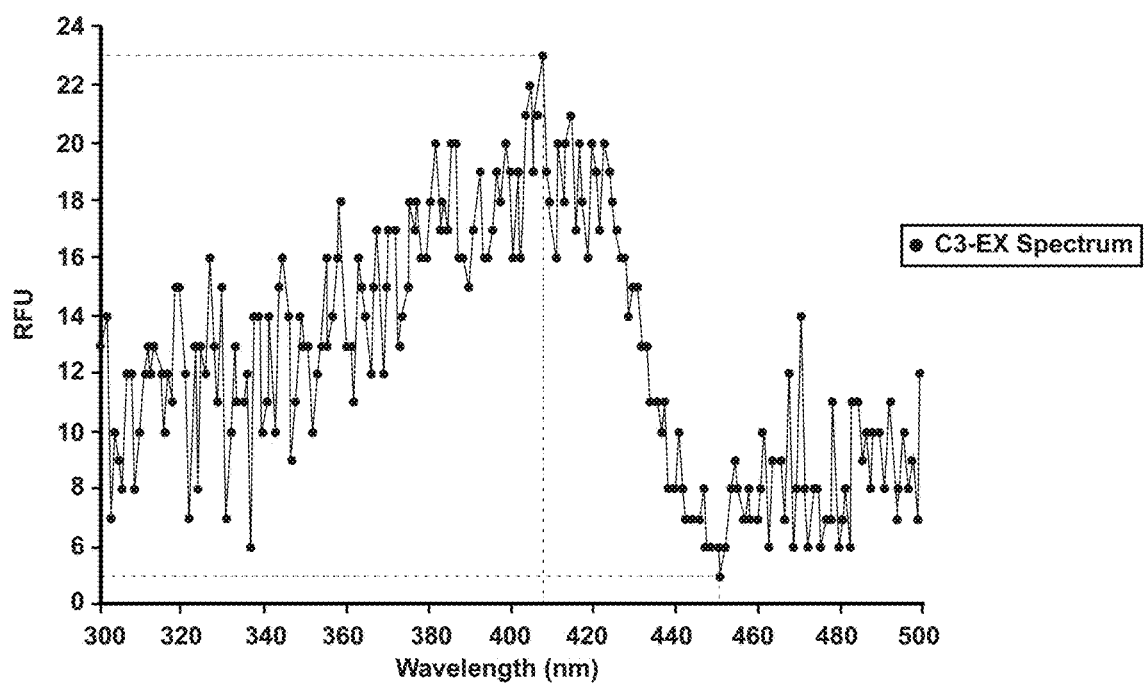
FIG. 5D is a graph showing an excitation spectrum (RFU) for PdTFPP dissolved in heptane (dried for 10 minutes)

Excitation spectra of different oxygen sensing materials were measured first, as shown in FIGS. 5A-D. The x-axis is the wavelength of the excitation light, and the y-axis represents the RFU (relative fluorescence unit). An excitation peak at 407 nm can be detected for PdTFPP dissolved in chloroform (FIGS. 5A-5B). For comparison, PdTFPP was dissolved into two different solvents at the same concentration. FIGS. 5A-5B demonstrate the excitation spectrum for PdTFPP dissolved in chloroform, while FIGS. 5C-5D demonstrate the excitation spectrum for the same concentration of PdTFPP dissolved in heptane. The results of FIGS. 5A-5D demonstrate that a smoother plot was obtained when the PdTFPP was dissolved in chloroform solution. With reference to FIGS. 5B and 5D, an excitation spectrum for PdTFPP dissolved in chloroform and heptane, respectively, and then allowed to dry for 10 minutes is illustrated. The results of FIGS. 5B and 5D demonstrate that the fluorescence of PdTFPP in both chloroform and heptane, respectively, increases, after 10 minutes of evaporation of the solvent. These results demonstrate that the existence of a solvent can affect the photo-property of the sensing material. Thus, in some aspects, to increase the sensitivity and stability of the oxygen sensing film, any solvent that may be present should be removed completely before further fabrication.

Figure 6:
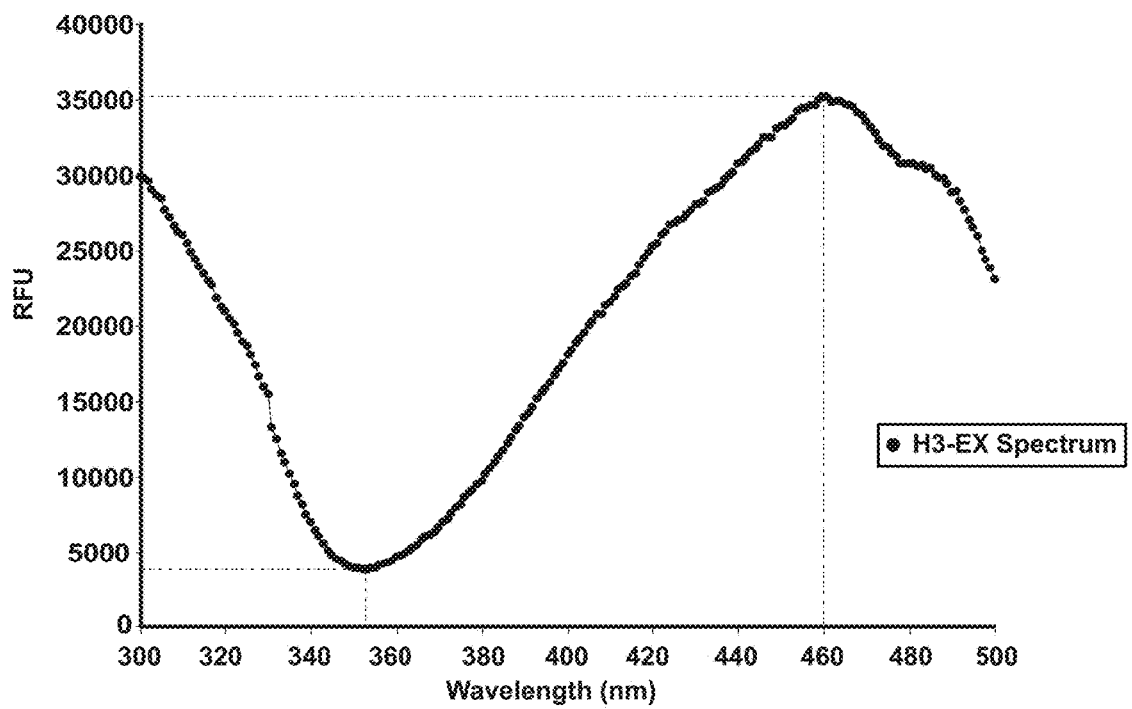
FIG. 6 is a graph showing an excitation spectrum (RFU) for $Ru(dpp)_3Cl_2$ dissolved in chloroform.

With reference to FIG. 6, the excitation spectrum of $Ru(dpp)_3Cl_2$ was also tested. Within the visible light range (390 nm-700 nm), an excitation peak at 460 nm was detected. As compared to PdTFPP, a blue light source can be used for $Ru(dpp)_3Cl_2$ while UV light is required for excitation of PdTFPP. $Ru(dpp)_3Cl_2$ may be preferred for oxygen sensors that are embedded (integrated) with a wound dressing system.

Figure 7:
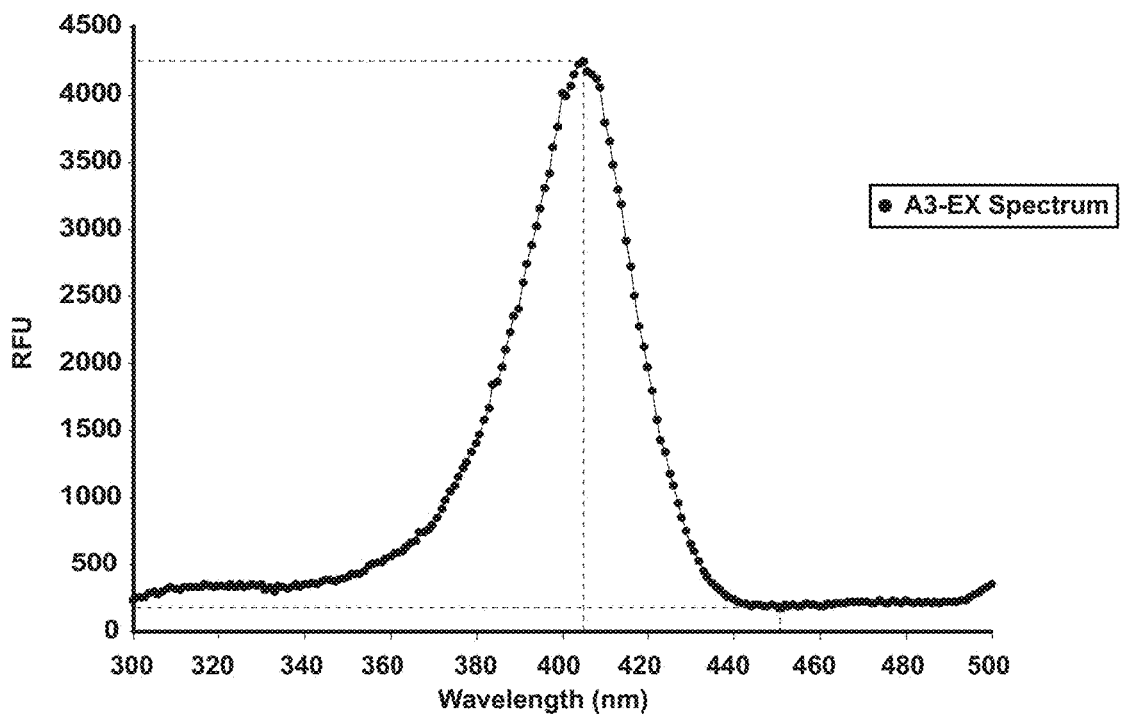
FIG. 7 is a graph showing an excitation spectrum (RFU) of PdTFPP with PS on filter paper.
Figure 8:
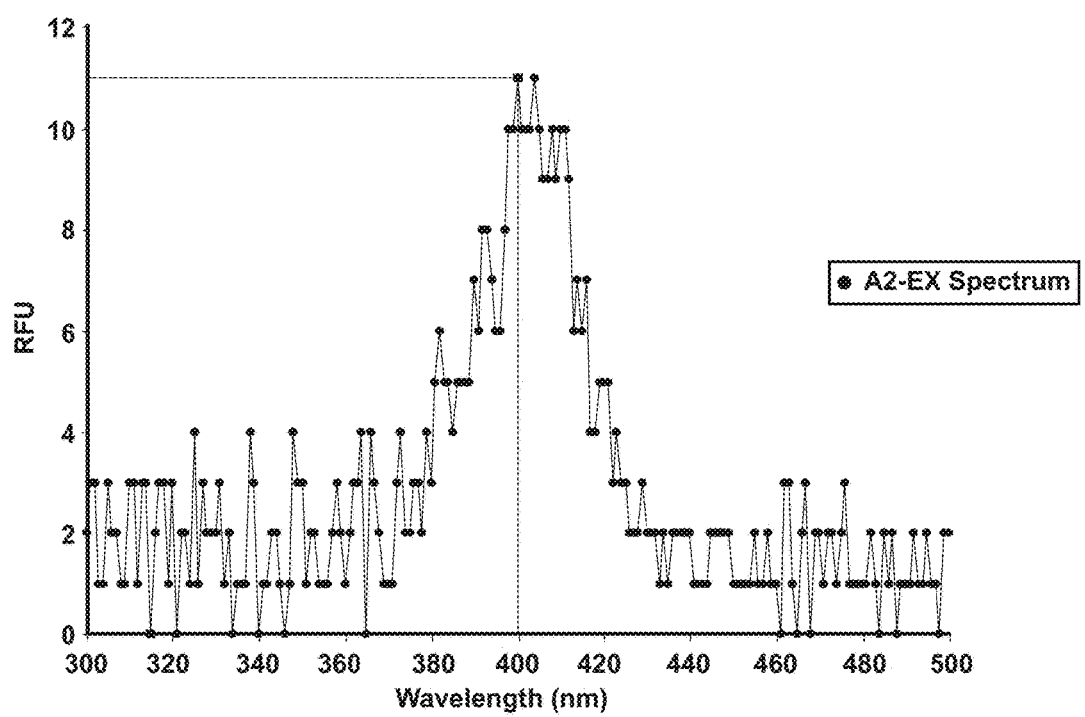
FIG. 8 is a graph showing an excitation spectrum of PdTFPP with PDMS on filter paper.

The excitation spectrum was also measured for PdTFPP deposited on filter paper with PS (poly-styrene) and PDMS, as shown in FIGS. 7 and 8, respectively. A higher peak RFU can be observed with PS. When the PdTFPP was mixed with PDMS, more photo noise was introduced and fluorescent intensity (RFU) at the peak decreased. PS may be able to provide a better photo-stability protection to PdTFPP without compromising the photo characteristic.

Figure 9A:
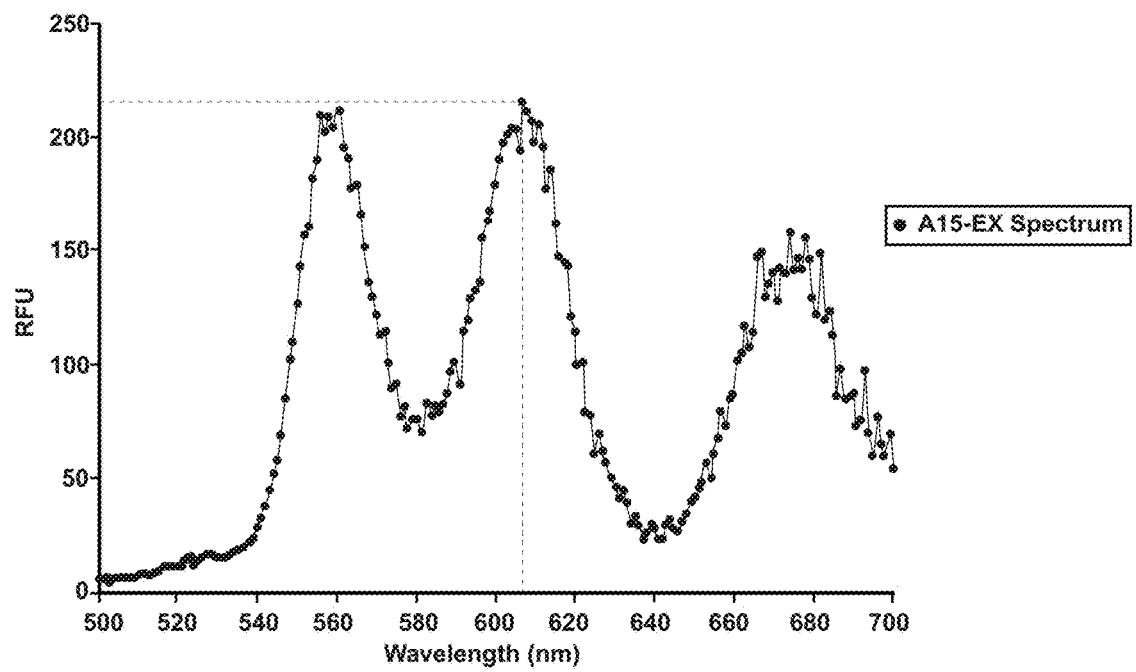
FIG. 9A is a graph showing an emission spectrum for PdTFPP dissolved in chloroform.
Figure 9B:
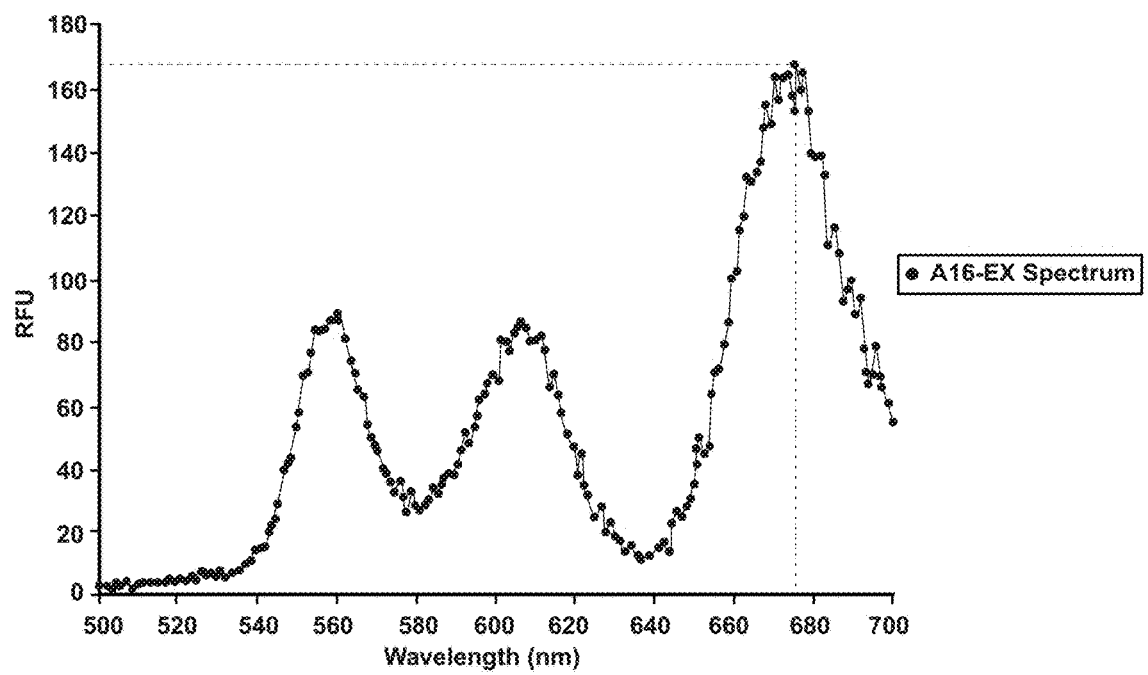
FIG. 9B is a graph showing an emission spectrum for PdTFPP dissolved in chloroform (dried for 10 minutes)
Figure 9C:
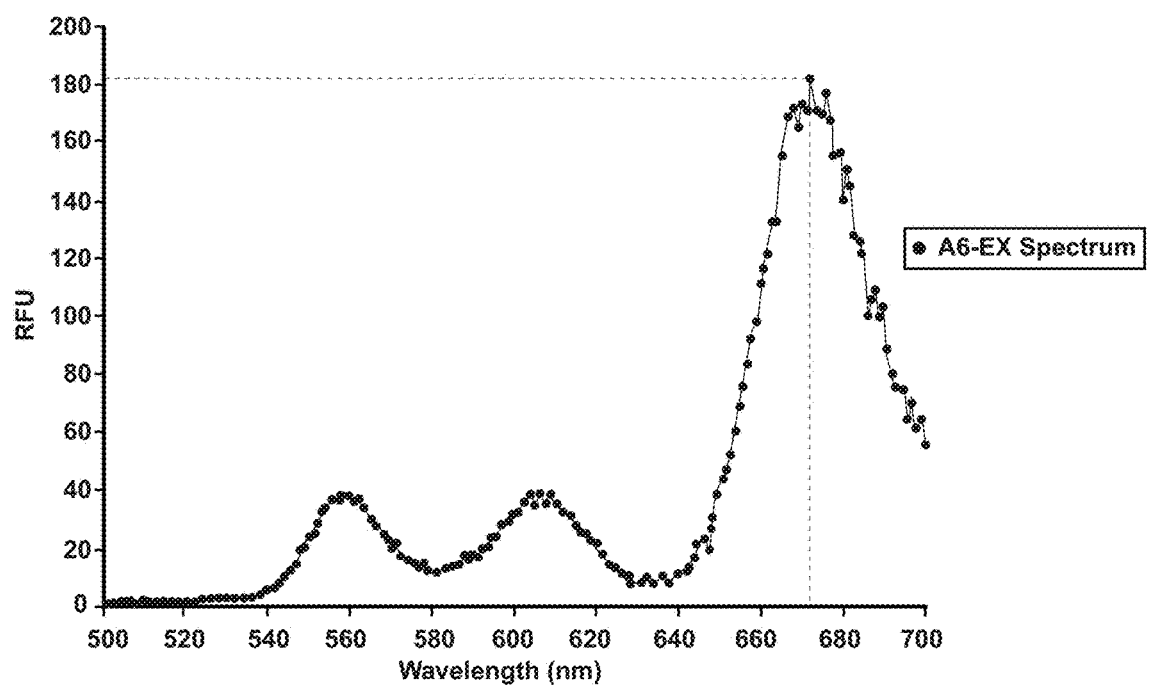
FIG. 9C is a graph showing an emission spectrum for PdTFPP dissolved in chloroform (dried for 30 minutes)
Figure 10:
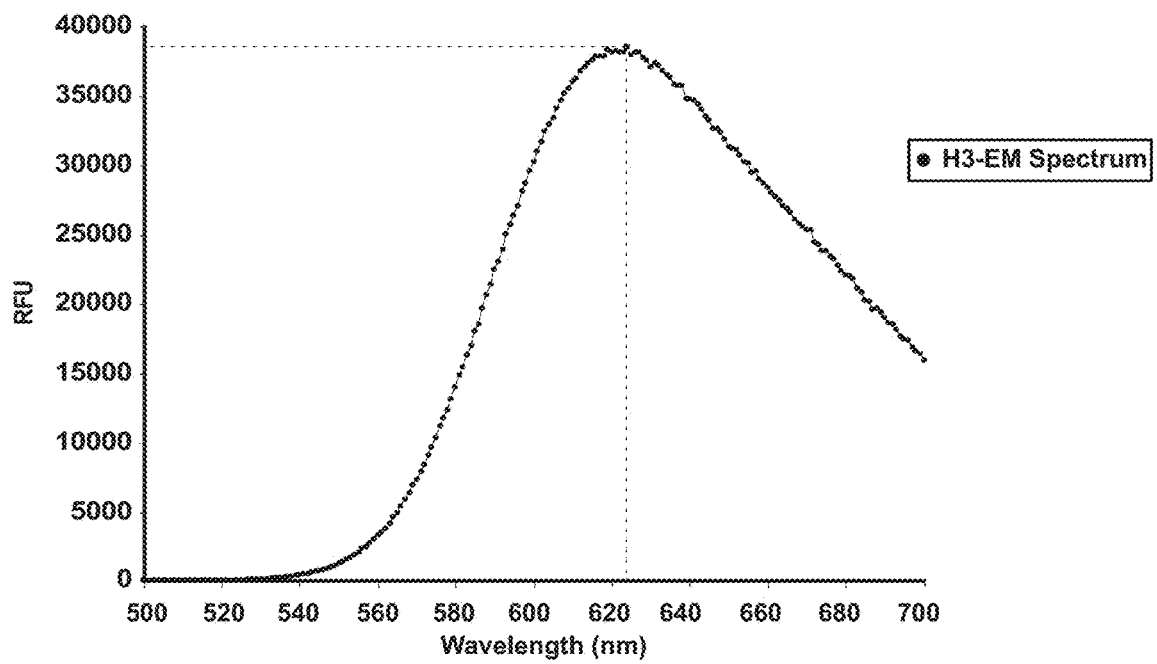
FIG. 10 is a graph showing an emission spectrum of $Ru(dpp)_3Cl_2$ dissolved in chloroform.
Figure 11:
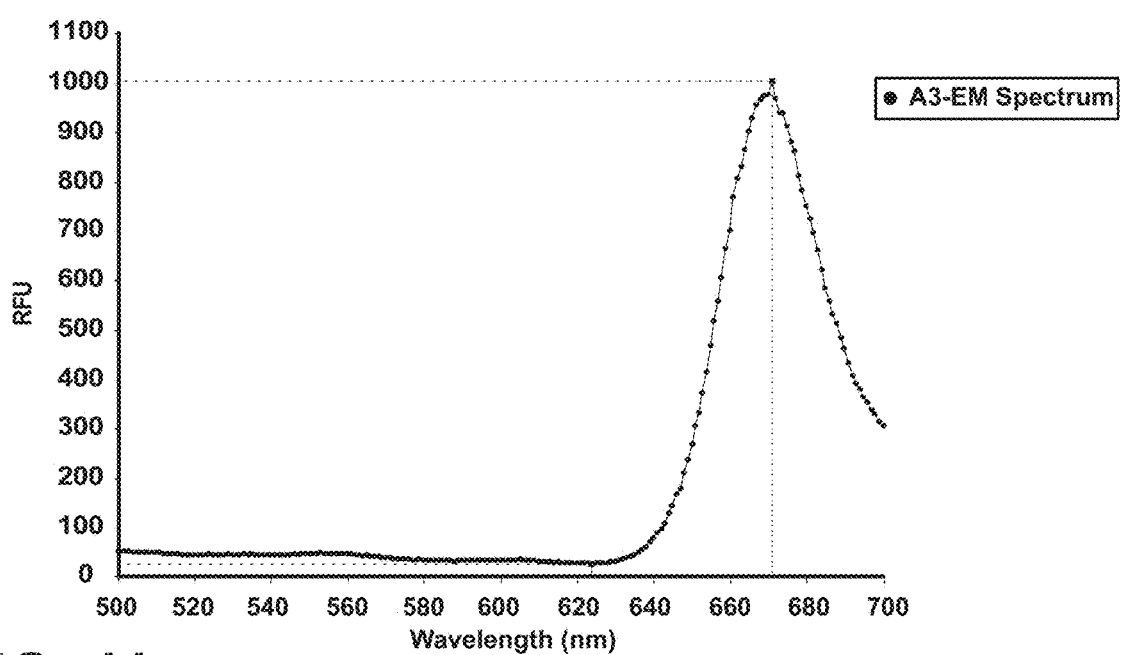
FIG. 11 is a graph showing an emission spectrum of PdTFPP with PS on filter paper.
Figure 12:
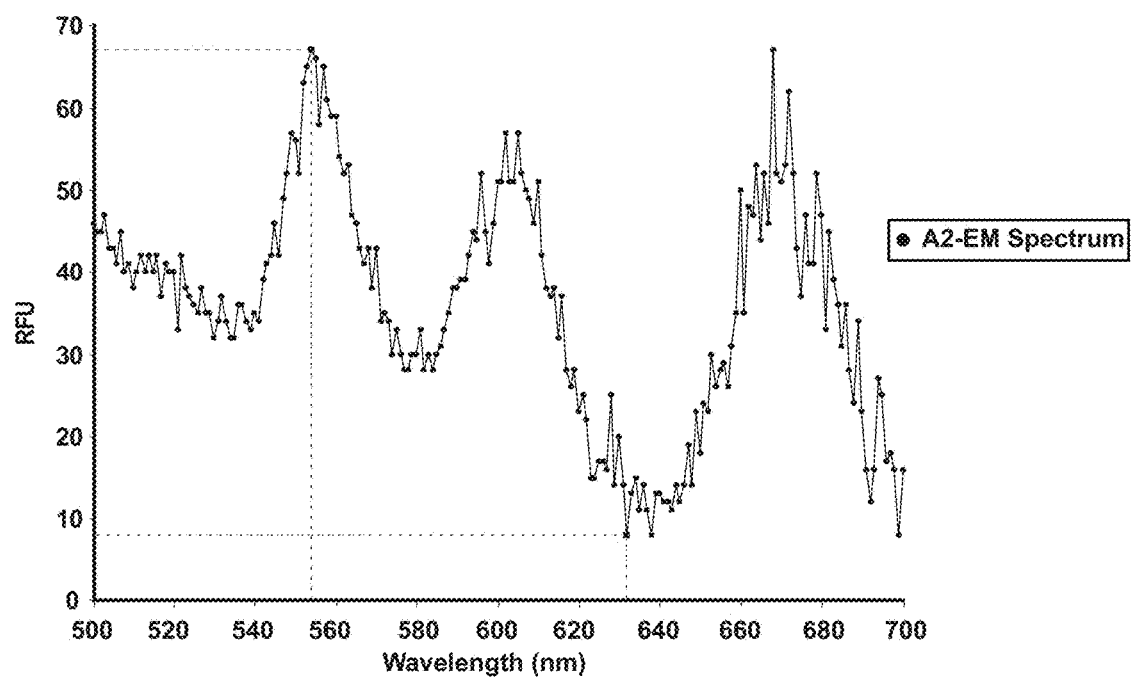
FIG. 12 is a graph showing an emission spectrum of PdTFPP with PDMS on filter paper.

Emission characterization was then conducted. When dissolved with chloroform, PdTFPP has three emission peaks. FIG. 9A illustrates the emission spectrum of PdTFPP in chloroform. FIGS. 9B and 9C illustrate the emission spectrum for the same concentration of PdTFPP in chloroform after 10 minutes and 30 minutes of drying, respectively. With reference to FIGS. 9A-C, a peak at 675 nm remains while solvent is being evaporated. Thus, the effect of solvent on the fluorescent material can be again confirmed from the emission profile. With reference to FIG. 10, the photo property of dissolved $Ru(dpp)_3Cl_2$ in chloroform was not affected by the solvent. A clear peak is illustrated at 625 nm. FIGS. 11 and 12 compare the emission profile of PdTFPP deposited with PS and PDMS, respectively. The same trend was observed as the sample with PDMS had three emission peaks, which is not expected for oxygen sensing.

Figure 13A:
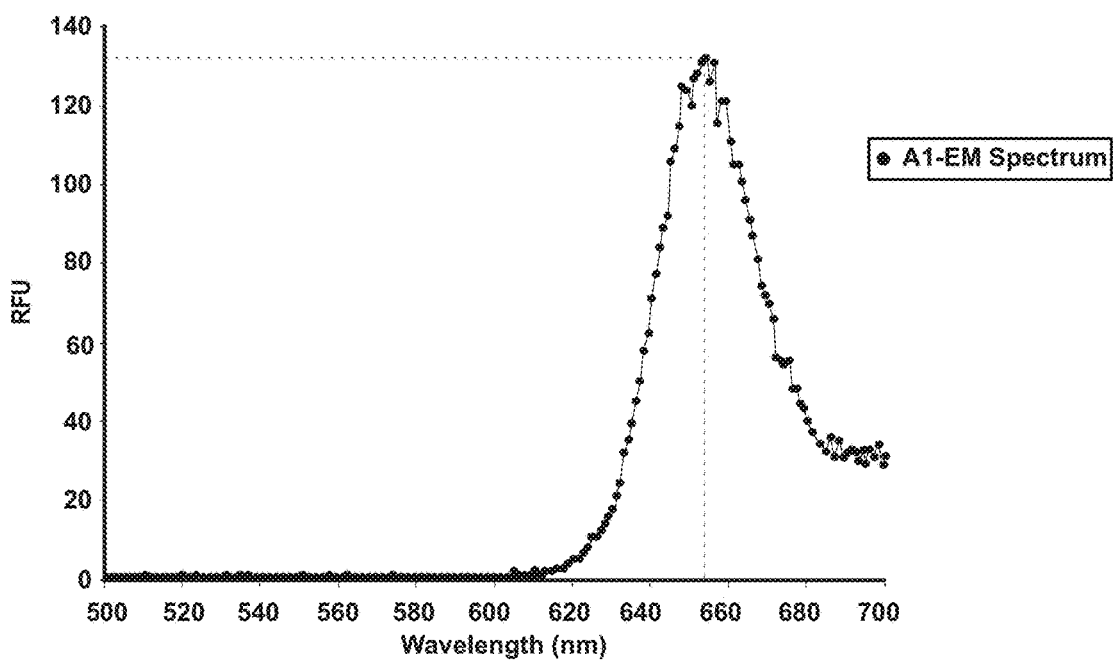
FIG. 13A is a graph showing the emission spectrum of a RedEye® patch in water with 0% dissolved oxygen concentration.
Figure 13B:
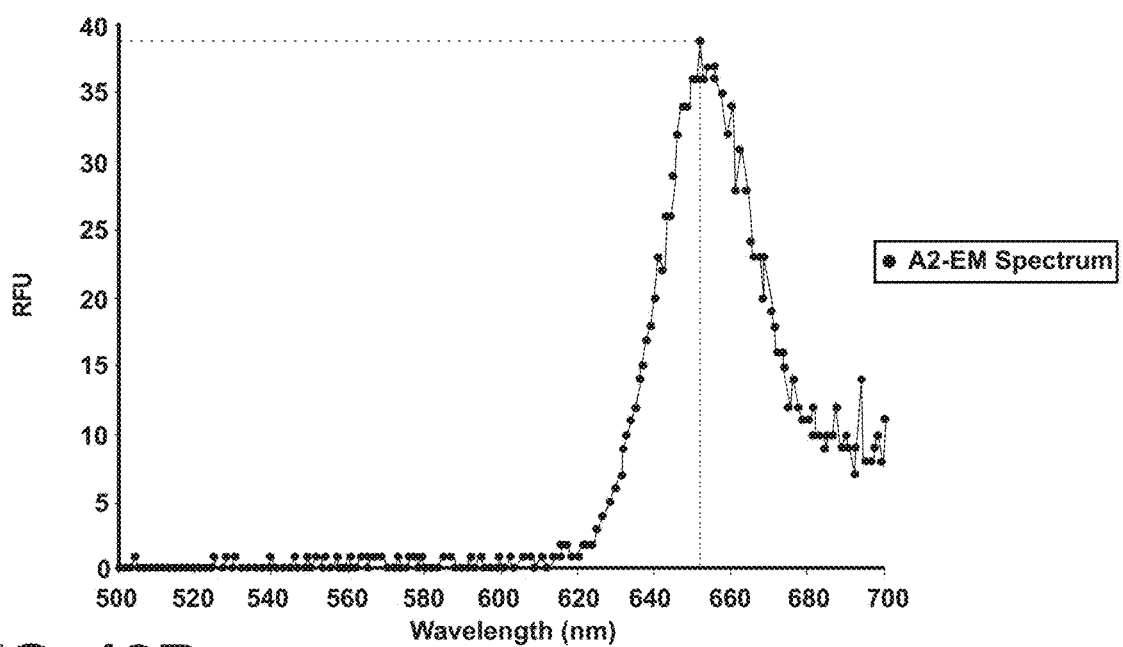
FIG. 13B is a graph showing the emission spectrum of a RedEye® patch in water with 20% dissolved oxygen concentration.
Figure 14A:
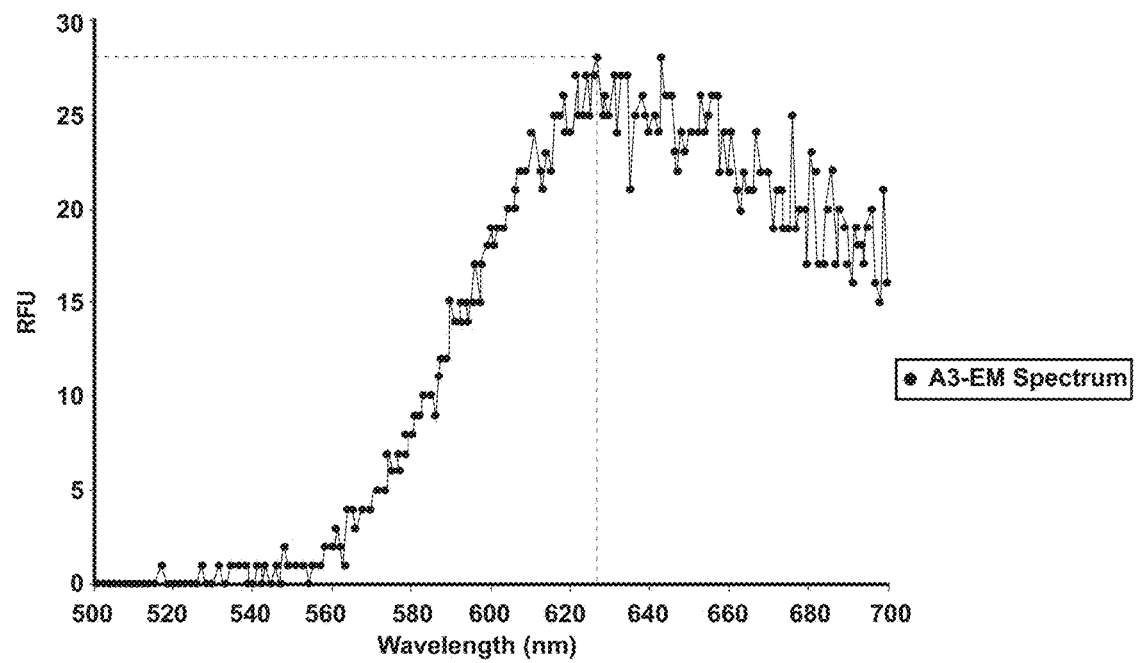
FIG. 14A is a graph showing an emission spectrum of PDMS encapsulated $Ru(dpp)_3Cl_2$ in water with a dissolved oxygen concentration of 0%.
Figure 14B:
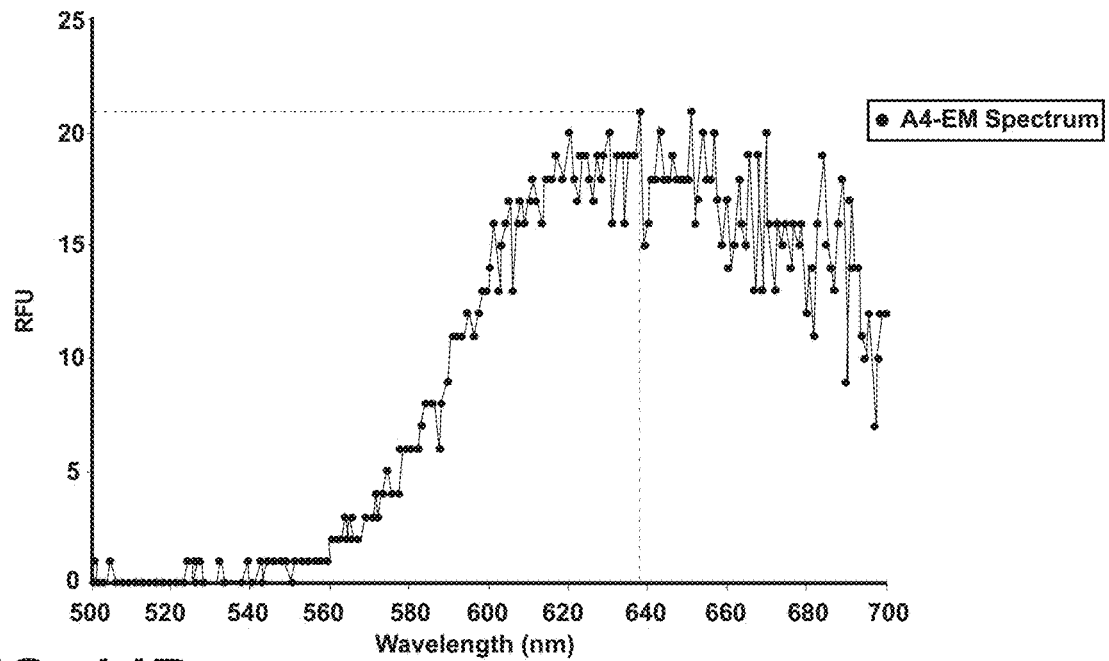
FIG. 14B is a graph showing the emission spectrum of PDMS encapsulated Ru(dpp)$_3$Cl$_2$ in water with a dissolved oxygen concentration of 20%.

Emission intensity under different oxygen levels was also tested using the same experiment setup. For comparison, RedEye®, an oxygen indicator commercially available from Ocean Optics, was tested. PDMS encapsulated $Ru(dpp)_3Cl_2$ and PS encapsulated PdTFPP were also tested. The results are shown in FIGS. 13A-B and 14A-B. FIGS. 13A and 13B illustrate the emission spectrum of a RedEye® patch in water with 0% and 20% dissolved oxygen concentration, respectively. FIGS. 14A and 14B illustrate the emission spectrum of PDMS encapsulated $Ru(dpp)_3Cl_2$ in water with a dissolved oxygen concentration of 0% and 20%, respectively. A fluorescent intensity decrease of 3.38 times was obtained from the commercial RedEye® patch in the presence of dissolved oxygen. For $Ru(dpp)_3Cl_2$ and PdTFPP (not shown), a decrease of 1.4 times and 2.79 times, respectively, was measured under various oxygenated environments. The emission intensity decreases with an increase of the oxygen concentration in water from 0% to 20%.

In order to protect the functionality of the sensing materials during sterilization, the photo properties of different retrieved samples were measured after a sterilization process ($H_2O_2$ vapor treatment), as shown in Table 1. $Ru(dpp)_3Cl_2$ was shown to be more vulnerable to the $H_2O_2$ vapor treatment under test conditions and PS may be needed for protection. PdTFPP was shown to be more stable as compared to $Ru(dpp)_3Cl_2$; however, a decrease of the photo-reaction intensity can be observed after sterilization when no polymer binder was added.

TABLE 1

Effect of Sterilization Process on Emission Peak.

| Test Sample | Before Sterilization | After Sterilization |
| --- | --- | --- |
| $Ru(dpp)_3Cl_2$ in filter paper | Emission peak detected | No emission peak detected |
| $Ru(dpp)_3Cl_2$ + PDMS | Weak emission peak detected, slightly oxygen-sensitive | No emission peak detected |
| $Ru(dpp)_3Cl_2$ + PS | Emission peak detected | Emission peak detected, oxygen-sensitive |
| PdTFPP in filter paper | Emission peak detected | Weak emission peak, slightly oxygen-sensitive |
| PdTFPP + PDMS | Weak emission peak detected | Emission peak detected, slightly oxygen-sensitive |
| PdTFPP + PS | Emission peak detected, oxygen-sensitive | Emission peak detected, oxygen-sensitive |

Figure 15A:
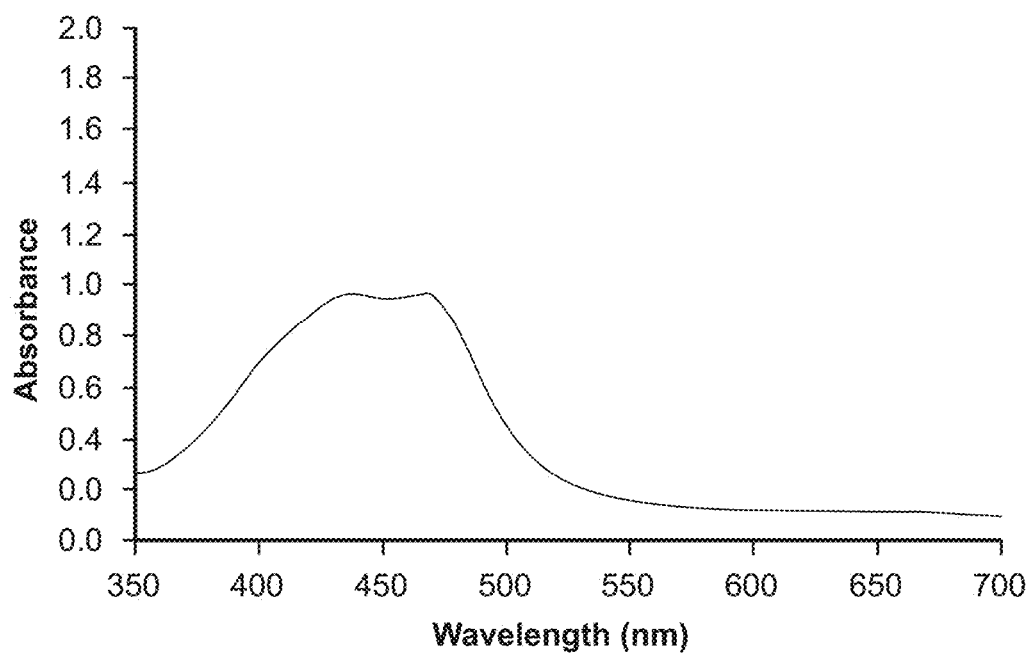
FIG. 15A is a plot of absorbance as a function of wavelength for an oxygen-sensitive ink system including Ru(dpp)$_3$Cl$_2$ as the dye, ethyl cellulose as the polymer binder, and ethanol as the solvent.
Figure 15B:
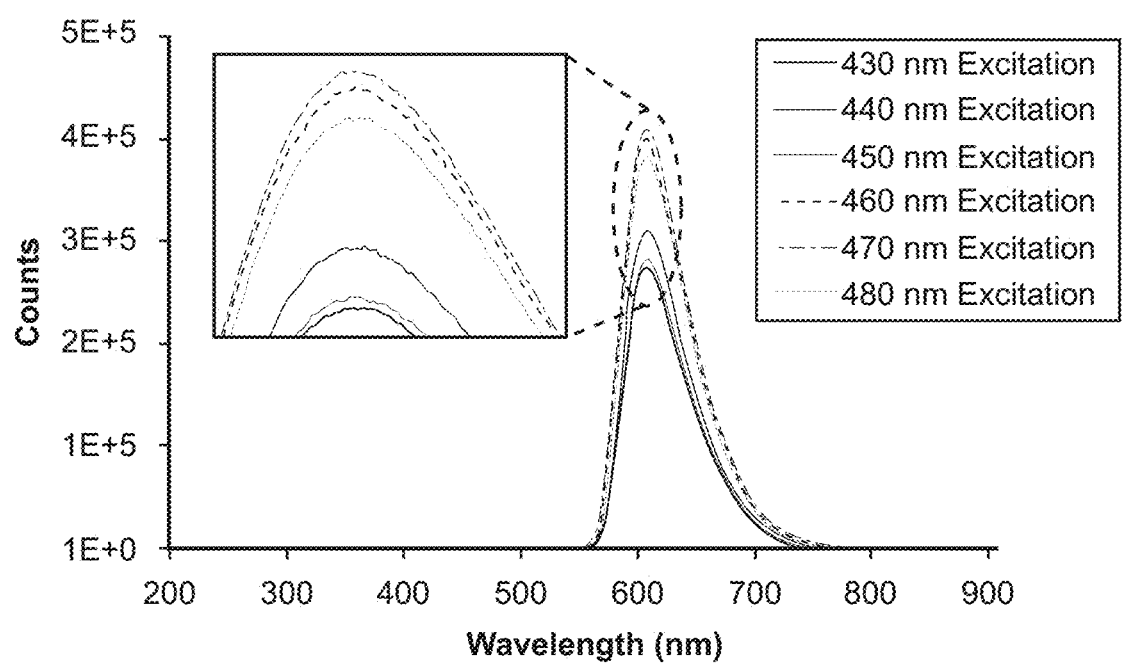
FIG. 15B is a plot of fluorescence emission spectra for the oxygen-sensitive ink system of FIG. 15A.

The excitation wavelength for an oxygen sensitive ink system including $Ru(dpp_3)Cl_2$ as the dye, ethyl cellulose as the polymer binder, and ethanol as the solvent ("$Ru(dpp_3)Cl_2$+ethyl cellulose+ethanol") was determined by obtaining an absorption spectrum and determining the wavelength(s) of maximum absorption. FIG. 15A illustrates a plot of absorbance as a function of wavelength determined using a Cary50 UV-visible absorbance spectrometer. A maximum absorbance was observed between the wavelengths of about 430 nm to about 480 nm. The wavelengths of maximum absorbance were then used as excitation wavelengths in obtaining fluorescence spectra for the oxygen sensitive ink system ($Ru(dpp_3)Cl_2$+ethyl cellulose+ethanol). Fluorescence spectra were obtained for the sample using excitation wavelengths ranging from 430 nm to 480 nm, in 10 nm increments, using an FLS920 fluorescence spectrometer from Edinburgh Instruments. The fluorescence spectra are shown in FIG. 15B. FIG. 15B shows a maximum fluorescence intensity at a wavelength of 600 nm for an excitation wavelength of 470 nm. Thus, the absorbance and fluorescence spectra can be utilized to determine a suitable excitation and fluorescence emission wavelength for an oxygen sensitive ink system of the present disclosure. The exemplary $Ru(dpp_3)Cl_2$+ethyl cellulose+ethanol system exhibited a maximum fluorescence at 600 nm for an excitation wavelength of 470 nm.

Printing techniques for the manufacturing of electronics on flexible substrates have been developed. Printing methods that have been investigated for the direct printing of electronics include, but are not limited to, inkjet, flexographic, screen and rotogravure printing.

An oxygen detection sensor according to one aspect of the present disclosure may be fabricated using an inkjet printing process. In inkjet printing, precise control of ink interactions at the substrate surface may depend on the ink formulation and substrate morphology. Typically, in inkjet printing, the viscosity of the ink should be below about 10 centipose (cP) to properly jet the ink from the nozzles of the cartridge. In printed electronics, various applications may require substrates with different surface properties.

Four different substrate materials were tested for oxygen generation. These materials included: unrastered parchment paper, laser rastered parchment paper, unrastered Tyvek® paper, and laser rastered Tyvek® paper. For the preparation of ink, Tris(4,7-diphenyl-1,10-phenanthroline)ruthenium(II) dichloride dye, ethanol (ACS spectrophotometric grade) solvent, and polymer binders, such as polystyrene (38% emulsified in $H_2O$) and polydimethylsiloxane (PDMS) were used. Tyvek® is a commercially available example of a polyethylene-based fiber material suitable for use with aspects of the present disclosure.

Substrate characteristics such as roughness and thickness were measured using a Bruker ContourGT-K interferometer. The average thickness of the unrastered parchment, rastered parchment, unrastered Tyvek®, and rastered Tyvek® substrates were measured to be 73.8±2.2 μm, 73.3±1.1 μm, 206.2±4.2 μm, and 208.8±6.3 μm, respectively. The root mean square (RMS) roughness of the unrastered parchment, rastered parchment, unrastered Tyvek®, and rastered Tyvek® substrates were measured to be 7.0±0.5 μm, 6.5±0.4 μm, 5.1±0.1 μm, and 4.6±0.4 μm, respectively. From the measured values, it is understood that thickness of the substrates was not significantly impacted by laser rastering. The roughness of the rastered Tyvek® paper substrate was decreased by 10.9% when compared to the unrastered Tyvek® paper. Similarly, the roughness of the rastered parchment paper substrate was decreased by 7.8% when compared to the unrastered parchment paper.

Two test ink solutions were prepared for testing, including:

1. Dye+Ethanol+Polystyrene (1:100:1, by mass)–0.3 g of dye and 0.3 g of polystyrene were mixed with 30 g (40 ml) of ethanol solvent.
2. Dye+Ethanol+PDMS (1:100:1, by mass)–0.3 g of dye and 0.3 g of PDMS were mixed with 30 g (40 ml) of ethanol solvent.

Both test ink solutions were mixed on a hotplate with magnetic stirrer at 525 rpm; overnight (12 hours) under a fume hood to obtain homogenous ink solutions.

The Z-number is a dimensionless constant, and a measure of density, surface tension, and viscosity. For proper jetting of ink during inkjet printing, the Z-number should be in the range of about 2 to about 10. The formula for Z is:

$$Z = \frac{Re}{We} = (d\rho\gamma)^{\frac{1}{2}}/\eta$$

Where:
d is the nozzle diameter (21.5 µm, in the current example),
ρ is the liquid density,
γ is the surface tension and
η is the ink viscosity.

Inks with viscosity less than 10 cP are typically preferred for inkjet printing. For the dye+ethanol+polystyrene-based test ink solution (solution #1), the surface tension was measured using the FTA200 and is 21.95±0.1 dynes/cm. The measured density of ink solution #1 was 0.766 g/ml.

To determine the viscous behavior of ink solution #1 under a broad range of temperatures from 20° C. to 60° C., a rheometer was used. The shear rate was maintained at 1000 (1/s) and the viscosity was decreased from 3.77 cP to 2.11 cP for the temperature range of 20° C. to 60° C. After substituting the measured values, Z-numbers ranging from 5 to 9 were calculated as the temperature increased from 20° C. to 60° C. The test results show that ink solution #1 is suitable for inkjet printing at room temperature.

For the dye+ethanol+PDMS-based ink solution (solution #2), the measured surface tension was 21.81±0.08 dynes/cm. The measured density of ink solution #2 was 0.7669 g/ml. For the shear rate of 1000 (1/s), viscosity decreased from 3.76 cP to 2.10 cP for the temperature range of 20° C. to 60° C. The calculated Z-number for ink solution #2 increased from 5 to 9 as the temperature increased from 20° C. to 60° C. Based on these test results, it is evident that ink solution #2 is also suitable for inkjet printing at room temperature.

The Z-number and other characteristics such as viscosity, density, and surface tension for both ink solutions are similar. Without being limited by theory, this may be because the effect of very small quantities of polymers, polystyrene, and PDMS in the ink solutions is negligible.

The contact angle was measured for ink solution #1 on the four substrate materials (unrastered parchment paper, laser rastered parchment paper, unrastered Tyvek® paper, and laser rastered Tyvek® paper) using an FTA 200 instrument. The measured contact values of the ink drops on the unrastered parchment paper, rastered parchment paper, unrastered Tyvek® paper, and rastered Tyvek® paper substrates were 20.7±0.1 degrees, 35.3±0.5, 13.2±0.7 degrees, and 12.4±0.1 degrees, respectively. While measuring contact angles with the FTA200 instrument, it was observed that the ink drops were spreading rapidly on both the unrastered and rastered Tyvek® substrates. Even though it is evident from the contact values that all the substrates possess good wetting characteristics, the tested Tyvek® substrates may not be suitable for printing due to rapid spreading of ink on the surface. Thus, surface modifications of Tyvek® substrates may be required. For example, plasma or UV treatment may be utilized to alter the surface properties (to increase contact angle) of Tyvek® materials so that spreading of ink on the surface can be controlled prior to curing of the ink.

An oxygen sensing and electronic interfacing system (bandage) according to the present disclosure can be used to measure and maintain a suitable amount of oxygen at the interface of the wound and the bandage. In short, the smart dressing 1 of the present disclosure can measure the amount of oxygen present, and supply more oxygen as necessary.

Referring again to FIG. 1, Smart Dressing 1 can include an optical oxygen sensing module 20 with a signal-processing circuit to monitor the amount of oxygen present. A ruthenium-based dye may be utilized as the oxygen-dependent (sensing) compound. Similar to other dyes, when the ruthenium dye is excited by a blue LED, it produces an orange fluorescence. The fluorescence signal is dependent on the amount of oxygen present. In contrast to hypoxic conditions, it is known that when oxygen is present, fluorescence is less intense and decays more quickly. By characterizing the fluorescence, the amount of oxygen present can be quantified (measured). One method to quantify oxygen is to excite the dye until it reaches a steady state, then directly measure the peak intensity as well as the time it takes to decay. However, this method is sensitive to the precise positioning of the LED source, the amount of background light present, and photo-bleaching of the dye over time. To avoid these issues, a system according to one aspect of the present disclosure modulates the excitation blue LED at a frequency between 20 kHz and 75 kHz. The phase difference between blue excitation and the resulting orange fluorescence signal can be measured. This phase difference changes with the amount of oxygen present.

A DC bias to an excitation source (blue LED) may be provided to turn it on. An AC signal may then be superimposed to modulate the intensity of the blue LED. The resulting fluorescence signal has a phase shift that increases with the amount of oxygen present. The fluorescence signal may be amplified and processed so that its phase can be compared with the excitation signal. This phase shift is an indicator (measurement) of the amount of oxygen present.

Phase detection may be accomplished with digital logic by using a single exclusive (XOR) gate. When the XOR gate receives two in-phase signals, its output is low (0 volts DC). When the XOR gate receives two completely out-of-phase signals, its output is high (e.g. 4.5 V DC). When the signals are slightly out-of-phase, the output of the XOR gate is high for a short time, and then low for the rest of the cycle. The assertion time (pulse width) for one cycle of the XOR gate's output increases as the input signals move more out-of-phase. The output of the XOR gate may be low-pass-filtered to produce a DC output that corresponds to the phase of its inputs.

Figure 16:
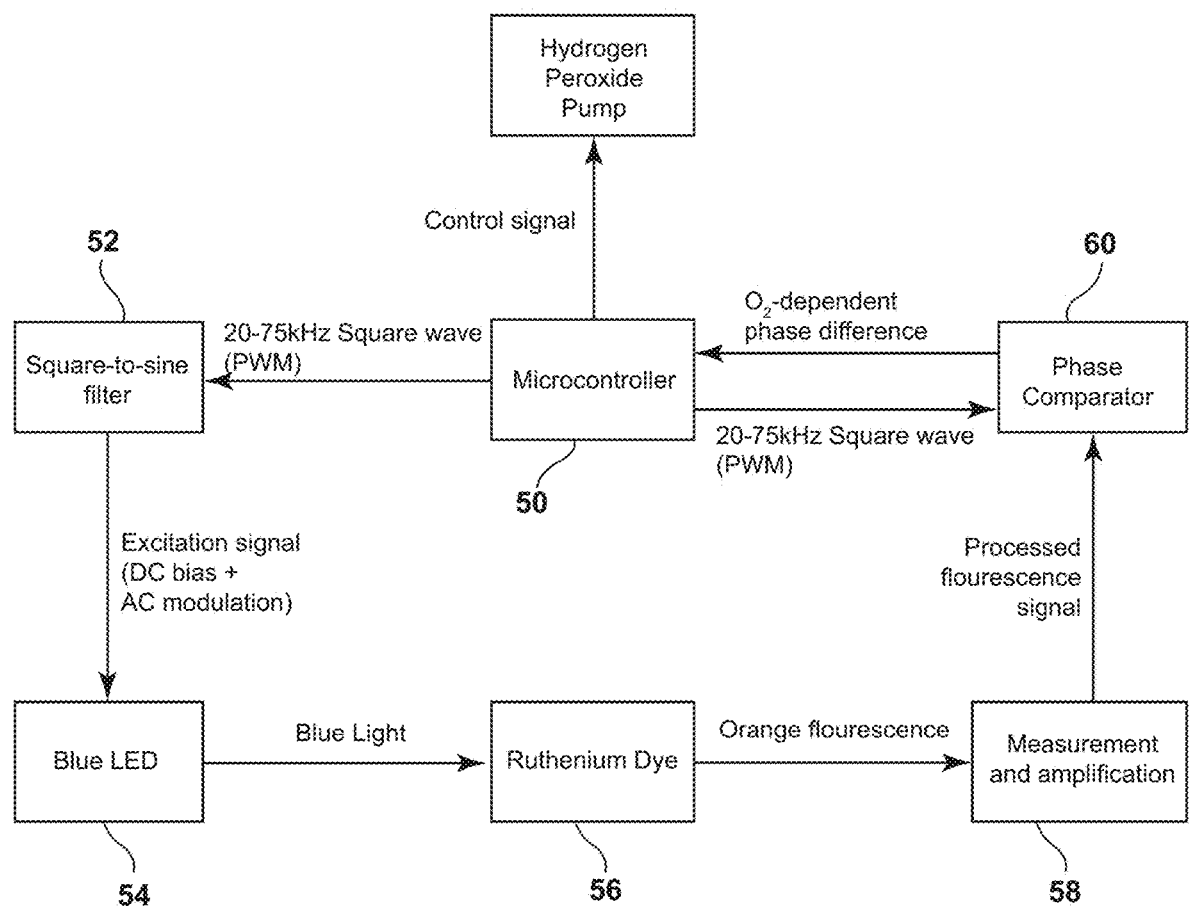
FIG. 16 is a schematic diagram of an oxygen sensor and electronic interfacing circuitry.

Referring now to FIG. 16, signal generation, measurement, and decision making may be mediated by a microcontroller 50. The microcontroller 50 generates a square wave at a specified frequency, which is converted to a DC-biased sine wave by a filter 52. The DC-biased sine wave from filter 52 drives a blue LED 54, so that blue light from the LED 54 excites the ruthenium dye 56. The excited ruthenium dye 56 fluoresces, and the sinusoidal fluorescence (orange) is measured with a highly sensitive photodiode 58. The photodiode 58 includes a light filter so that it picks up only the orange fluorescence of the dye 56, and not the blue LED's emission. A processed fluorescence signal is sent from the photodiode 58 to a phase comparator (detector) 60. Because the phase comparator 60 requires square wave inputs, the sinusoidal fluorescence signal is converted to a square wave by a comparator circuit. After the fluorescence signal is converted, its output is sent to the phase comparator 60.

Finally, the microcontroller 50 receives a DC input from the phase comparator 60 that represents the current oxygen present. The microcontroller 50 then decides whether or not to pump hydrogen peroxide to generate more oxygen.

As discussed above, untreated Tyvek® is generally not suitable for printing. Therefore, the surface properties of the Tyvek® substrate may be altered by treating its surface with a fusion UV system. Typically, UV treatment raises the surface energy of a substrate through oxidation which in turn increases the polar energy, potentially providing improved wetting. For test purposes, unrastered and rastered Tyvek® substrates were UV treated 1 to 4 times. The contact angle of the ink drops on the substrates were then measured (Table 2).

The contact angle of the unrastered and rastered Tyvek® substrate before UV treatment was measured as 13.2±0.7 degrees and 12.4±0.1 degrees, respectively. The contact angles of the unrastered Tyvek® substrates that were UV treated for 1 time, 2 times, 3 times, and 4 times were measured as 14.8±0.1 degrees, 13.4±1.1 degrees, 12.4±1.1 degrees, and 12.7±1.6 degrees, respectively. Similarly, the contact angles of the rastered Tyvek® substrates that were UV treated for 1 time, 2 times, 3 times, and 4 times were 10.5±1.1 degrees, 13.8±1.0 degrees, 14±1.4 degrees, and 12.1±0.6 degrees, respectively.

TABLE 2

Contact angles of the UV treated Tyvek® substrates.

| Tyvek Substrate | Contact angle before UV Treatment (degrees) | No. of times substrate treated | Contact angle after UV treatment (degrees) |
| --- | --- | --- | --- |
| Unrastered | 13.2 ± 0.7 | 1 | 14.8 ± 0.1 |
|  |  | 2 | 13.4 ± 1.1 |
|  |  | 3 | 12.4 ± 1.1 |
|  |  | 4 | 12.7 ± 1.6 |
| Rastered | 12.4 ± 0.1 | 1 | 10.5 ± 1.1 |
|  |  | 2 | 13.8 ± 1.0 |
|  |  | 3 | 14.0 ± 1.4 |
|  |  | 4 | 12.1 ± 0.6 |

From the measured contact angles and through the live video option (spreading and absorbing behavior of the drops on the substrate can be seen) in the FTA 200 software, it was concluded that the impact of the UV treatment on the surface of the Tyvek® substrates is minimal.

It was observed from measured values that the roughness of parchment paper samples was not consistent. In order to obtain a similar smoothness over the surface of parchment paper, a calendering process was employed. A calendering machine was used to calendar both sides of the parchment paper, with an applied pressure of 35 psi (241 kPa). It was observed that, due to calendering, the roughness of the parchment paper was reduced from 8.7±1.7 μm to 5.5±0.4 μm.

During testing, multi-layer samples (5 layer, 3 layer, and 1 layer) of ruthenium dye-based ink, with ethanol as solvent and PDMS as binder, was inkjet printed onto both unrastered and rastered parchment paper in an array of circular spots with a diameter of 5 mm with 20 μm drop spacing, using a DIMATIX inkjet printer (DMP 2831). The ruthenium ink with polystyrene as a polymer binder could not be inkjet printed with the DIMATIX inkjet printer because of its comparatively large particle size (<500 nm). The ruthenium ink with PDMS was loaded into a DIMATIX DMC-11610 cartridge (10 pl) through a 25 mm disposable Whatman syringe filter, with a poly vinylidene difluoride filter (PVDF) filter membrane of 0.2 μm pore size, to filter any large particles that may have agglomerated in order to achieve smooth printing. Each layer of the printed ink was cured on the stage of the inkjet printer for 5 minutes at 60° C. A 27 V actuation voltage was applied at 5 kHz firing frequency.

Roughness and thickness measurements were performed to characterize the print quality of the printed 5, 3, and 1 layer samples (see Table 3 below). The root mean square (RMS) roughness of the 5 layer, 3 layer, and 1 layer printed sample was measured to be 6.0±0.03 μm, 6.4±0.48 μm, and 6.7±0.44 μm, respectively, for the unrastered parchment paper. Similarly, a roughness of 6.0±0.42 μm, 6.2±0.31 μm, and 6.8±0.29 μm was measured for the 5 layer, 3 layer, and 1 layer printed samples, respectively, for the rastered parchment paper. Before printing, the roughness of the unrastered and rastered parchment paper substrates were measured to be 7.0±0.5 μm and 6.5±0.40 μm, respectively. From the measured roughness values, it is thus understood that the thickness of the substrates could not be measured because the printed ink did not cover the entire roughness of the substrates (inkjet printing provides a layer that is about 0.5 μm thick).

TABLE 3

Roughness measurement of the inkjet printed ruthenium dye-based ink.

| Substrate | Roughness Before Printing (μm) | No. of Layers | Roughness After Printing (μm) |
| --- | --- | --- | --- |
| Unrastered Parchment Paper | 7.0 ± 0.5 | 5 | 6.0 ± 0.03 |
|  |  | 3 | 6.4 ± 0.48 |
|  |  | 1 | 6.7 ± 0.44 |
| Rastered Parchment Paper | 6.5 ± 0.40 | 5 | 6.0 ± 0.42 |
|  |  | 3 | 6.2 ± 0.31 |
|  |  | 1 | 6.8 ± 0.29 |

Figure 17:
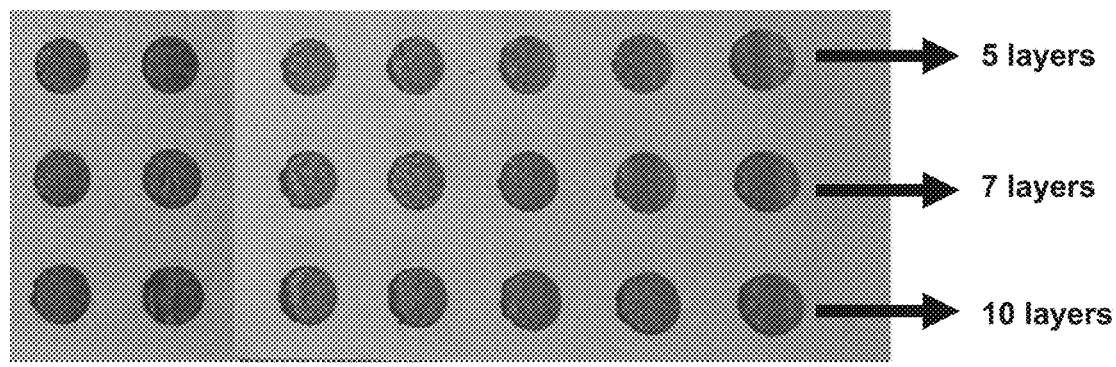
FIG. 17 is a schematic view of an inkjet-printed oxygen-sensitive dye with 7.5 mm diameter circular spot size.

After initial tests for oxygen sensing, the circular spot size was increased to 7.5 mm to increase the concentration of dye. With reference to FIG. 17, an array of circular spots was inkjet printed (10 layer, 7 layer, and 5 layer) on the unrastered parchment paper with 10 μm drop spacing and cured at 45° C.

From the printed samples, it was observed that thermally cured ruthenium particles were falling off the parchment paper. This was due to poor adhesion between the ink and the parchment paper substrate. If the surface energy of the substrate is higher than the surface tension of the ink, for example by at least 10 dynes/cm, then the ink should bind/adhere well to the substrate. The surface energy of the calendered parchment paper was measured with the FTA 200 using the Owens-Wendt method and was calculated as 21.99 dynes/cm. The surface tension of the ruthenium based ink is 21.81±0.08 dynes/cm. The poor adhesion of the ink may be caused, at least in part, by the small difference (less than 10 dynes/cm) between the surface energy of the substrate and surface tension of the ruthenium based ink. To improve adhesion, the surface energy of the substrate may be improved (raised), for example either by UV or corona treatment. During testing, the surface of parchment paper was UV treated four times using the Fusion UV System 1300 MB. The surface energy of the UV-treated parchment paper was measured to be 22.09 dynes/cm. Thus, the impact of the UV treatment on the parchment paper is minimal. Similarly, no impact was observed with the corona treatment on the surface of parchment paper.

Figure 18A:
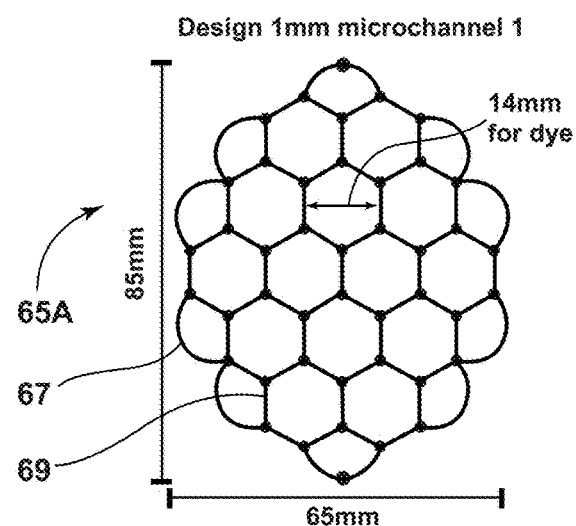
FIG. 18A is a schematic diagram showing the design of a microfluidic network in an oxygen generation patch or module, including a larger (85 mm×65 mm) model.
Figure 18B:
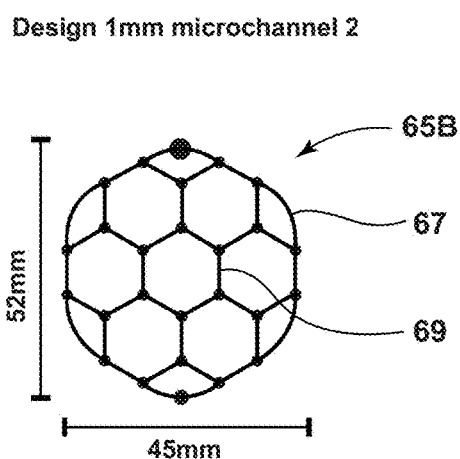
FIG. 18B is a schematic diagram showing the design of a microfluidic network in an oxygen generation patch or module, including a smaller (52 mm×45 mm) model.

As discussed above, smart dressing 1 (FIG. 1) includes microfluidic channels 15. FIGS. 18A and 18B show microfluidic networks 65A and 65B, which represent examples of the microfluidic channels 15 that could be used in the smart dressing 1 of FIG. 1. White regions or lines 67 comprise fluid channels, and black hexagonal areas 69 represent locations (cells) of the oxygen sensing dye. FIGS. 18A and 18B shows two designs, a smaller one 65A and a larger one 65B, to allow the patch to be adapted for wounds of various sizes. The designs 65A and 65B exhibit a honeycomb pattern due to the spatial and radial uniformity of the designs. The size of the hexagonal unit cells 69 was determined based on the test results discussed above. Specifically, testing showed that a 1 mm oxygen-generating spot could influence oxygenation within a 5-10 mm radius. Thus, the unit cells 69 have a radius of 7.5 mm. Testing of large-area bonding of PDMS to parchment paper via the use of partially-cured PDMS (as an interface between the two layers) was also performed. Testing revealed that this technique may not be sufficiently strong for assembling larger devices because it often results in delamination and/or leakages.

Figure 19:
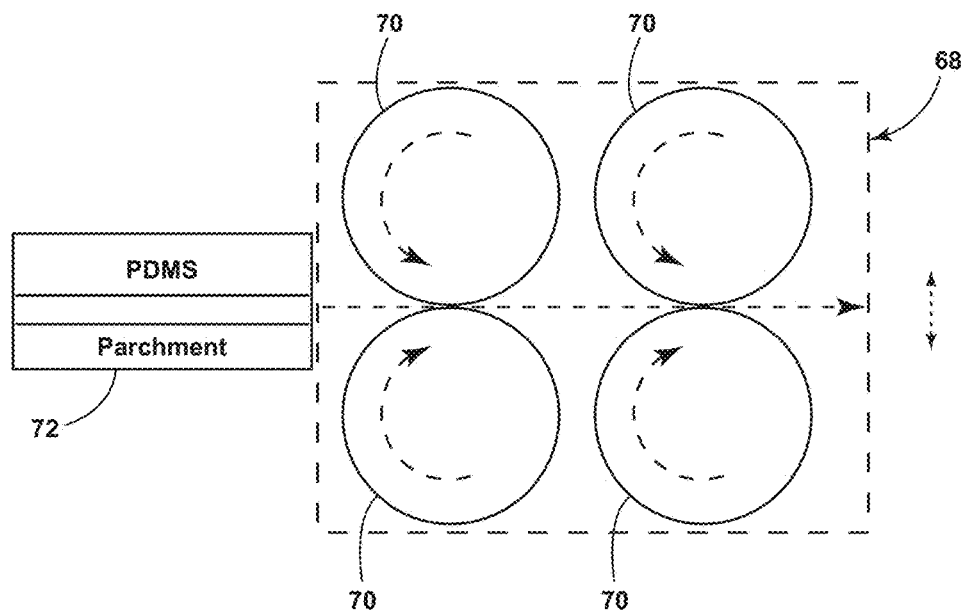
FIG. 19 is a schematic showing the use of pressure rollers for improving bonding.
Figure 20:
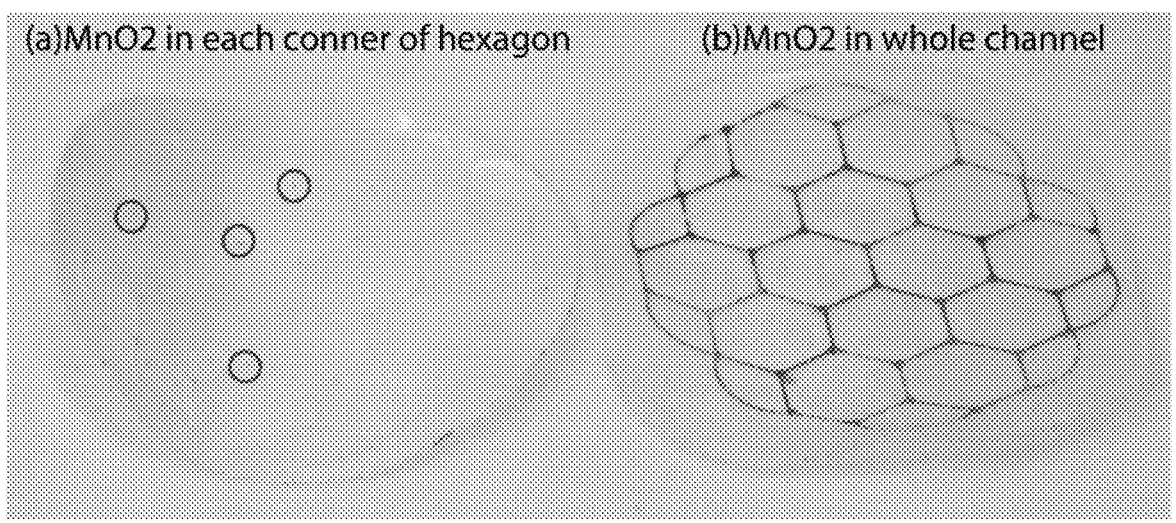
FIG. 20 is a photographic image showing test patches bonded with the use of pressure rollers.

To remedy the leakage and reliability issue, a bonding process utilizing lamination rollers was developed. Such rollers are typically found on hot lamination machines. During testing, a commercially available hot laminator machine 68 (Apache) was incorporated into the fabrication process as shown in FIG. 18. Specifically, paper/PDMS bilayers 72 were passed through rollers 70 before curing was complete, allowing the rollers 70 to apply pressure and squeeze out trapped gasses from the interface between the paper and PDMS. This technique allowed the successful creation of patches with stronger bonding and no leakages. Examples of these are shown in FIG. 19. The patch (a) in the left-hand side of the figure shows a patch with $MnO_2$ catalyst deposited on only the junctions of the channels (a few of which are identified with circles), whereas the patch (b) on the right-hand side of the figure shows a patch with channels that have been lined with $MnO_2$ (an alternative, pattern-less technique). The resulting patches exhibit functionality and robustness while remaining thin for conforming to human skin.

As discussed above, smart dressing 1 senses (measures) oxygen levels, and provides controlled flow of oxygen to a wound based, at least in part, on measured oxygen levels. Oxygen delivery is initiated with injected $H_2O_2$ over the printed $MnO_2$ on a parchment paper. The volume and duration of oxygen delivered to the wound is precisely controlled. The volume duration of oxygen can also be observed (measured) while the smart wound dressing is worn by a patient. The concentration of $O_2$ can also be monitored (measured) in real time to control the $O_2$ delivery based on a user's demand, or the condition of the patient.

A ruthenium complex may be used to measure the concentration of oxygen at the wound. During testing, the performance of printed $Ru(dpp)_3Cl_2$ (ruthenium dye) with different combinations of materials was characterized. First, a commercially available optical oxygen sensor (Redeye® patch from Ocean Optics) was characterized and observed. Then, printed ruthenium dye was characterized with different compositions of PDMS, polystyrene, and ethanol/chloroform.

The main mechanism of this sensor is the attraction of oxygen atoms by the ruthenium complex. Ruthenium dye excites when exposed to light having a wavelength of about 455 nm (blue), and emits fluorescence of 610 nm (red). The ruthenium dye fluorescence quenching is observed when oxygen atoms collide into the fluorescent ruthenium complex, transferring its energy. Thus, the quenching fluorophore results in lower fluorescent intensity in an environment having a high concentration of oxygen environment. This printed oxygen sensor can work in range of 0 to 100% of oxygen environment. It is used mostly for in situ and real-time monitoring of oxygen generation in water. For accuracy in measurement and observations, both the emitted wavelength of the fluorophore and dissolved oxygen concentration in water were characterized by optical and electrochemical sensors.

Figure 21:
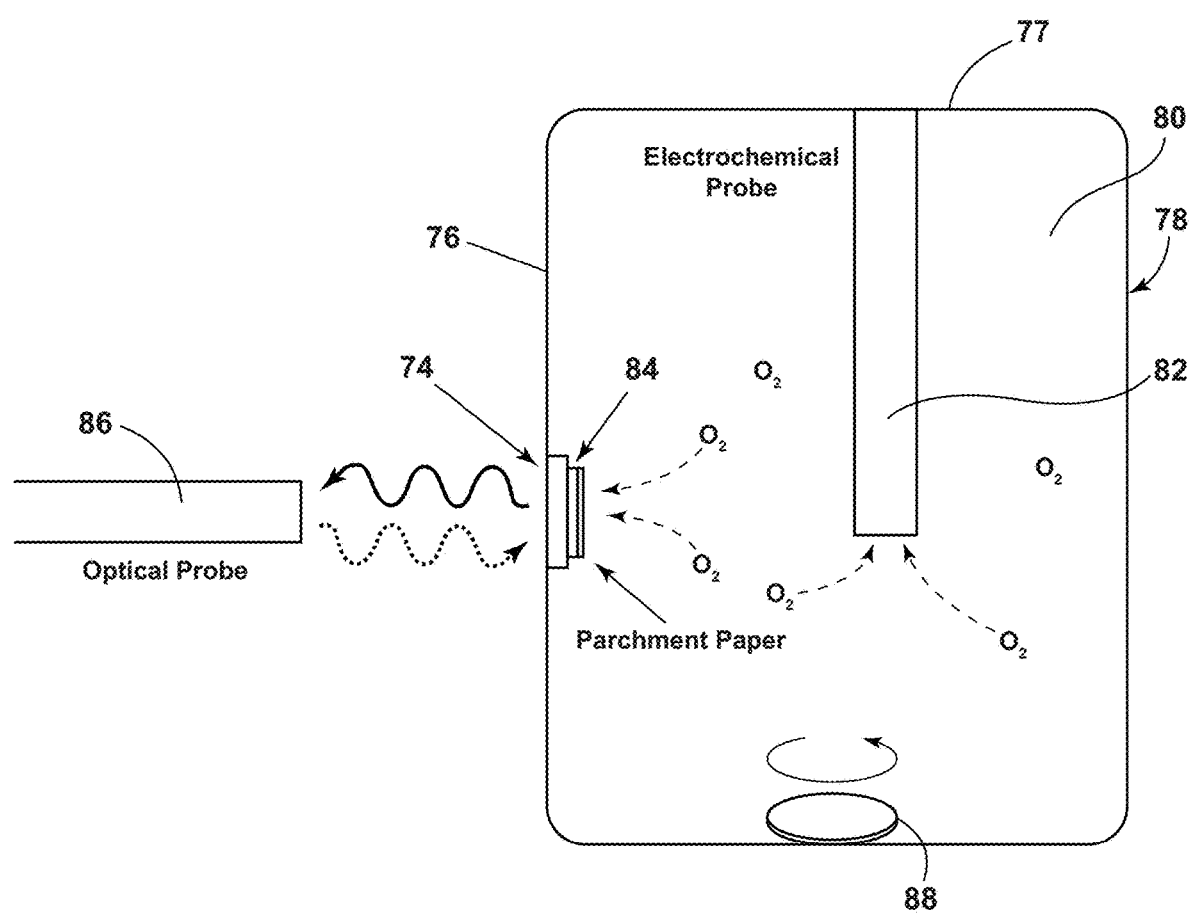
FIG. 21 is a schematic showing an experimental setup and O$_2$ sensing.

For testing purposes, ruthenium dye 84 (FIG. 21) was printed (diameter of 7.5 mm) on a parchment paper, then attached to transparent double-sided tape 74. The tape 74 was then placed on a wall 76 of a water container 78 facing outside for optical measurement as shown in FIG. 21. Water 80 was deoxygenated by pumping $N_2$ gas over 30 minutes. After deoxygenating, initial dissolved oxygen concentration of the water was measured with an electrochemical probe 82. The measured oxygen concentration was about 0.2 ppm at room temperature. It will be understood that "normal" (untreated) water contains oxygen concentration of 8 to 9 ppm (1 ppm=1 mg/L) in air. An optical probe 86 was placed about 2 mm away from the wall 76 of the water container 78 and positioned perpendicular to the dye 84. The electrochemical probe 82 was dipped into the water 80 deep enough so that a thermal sensor embedded in the probe 82 was completely submerged under the water 80. Two probes were calibrated before the measurement using two-point calibration (0% and 100% saturated water). A stirring magnet 88 was placed under the water 80 and stirred at 150 rpm. This ensured that the $O_2$ concentration inside the container was at equilibrium at all times.

Characterization was first conducted with a Redeye® patch, and compared to a first printed ruthenium-based sensor. To optimize the performance of the printed dye, multiple layers of sensors with different compositions were tested. These tests were conducted with one test sensor unit left in air up to 21% of oxygen concentration (9 ppm) and another pumped with $O_2$ gas close to 100% of oxygen dissolved in the water.

Figure 22:
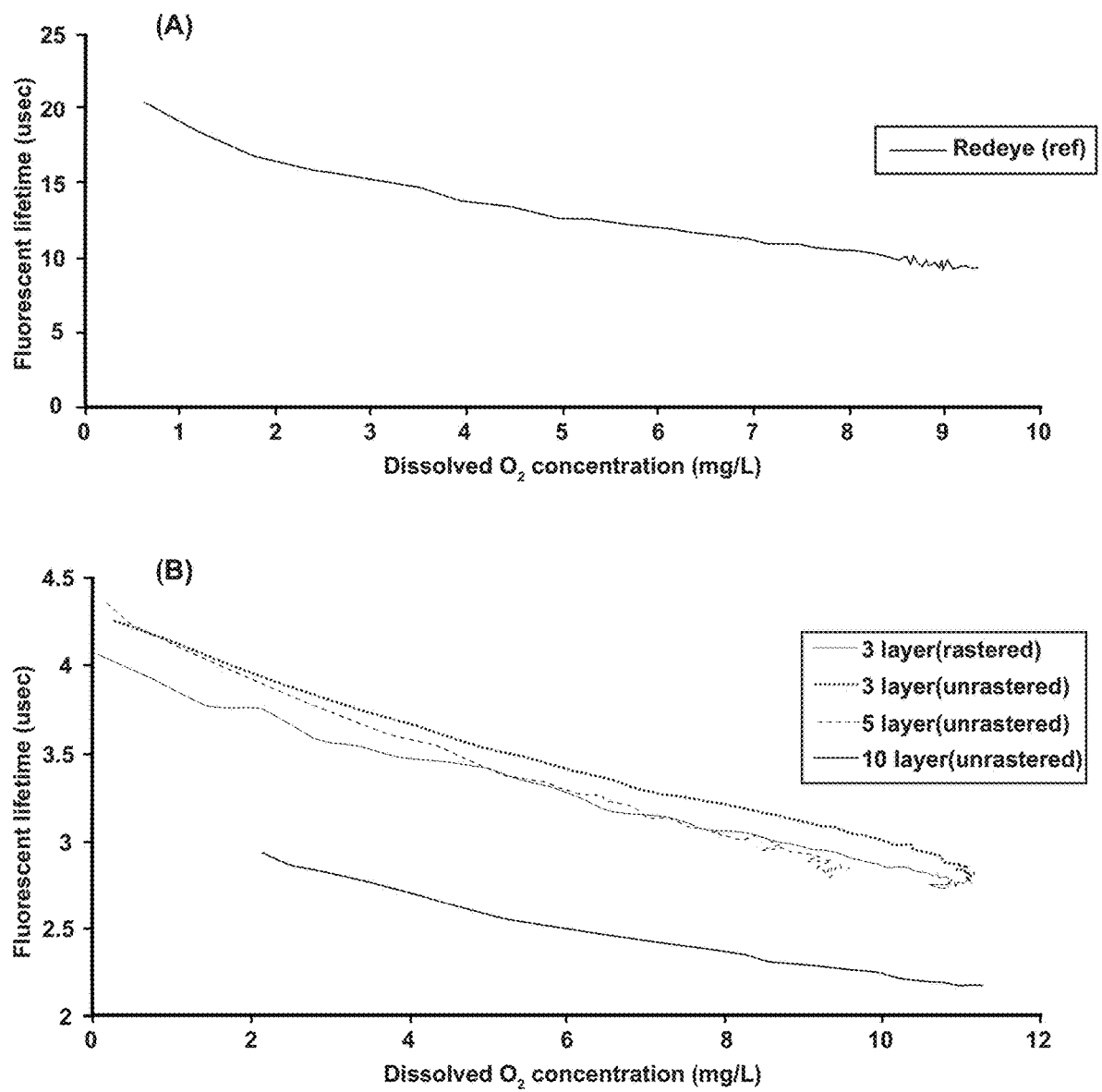
FIG. 22 shows graphs of optical and electrochemical responses of (A) a commercially available Redeye® oxygen sensing patch, and (B) printing ruthenium-based ink according to one aspect of the present disclosure.

Dissolved oxygen measurement and corresponding fluorescent lifetime of a Redeye® patch (commercially available oxygen sensor, Ocean Optics) was first characterized by exposing deoxygenated water 80 to air above an open top 77 of container 78, thereby slowly dissolving (absorbing) oxygen into the water 80. An initial reading of the Redeye® patch in the deoxygenated water had a maximum fluorescent lifetime of 20.342 μsec at 0.62 ppm of dissolved oxygen. Data was collected every 15 minutes until the oxygen concentration reached equilibrium with the ambient air (9 ppm). The graph (A) of FIG. 22 shows that fluorescent lifetime of the Redeye® patch exponentially decreases over time until it is in equilibrium to air. After water reaches equilibrium with air around 9 ppm, the fluorescent lifetime was saturated around 9 μsec as shown from the plot. Resulting fluorescent lifetime at 9 ppm was 9.247 μsec.

A first batch of printed ruthenium test sensors according to one aspect of the present disclosure was characterized using the same setup (FIG. 21) as the Redeye® patch. The samples of ruthenium dye were printed in multiples layers of 3, 5, and 10-layers with compositions of ruthenium dye, polystyrene, and chloroform in 1:1:100 ratio. Sensors with 3 multiple layers were printed on two different conditioned substrates (parchment paper) that were laser treated (rastered) and non-laser treated (unrastered). The laser treatment was performed to increase the adhesion of the ruthenium dye to the paper and for better absorbance of $O_2$. Each sample was submerged and placed on the wall 76 of the container 78 under deoxygenated water 80, then measured using both optical probe 86 and electrochemical probe 82, leaving water to dissolve (absorb) oxygen from air over time. Compared to the Redeye® patch, the printed ruthenium dye showed 0.2 times smaller fluorescence lifetime at the initial reading of deoxygenated water. The fluorescent decay of the Redeye patch was ten times faster than the printed sensor as shown by the lower graph (B) of FIG. 22.

The lower graph (B) of FIG. 22 shows that the emitted wavelength from the excited ruthenium dye was successfully detected using the optical probe 86. The fluorescent lifetime of the printed sensors also had exponential decay over time like the Redeye® patch. However, multiple layered samples 3 and 5 did not show a significant variation compared to the 10 layered samples. Printed sensors with 10 layers had the lowest performance among the group due to the poor adhesion between the dye and the parchment paper. Some fragments of particles of the ruthenium dye of the 10 layered sample fell off the parchment paper. Other test samples such as the 3 and 5 layer samples also were not uniform. However, the sensing of these non-uniform 3 and 5 layer samples was not significantly different, as was the case for the 10 layer samples. Laser treatment of parchment paper did not show a significant change in sensing as the plot shows between laser treated (rastered) and non-treated (unrastered) samples.

During testing, a second batch of sensors were printed. These test samples included single layer samples and 2 and 3 layer samples. The samples were printed on unrastered parchment paper. Materials used to print this batch were ruthenium dye, ethanol, and ethyl cellulose mixed in 1:1:100 ratio by weight. The second batch samples showed better uniformity compared to the first printed sensors. These samples were primarily characterized in a deoxygenated water container 78 having an opening 77 exposed to air/oxygen such that the water continuously dissolved oxygen from the air until the oxygen concentration in the water reached equilibrium.

Another aspect of the present disclosure is a portable circuit which uses the fluorescence quenching method to monitor oxygen concentration.

By exciting the ruthenium dye periodically with blue light, measuring the periodic fluorescence of the dye, and calculating the delay between excitation and emission, it is possible to extrapolate oxygen concentration using the Stern-Volmer formula.

As discussed above, in connection with FIG. 16, a microcontroller-generated square wave may be fed into a series of low-pass filters, which act as a square-to-sine converter. The sine wave is then used to drive a blue LED 54 and excite the ruthenium dye 56. A transimpedance amplifier can be used to capture the sinusoidal fluorescence of the ruthenium dye 56, and this fluorescence signal is then compared to the original excitation signal so that the microcontroller 50 can calculate the amount of oxygen present and control the hydrogen peroxide pump accordingly.

Figure 23:
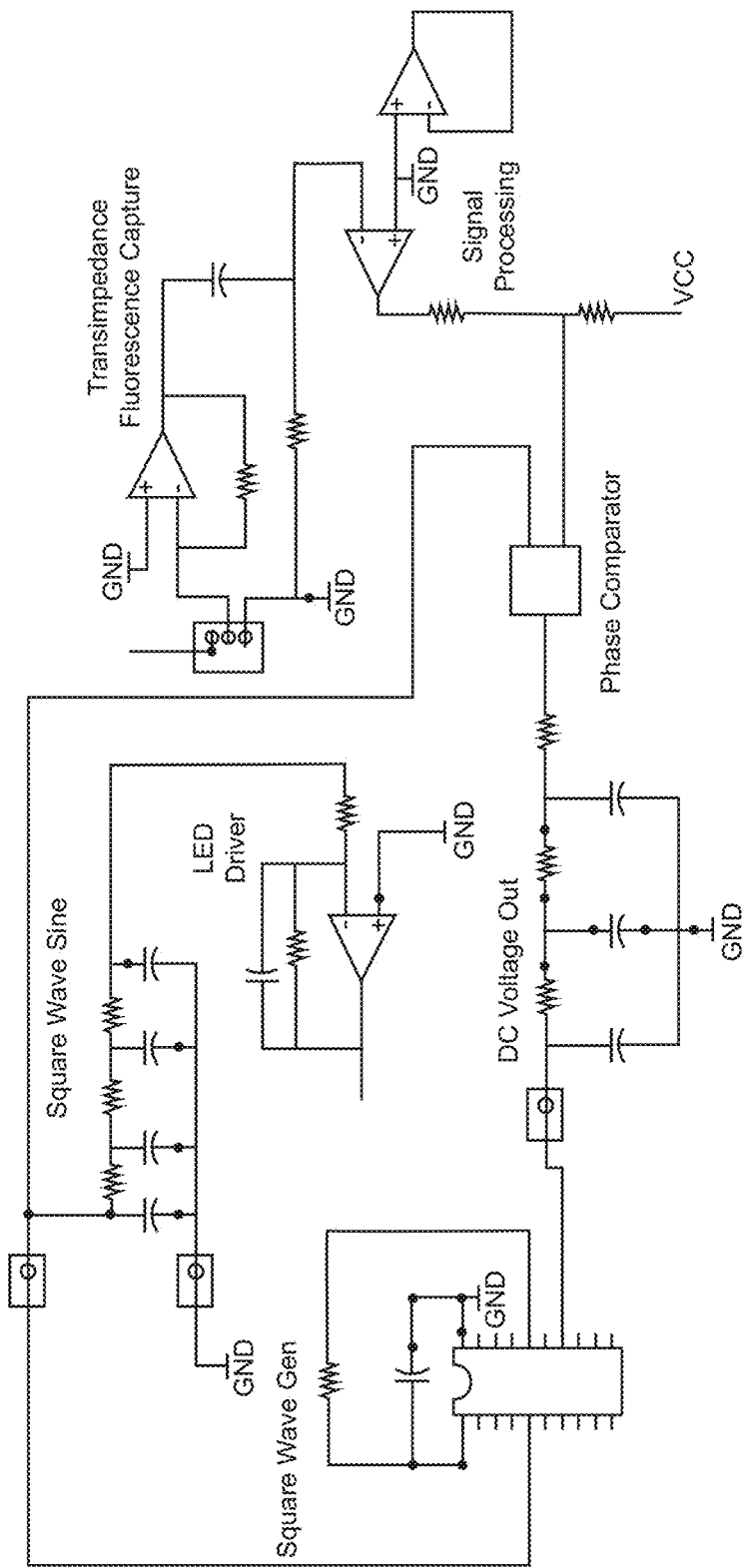
FIG. 23 is an electrical schematic of an oxygen sensing circuit.

Circuit operation, corresponding to the schematic of FIG. 23:

1. TI MSP430G2553 Microcontroller provides a square wave at a pre-programmed frequency
2. A series of low-pass filters remove the high frequency content of the square wave, acting as a square-to-sine converter.
3. The sine wave is fed into a filtering operational amplifier, the output of which drives the excitation LED.
4. The transimpedance amplifier (R11=photodiode) picks up the fluorescence signal.
5. The sinusoidal fluorescence is converted into a square wave for processing.
6. An XOR gate compares the original square wave to the fluorescent square wave. As the phase between the two signals increases, the outputted pulse width increases.
7. The output pulse of the XOR gate is low-pass filtered to a DC voltage. Higher duty cycle of XOR gate corresponds with higher DC voltage.

The cytotoxicity of the materials used for the fabrication of the smart wound dressing 1 described above was investigated following standard ISO 10993-05 (Cytotoxicity) and ISO 10993-12 (Sample preparation and reference materials).

All samples were ≤0.5 mm thick and prepared as 8 mm-diameter discs (surface area of 0.50 cm$^2$). Samples were sterilized by the STERRAD® process (low temperature hydrogen peroxide gas plasma) and then extracted for 24 h/37° C. in complete growth medium (Eagle's Minimum Essential Medium+10% horse serum+100 IU/ml penicillin+100 μg/ml streptomycin) using an extraction ratio of 6 cm$^2$/ml. At the time of the extraction, L-929 mouse fibroblast cells (NCTC clone 929: CCL 1, American Type Culture Collection, Manassas, Va., USA) in passage 3 were lifted from the culture flask using trypsin/EDTA. An aliquot was counted using trypan blue, and then cells were re-suspended in complete growth medium at a density of $1 \times 10^5$ cells/ml. Cells were dispensed into wells of 96-well culture plates ($1 \times 10^4$ cells/well) and cultured at 37° C. in a humidified atmosphere of 5% $CO_2$/95% air. After 24 h, the culture medium was removed and replaced with 100 μl of extractant. Some wells received sodium dodecyl sulfate (0 to 400 μM in EMEM; positive controls), low-density polyethylene extract (1.25 cm$^2$ LDPE/ml EMEM; negative control), or complete growth medium alone. Cells were then cultured for an additional 24 h. Images (mag. of 100× and 200×) of cell cultures were recorded by photo microscopy using a Olympus CK40 inverted microscope and Insight2 SPOT camera (Diagnostic Imaging) and the number of attached and dead cells were manually counted at a later time using ImageJ (NIH). In addition, images were graded for morphological evidence of cytotoxicity using the ISO 10993-5 standard, where the 0 to 4 scale represents no, slight, mild, moderate, or severe cytotoxicity, respectively. Subsequently, cells in culture plates were washed once with Hank's Balanced Salt Solution and metabolic activity was measured by incubating cells with 100 μl of WST-1 cell proliferation reagent (Roche Diagnostics) for up to 4 h at 37° C. To determine cytotoxicity, absorbance of the medium in wells was measured at 450 nm after 2 and 4 h using a microplate reader (PHERAstar) and was corrected using absorbance measurements at 630 nm and using blanks. To check for mycoplasma contamination of the cultures, medium was saved and tested using the luminescent MycoAlert Plus mycoplasma detection kit (Lonza).

Absorbance is proportional to the amount of formazan product generated by the metabolic activity of cells. Thus, lower absorbance values correlate with increased cytotoxicity. Mean absorbance values for cells treated with extracts of palladium, palladium+polystyrene, or palladium+PDMS on paper substrates (0.734, 0.816, or 0.811, respectively) are similar to values for cells incubated in EMEM alone (0.827) or the LDPE extract (negative control; 0.753). However, cells treated for 24 h with the extracts of ruthenium or ruthenium+polystyrene show considerable cytotoxicity (corrected absorbance readings of 0.318 or 0.089, resp.), with only 38.4% or 10.7%, respectively, of the metabolic activity of cells that were cultured in EMEM alone. The extract created from ruthenium+PDMS on paper was borderline non-cytotoxic, having a corrected mean absorbance reading of 0.625 or 75.6% (readings below 70% would be considered cytotoxic according to ISO 10993-05).

The results are confirmed qualitatively via microscope images. Micrographs of cells treated with EMEM, palladium, palladium-polystyrene, palladium-PDMS, and ruthenium-PDMS extracted media had cytotoxicity scores of 0-1, while micrographs of cells treated with ruthenium and ruthenium-polystyrene extracted media had scores of 2-3. According to the standards, scores >2 are considered to be cytotoxic.

Figure 24:
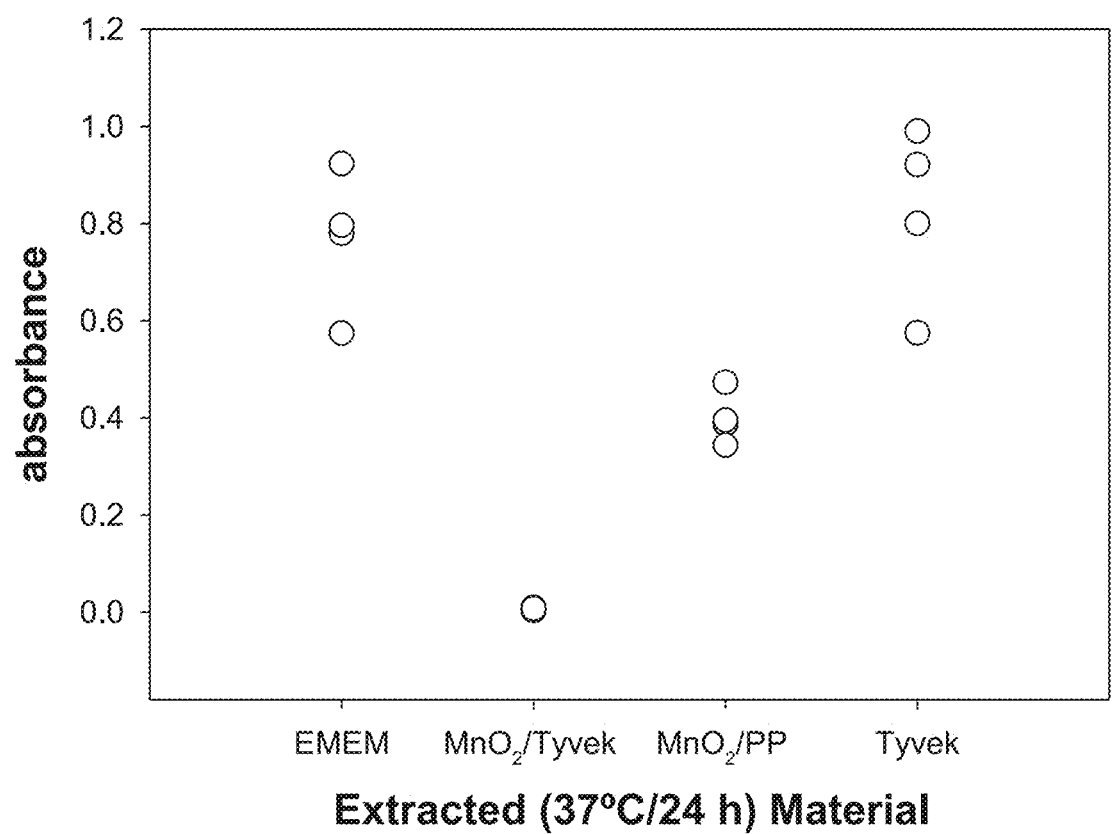
FIG. 24 shows a cytotoxicity assessment of smart dressing components for oxygen generation.

The results of the cytotoxicity assay on the various combinations of oxygen-generation materials are summarized in FIG. 24. Mean absorbance values for cells treated for 24 h in EMEM or extracts of Tyvek® were 0.768 or 0.822, respectively. However, extracts made from $MnO_2$ on Tyvek® or $MnO_2$ on parchment paper (PP) were cytotoxic, producing mean absorbance values of 0.005 or 0.399, respectively. This represents metabolic activity of only 0.7% or 52%, respectively, of healthy cells. Morphological grading confirmed the findings. Cells treated with EMEM or extracts of Tyvek®, $MnO_2$ on Tyvek®, and $MnO_2$ on parchment paper (PP) produced scores of 0, 1, 4, and 3, respectively.

Cells in additional wells were cultured in 0-400 µM sodium dodecyl sulfate in EMEM for 24 h to serve as positive cytotoxicity controls. The test results confirmed that increasing concentrations of SDS produced a graded and increasing cytotoxic response as expected. Mean absorption readings fell from about 0.7 to 0 between 0 and 300 µM SDS. Morphology scores ranged from 0 to 2 between 0 and 150 µM SDS. Concentrations of SDS above 200 µM were cytotoxic.

To test cell cultures for mycoplasma contamination, a MycoAlert Plus kit was used. Luminescence of the test solution is measured in the presence of reagent alone or reagent plus substrate and ratios are calculated and compared to positive and negative controls that are purchased with the test kit. Ratios <0.9 are negative and >1.2 are positive for mycoplasma. Borderline values between 0.9 and 1.2 are retested after 24 h. The cell cultures used for the cytotoxicity study produced a ratio of 0.31 (negative), while positive and negative controls produced ratios of 22.38 and 0.32, respectively.

Using appropriate positive and negative controls, extracts of palladium, palladium+polystyrene, and palladium+PDMS were non-cytotoxic. Ruthenium+PDMS was marginally non-cytotoxic. Extracts of ruthenium alone on paper and ruthenium+polystyrene were cytotoxic. Extracts of $MnO_2$ on parchment paper or on Tyvek® were cytotoxic, but Tyvek® alone was non-cytotoxic. Cultures tested negative for mycoplasma.

Based on the print quality of the ruthenium dye ink (Ruthenium+Ethanol+PDMS) discussed above, it was concluded that the film formation of ruthenium dye and its adhesion with parchment paper is poor. This may be due to the insolubility of PDMS with the ink system. To improve both the film formation and adhesion, among various binders such as ethyl cellulose (polymer), ethyl cellulose was chosen because of its solubility in ethanol and better film formation properties. Ruthenium dye (powder form) is mixed with ethanol and ethyl cellulose in a 1:100:1 weight ratio on a hotplate with magnetic stirrer at 700 rpm for 20 hours at room temperature.

As discussed above, for ink jet printing the Z-number should be in the range of about 2 to about 10. Also, inks having a viscosity that is less than about 10 cP are typically preferred for inkjet printing.

For the ruthenium dye+ethanol+ethyl cellulose based ink solution, the measured surface tension is 21.48±0.12 dynes/cm. The measured density of the ink solution is 0.78 g/ml. To determine the viscous behavior of the ink solution under a broad range of temperatures from 20° C. to 60° C., a rheometer was used. The shear rate was maintained at 1000 (1/s) and the viscosity was decreased from 5.6 cP to 3.4 cP for the temperature range of 20° C. to 60° C. After substituting the measured values, Z-numbers ranging from 3.4 to 5.5 were calculated as the temperature increased from 20° C. to 60° C. It is therefore evident that the ink is suitable for inkjet printing at room temperature.

Figure 25:
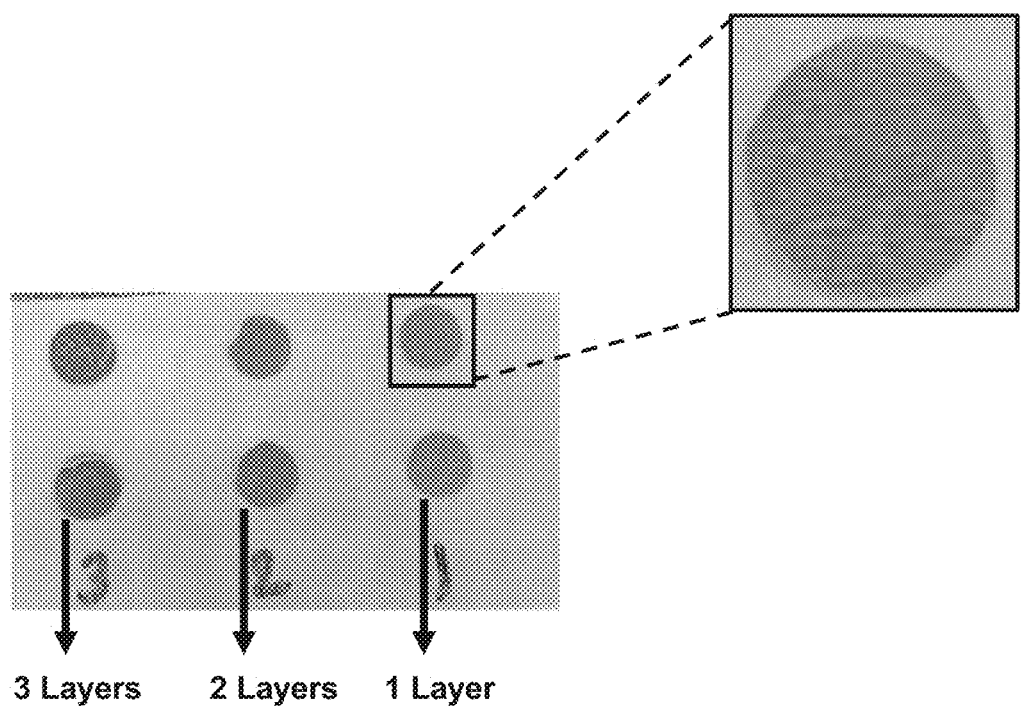
FIG. 25 is an image of an oxygen-sensitive dye printed on unrastered parchment paper.

During further testing, multi-layer samples (3 layer, 2 layer, and 1 layer) of the ruthenium dye-based ink, with ethanol as solvent and ethyl cellulose as the polymer binder, were inkjet printed onto unrastered parchment paper in an array of circular spots with a diameter of 7.5 mm, with 10 µm drop spacing and resolution of 2540 dpi, using a DIMATIX inkjet printer (DMP 2831). The ruthenium ink solution was loaded into a DIMATIX DMC-11610 cartridge (10 pl) through a 25 mm disposable Whatman syringe filter, with a poly vinylidene difluoride filter (PVDF) filter membrane of 0.45 µm pore size, to filter any large particles that may have agglomerated in order to achieve smooth printing. Each layer of the printed ink was cured on the stage of the inkjet printer at 55° C. A 40 V actuation voltage, applied at 5 kHz firing frequency, was employed for inkjet printing the ruthenium ink. The printed samples on the unrastered parchment paper are shown in FIG. 25.

From the printed samples, it was observed that the film formation and coverage of ruthenium dye with ethyl cellulose binder is good when compared to the ruthenium dye with PDMS binder. However, the adhesion between the parchment paper and multiple layers of ruthenium dye (with ethyl cellulose binder) was potentially insufficient.

As discussed above, the surface energy of calendered parchment paper was measured with the FTA 200 using Owens-Wendt method and was calculated as 21.99 dynes/cm. The surface tension of the ruthenium dye+ethanol+ethyl cellulose-based ink solution is 21.48±0.12 dynes/cm. As also discussed above, the difference between the surface energy of the substrate and surface tension of the ink should be greater than 10 dynes/cm to achieve good adhesion between the substrate and ink. Various surface treatments such as UV (Fusion UV Systems 1300 MB), corona (Electro-technic BD-20v corona treater), and sintering (Novacentrix Pulseforge® 1200) have been employed to improve/modify the surface energy of calendered unrastered parchment paper. However, it is observed that these treatments have minimal or no impact on the surface of parchment paper.

However, testing revealed that laser surface treatments can significantly alter the surface energy of parchment paper. Specifically, when the surface of calendered parchment paper is subjected to a laser ablation/rastering process using a PLM 6MW laser machine (available from Universal Laser Systems), the surface energy can be increased to 64 dynes/cm. The surface energy values show that the laser rastering process has a strong impact on the surface of parchment paper. Also, during testing, the contact angle of ruthenium ink with ethyl cellulose binder with parchment paper was measured as 30.37±1.35 degrees. This implies good wetting properties.

Figure 26:
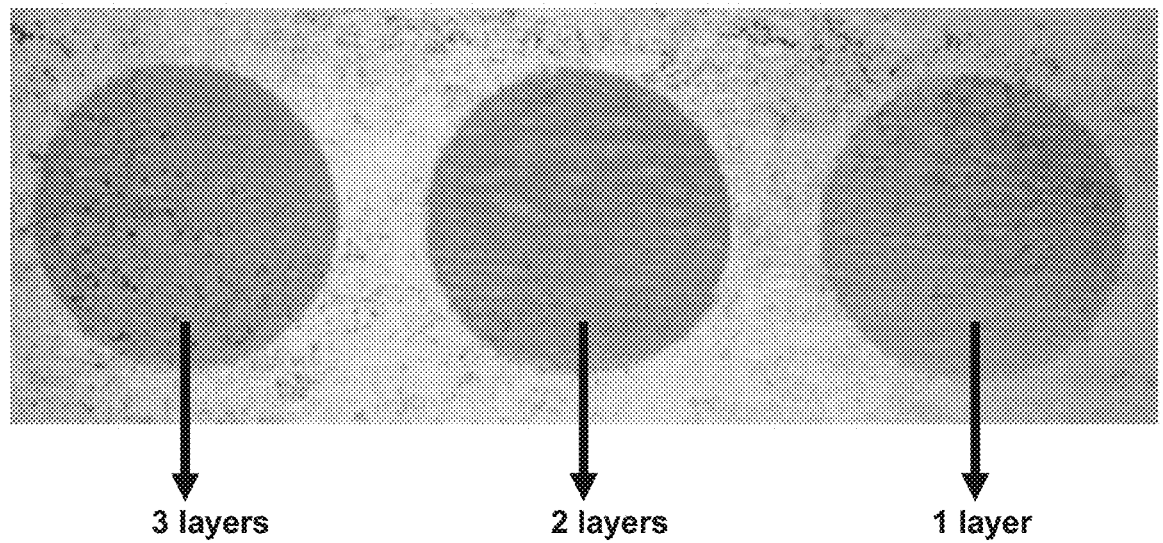
FIG. 26 is an image showing an ink jet printed oxygen-sensitive dye with 7.5 mm diameter circular spot size.

The ruthenium ink solution with ethyl cellulose binder was inkjet printed onto laser rastered parchment paper using the same settings discussed above. Photographs of the printed samples with multiple layers of ruthenium dye on the laser rastered parchment paper are shown in FIG. 26. It was observed that the adhesion between the ruthenium dye and the laser rastered paper is very good (confirmed by placing/sticking and removing tape on the printed dye). Also, digital microscope images (not shown) confirmed that the film formation and coverage of the ruthenium dye was good.

However, some burnt fibers (black spots) were evident in the rastered area due to the application of high power intensity during the laser rastering process. In order to reduce or eliminate burning of fibers, a profile of power intensity and laser speed effects on the surface energies of the parchment paper may be utilized to identify a suitable laser rastering process that provides a surface energy value above 32 dynes/cm without burning of paper fibers.

A suitable binder (ethyl cellulose) was identified and used in the ruthenium ink system in place of PDMS and a Z-number has been calculated. The ethyl cellulose binder provided acceptable printed ruthenium film formation and coverage. Proper adhesion may be provided by laser rastered calendered parchment paper for inkjet printing.

As discussed above, an oxygen generation patch may be fabricated using partially cured PDMS to bond parchment paper with laser-rastered spots to PDMS with molded microchannels. This method is capable of creating a flexible and conformable wound dressing patch. However, this process can be time consuming, which may interfere with large scale production. Thus, processes that may be more suitable for large scale (high speed) production have been developed, as described herein. Testing showed that the processes can improve the mechanical properties of the oxygen delivery system/platform and reduce fabrication cost.

Figure 27:
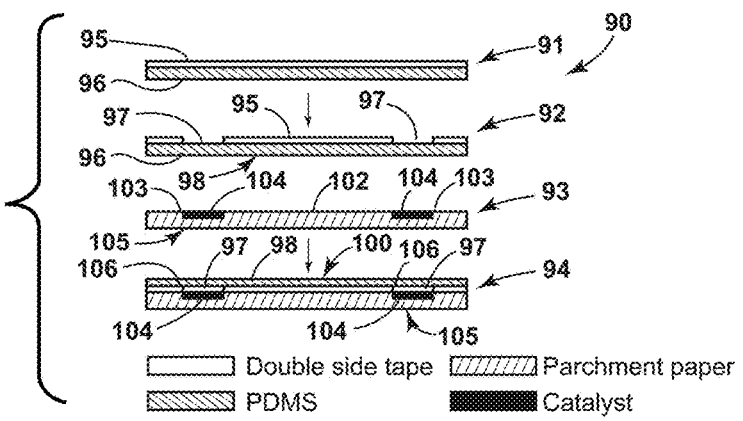
FIG. 27 is a schematic showing fabrication of an oxygen delivery patch.
Figure 28:
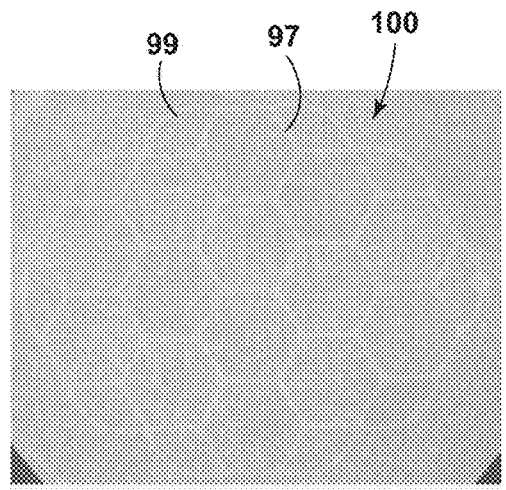
FIG. 28 is a photographic image of an oxygen delivery patch.

With reference to FIG. 27, a method 90 may be utilized to fabricate an oxygen delivery patch. First, at step 91, double-sided transparent tape 95 (e.g. 3M 300LSE) is bonded to a layer of PDMS 96 utilizing an oxygen plasma process. At step 92, the tape 95 is then laser-rastered (ablated) to form fluid channels 97 in a predefined honeycomb pattern 99 (see also FIG. 28). The tape 95 (with channels 97) and PDMS 96 form a first subassembly 98. The PDMS layer 96 may also be laser-rastered to a certain depth, provided the thickness of the rastered regions of the PDMS layer are not reduced to a level affecting the robustness of the patch 100. At step 93, a layer of parchment paper 102 is laser-rastered (ablated) at selected surface regions 103, and oxygen catalyst 104 is inkjet printed on to the rastered surface regions (spots) 103 to form a second subassembly 105. Oxygen catalyst 104 may be printed utilizing ruthenium dye/ink (Ru+Ethanol+PDMS) as discussed above. It will be understood that forming the first subassembly 98 (steps 91 and 92) and forming the second subassembly 105 (step 93) may occur at the same time or at different times. The oxygen catalyst 104 forms a honeycomb pattern that aligns with the channels 97 of the tape 95 and PDMS layer 96. At step 94, the first and second subassemblies 98 and 105, respectively, are bonded together with catalyst 104 forming a side wall that closes off channels 97 to form fluid conduits 106 having a honeycomb pattern 99 (FIG. 28). During step 94, the parchment paper 102 is oxygen plasma bonded to the tape 95.

Peel strength testing of a patch 100 fabricated according to process 90 (FIG. 27) showed that the interface bond between PDMS layer 96 and parchment paper 102 is about 7N per 2 cm width. This is about twice the peel strength obtained using partially cured PDMS as the bonding glue.

Bonding strength testing was also conducted on a patch fabricated according to process 90 (FIG. 27). This testing was conducted to determine if the patch 100 can withstand the pressure resulting from pumping hydrogen peroxide with a certain flow rate through the fluid conduits 106 during use of patch 100. In one test, the outlet was open and fluid was pumped at an escalated flow rate. In a second test, the outlet was sealed, and fluid was pumped with a fixed flow rate. Testing showed that a patch 100 can withstand up to 30 psi with a flow rate up to 7 ml/min in the open outlet case. Patch 100 can withstand up to about 3 psi with a fixed flow rate at 30 µl/min in the closed outlet case.

The required flow rate for a wound dressing is about 10 µl/min. Thus, the test results show that a patch 100 fabricated according to process 90 (FIG. 27) meets the requirement of a sustained $H_2O_2$ pumping with a flow rate of about 10 µl/min for several hours.

Robustness testing to determine the effect of bending/curving of patch 100 was also conducted. Patch 100 is designed to conform to a shape/curvature of a patient's skin around a wound. The curvature may vary for different patients and wounds. In general, the patch 100 must not leak during continuous pumping of $H_2O_2$. During the robustness test, the patch 100 was folded into six different configurations ranging from about 90 degrees to about 180 degrees (fully folded). Thus, a patch 100 was first tested at a bend/fold (curvature) of about 90 degrees, followed by testing at a greater bend/fold of about 108 degrees, followed by a bend/fold of about 126 degrees, etc. until the maximum bend/fold of 180 degrees ($6^{th}$ curvature) was reached. $H_2O_2$ was then continuously pumped through the fluid microchannels/conduits 106 at a constant flow rate of about 0.1 ml/min for 6 hours.

The fluid pressure inside the fluid conduits 106 was also measured continuously for all six curvatures. The test demonstrated that the patch 100 provided a constant pressure range from about 0.4 to about 0.5 psi. This indicates that the patch 100 can sustain up to at least about 6 hours of continuous operation under a maximum 180 degree folding state (zero pressure would be detected if leakage had occurred).

Figure 29:
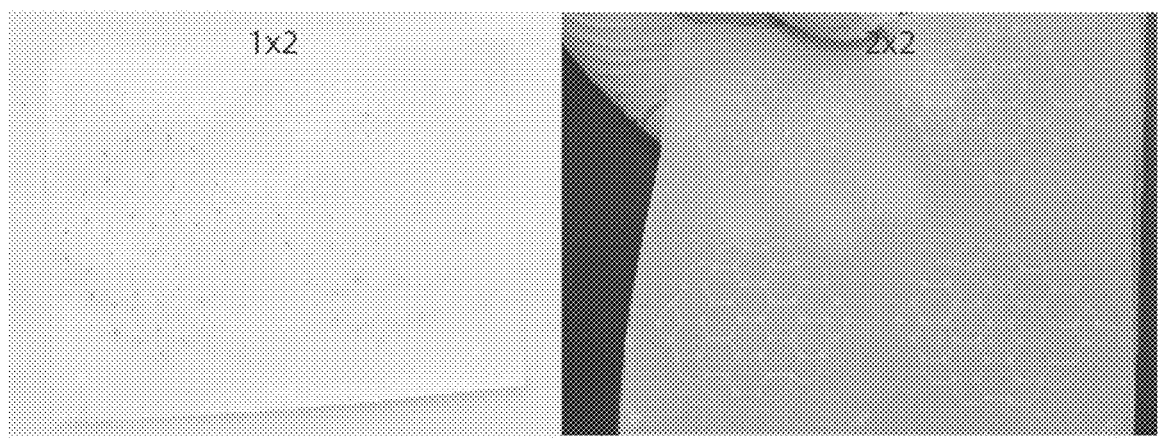
FIG. 29 is a photographic image of fluid (oxygen) patch arrays of size 1×2 and 2×2.

The process 90 (FIG. 27) is scalable to provide increased production efficiency. Specifically, with reference to FIG. 29, patch arrays (e.g. 1×2 and 2×2) may be fabricated using the process 90 (FIG. 27) utilized for a single patch. An array (e.g. 2×2 array) does not require additional fabrication time compared to fabrication of a single patch 100. Thus, the process 90 and patch 100 provide improved mechanical properties and also increase fabrication efficiency in a scalable production process.

Additional characterization (testing) of the ruthenium oxygen sensors and substrate (parchment paper) of the present disclosure was conducted by measuring dissolved oxygen in deoxygenated water. This additional testing was conducted using substantially the same test set up described above in connection with FIG. 21. First, multiple layers of the ruthenium dye (ink) (ruthenium based ink with ethyl cellulose binder) were tested. This formula produced a more uniform printing of the ruthenium dye (ink) on the parchment paper. Also, laser treated parchment paper was tested to determine if laser treating increased the adhesion of the printed ruthenium dye.

A test oxygen sensor was fabricated by printing ruthenium (Ru) dye on a piece of parchment paper (diameter=7.5 mm), and the parchment paper was bonded to double-sided tape. Referring again to FIG. 21 the ruthenium printed side of the test sensor was taped to the wall 76 of the water container 78 facing outside for optical measurement in substantially the same manner discussed above in connection with FIG. 21. Deoxygenated water was prepared before the experiment, and oxygen concentration was measured with both electrochemical and optical oxygen probes 82, 86, respectively. During the experiment, oxygen gas was injected into the water 80 through external tubing (not shown). The stirring magnet 88 was utilized to ensure uniform $O_2$ concentration. The experiment was conducted with three different sensors, namely, sensors having single, double, and triple layers of ruthenium dye.

The objective of this experiment was to test the fluorescence lifetime decay of the single and multi-layered ruthenium dye samples. Larger fluorescence lifetime decay from multi-layered ruthenium dye was expected. From the previous experiment of printing ruthenium dye, highly concentrated ruthenium particles showed difficulties in printing due to the viscosity of the ink and mixing with solvent. Therefore, a method of multi-layer printing was selected to increase its range of quenching decay time of the fluorescence with more oxygen absorbance at the sensor. For this test, oxygen gas was injected into the deoxygenated water then measured with optical (μsec) and electrochemical probes (1 mg/L=1 ppm). Oxygen gas injection was stopped when the measurement was taken. The gas injection continued until the oxygen concentration reached 27 mg/L, which was the limit of electrochemical probe 82. Double and triple-layered ruthenium dye samples were prepared, and the fluorescence lifetime decay performance was measured (with oxygen gas injected). Fluorescence lifetime decays exponentially over saturation of oxygen gas in the liquid. The fluorescence lifetime decay was measured up to about 25 to about 27 mg/L due to limit of the measuring device. Nevertheless, measurement was compared at 9 mg/L, since it is 21% of oxygen concentration in room temperature. Lifetime decay were −0.101 and −0.109 μsec for double and triple layer samples, respectively. Triple layered samples showed higher changes in quenching decay time of fluorescence. However this difference is not significant compared to the results for the double-layer samples. Also, the single-layer samples showed better quenching fluorescence at around 0 percent dissolved oxygen, resulting in larger changes of fluorescence lifetime decay at 9 mg/L. Oxygen absorbed from the parchment paper through the multi-layered ruthenium dye may not be effectively diffused through each layer. Also, the gradients of multi-layer printed ruthenium dye samples were more significant compared to the gradients of single layer samples. Thus, multiple layers of printed ruthenium dye do not appear to be effective with respect to increasing the performance of quenching fluorescence decay.

Additional testing was also conducted to compare the performance of printed oxygen sensors on rastered and unrastered parchment paper to determine if rastering provides increased adhesion. As discussed above, printed ruthenium dye on unrastered parchment paper tended to adhere poorly, and particles from the printed sensor fell off the unrastered parchment paper.

During testing, parchment paper was rastered with a laser engraving machine. Test samples were fabricated by printing ruthenium dye in single, double, and triple layers on laser engraved (rastered) parchment paper. Three experiments were repeated for each group of test samples. Both unrastered and rastered parchment paper showed exponential fluorescence lifetime decay. At an atmospheric oxygen level of 21%, the single-layer test samples resulted in a faster fluorescent lifetime drop compared to the multiple layer test samples. The results are shown in Table 4 below.

TABLE 4

Fluorescence lifetime decay up to 9 mg/L for ruthenium dye in single, double, and triple layers.

| Layer | Δτ (Unrastered) | Δτ (Rastered) |
| --- | --- | --- |
| 1 | −1.147 | −1.091 |
| 2 | −0.757 | −1.066 |
| 3 | −0.771 | −0.579 |

As illustrated in Table 4, the decay rate up to 9 mg/L was similar in both unrastered and rastered single layered test samples. As a result, the multi-layered ruthenium dye test samples had a smaller change of lifetime decay compared to the single layer test samples. Consistent with prior observations, the printed ruthenium dye on unrastered test samples tended to separate from the parchment paper, and edge portions of the printed ruthenium dye fell apart during most of the experiments. Test samples having a single layer of ruthenium dye printed on rastered parchment paper had significantly better adhesion. Based on these results, a suitable oxygen sensor can be fabricated by printing a single layer of ruthenium dye onto a rastered parchment paper surface.

The cytotoxicity of the materials used for the fabrication of the smart wound dressing 1 was investigated following standard ISO 10993-05 (Cytotoxicity) and ISO 10993-12 (Sample preparation and reference materials). This subsection describes the methods and presents the results of the cytotoxicity experiments.

Samples were sterilized by the STERRAD® process (low temperature hydrogen peroxide gas plasma) and then extracted for 24 h/37° C. in complete growth medium (Eagle's Minimum Essential Medium+10% horse serum+ 100 IU/ml penicillin+100 μg/ml streptomycin) using an extraction ratio of 6 $cm^2$/ml. In some experiments, additional samples were sterilized by dipping samples into 100% ethanol or 75% isopropanol for 5 minutes and allowing time to air dry before extraction. At the time of the extraction, L-929 mouse fibroblast cells (NCTC clone 929: CCL 1, American Type Culture Collection, Manassas, Va., USA) in passage 3-10 were lifted from the culture flask using trypsin/ EDTA. An aliquot was counted using trypan blue, and then cells were re-suspended in complete growth medium at a density of $1\times10^5$ cells/ml. Cells were dispensed into wells of 96-well culture plates ($1\times10^4$ cells/well) and cultured at 37° C. in a humidified atmosphere of 5% $CO_2$/95% air. After 24 h, the culture medium was removed and replaced with 100 μl of extractant. Some wells received sodium dodecyl sulfate (SDS; 0 to 400 μM in EMEM; positive controls), low-density polyethylene extract (1.25 $cm^2$ LDPE/ml EMEM; negative control) or complete growth medium alone. Cells were then cultured for an additional 24 h. Subsequently, cells in culture plates were washed once with HBSS and metabolic activity was measured by incubating cells with 100 μl of WST-1 cell proliferation reagent (Roche Diagnostics) for up to 4 h at 37° C.

To determine cytotoxicity, absorbance of the medium in wells was measured at 450 nm after 2 and/or 4 h using a microplate reader (PHERAstar) and was corrected using absorbance measurements at 630 nm and using blanks. Absorbance levels are proportional to the metabolic activity of cells and therefore inversely related to cytotoxicity. To check for mycoplasma contamination of the cultures, medium was saved and tested using the luminescent Myco- Alert Plus mycoplasma detection kit (Lonza). Statistical significance was determined using analysis of variance and Tukey-Kramer post-test.

Figure 30:
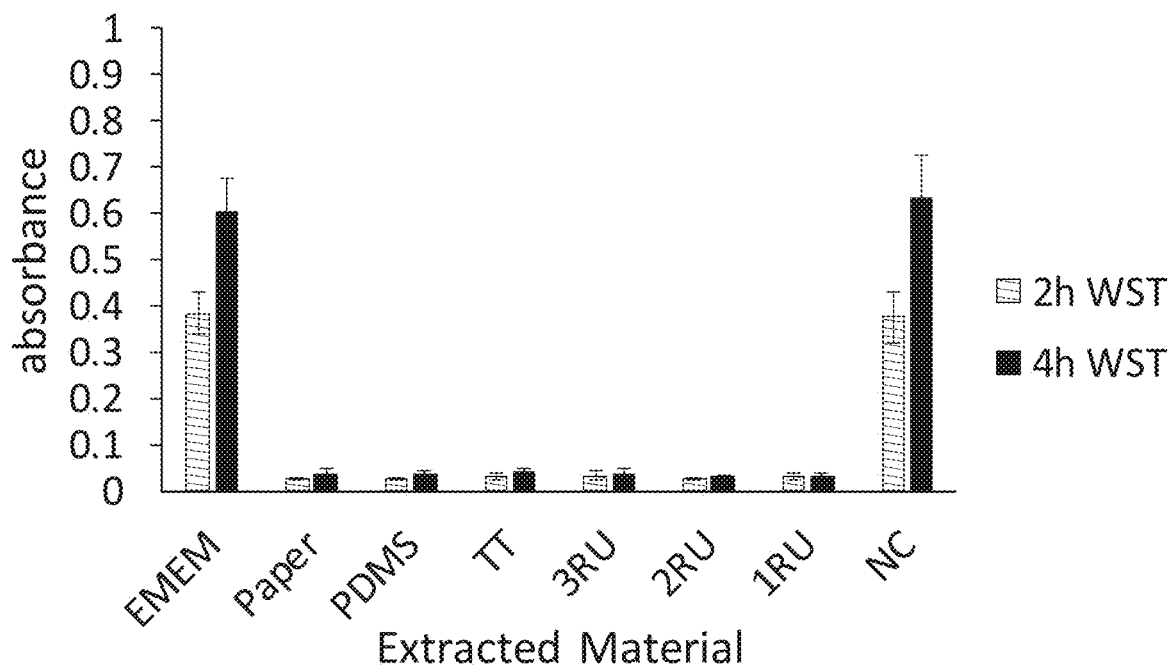
FIG. 30 is a chart showing cytotoxicity test results of smart dressing components, wherein cells were maintained in complete growth medium (Eagle's Minimum Essential Medium) ("EMEM"), polydimethylsiloxane ("PDMS"), double-sided tape ("TT"), RU (ruthenium dye printed on parchment paper as 1, 2 or 3 layers: "1RU," "2RU," and "3RU," respectively), and negative control extract (NC) made from low density polyethylene tubing.
Figure 31:
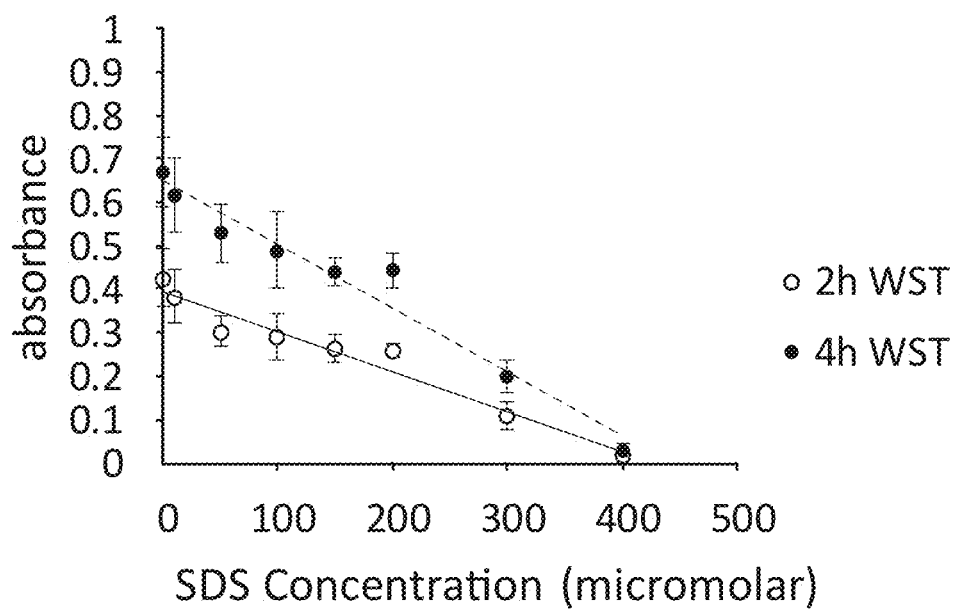
FIG. 31 is a graph showing positive cytotoxicity control for a cytotoxicity assay.
Figure 32:
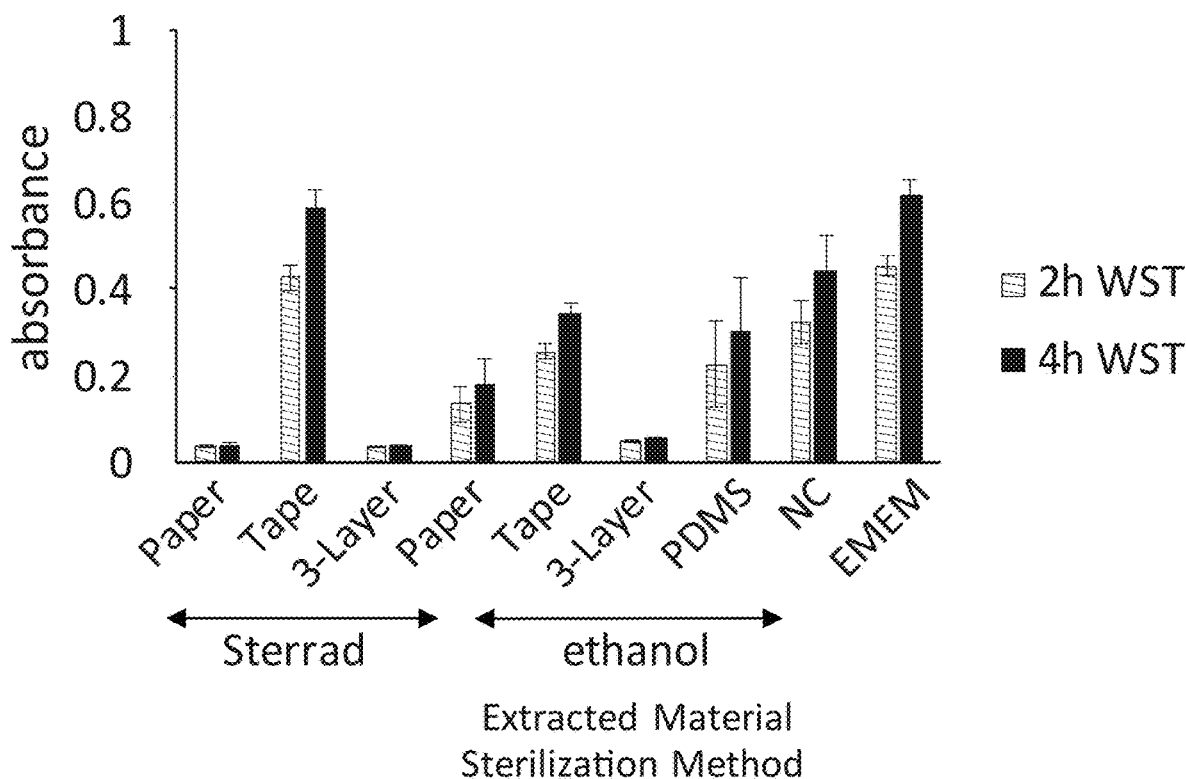
FIG. 32 is a chart showing cytotoxicity of smart dressing components following sterilization by a Sterrad® process or by dipping in 100% ethanol.

The results of the cytotoxicity measurements of the various materials used in the smart dressing are shown in FIGS. 30 and 31. The low metabolic activity of cells treated with the extracts of parchment paper ("Paper"), PDMS, double-sided tape ("TT"), and 3-, 2- or 1-layer ruthenium dye printed on parchment paper ("3RU," "2RU," or "1RU") was significantly less than the activity of cells treated with the LDPE extract (negative control ("NC")) or cells treated with growth medium ("EMEM") and was comparable to cells treated with 300-400 µM SDS (positive controls) (FIG. 31). It is hypothesized that the apparent toxicity of the individual materials could be related to residual contaminants from the Sterrad® process. To test this hypothesis, samples of parchment paper ("Paper"), double-sided tape ("Tape"), PDMS, and the three materials combined ("3-Layer") were sterilized by Sterrad® process (FIG. 32). Duplicate samples were sterilized by dipping in 100% ethanol for 5 minutes and then air-drying before extraction with complete growth medium (37° C./24 h).

Figure 33:
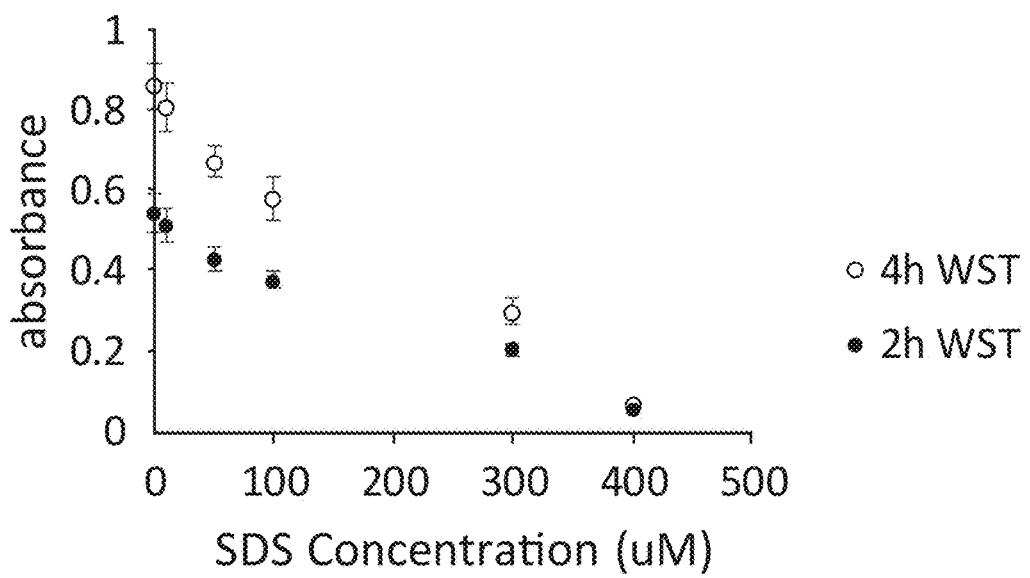
FIG. 33 is a graph showing positive cytotoxicity control for a cytotoxicity assay.

FIG. 32 shows that the cytotoxicity of parchment paper ("Paper"), alone or combined with double-sided tape ("Tape") and PDMS ("3-Layer"), was independent of the sterilization method. However, the effect of the double-sided tape extract on metabolic activity was not significantly different than the negative control ("NC") or Eagle's Minimum Essential Medium ("EMEM") treated samples. This was in contrast to experiment 1, where the extract of double-sided tape induced significant cytotoxicity. This may have been a result of extracting the tape with the backing paper left on in experiment 1 and removing it in experiment 2. Cellulosics are known absorbers of $H_2O_2$ and can be chemically modified by $H_2O_2$. FIG. 33 illustrates the SDS cytotoxicity control for the WST-1 assay.

Figure 34:
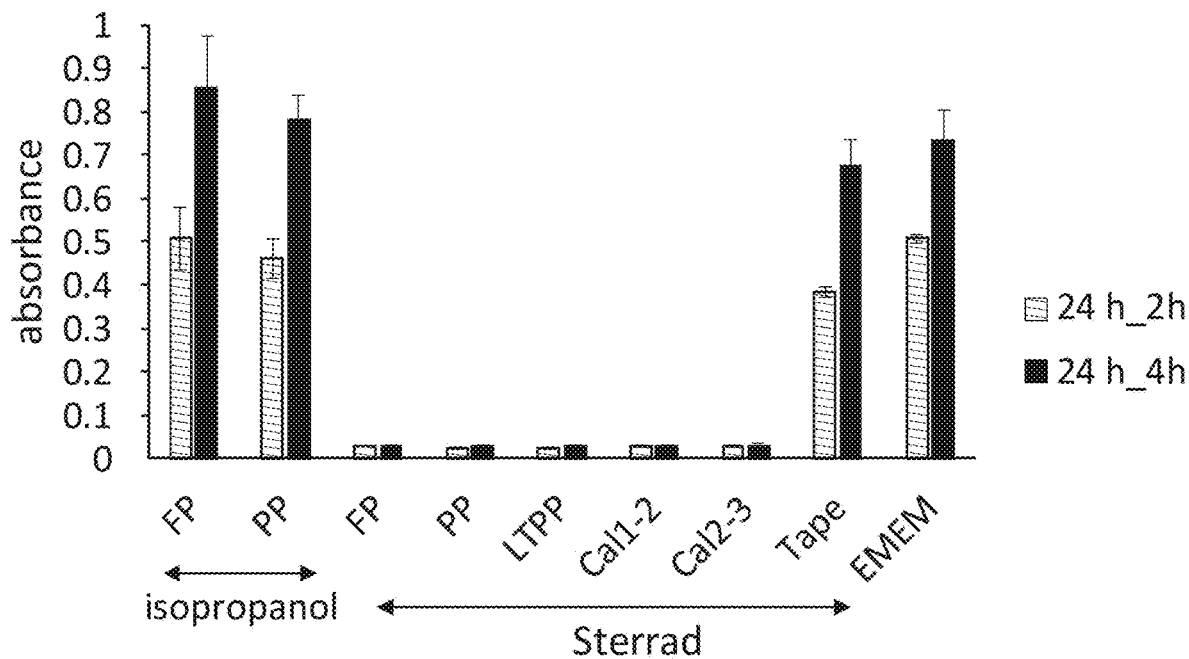
FIG. 34 is a chart showing cytotoxicity of paper sterilized by a Sterrad® process or 70% isopropanol; filter paper ("FP"); parchment paper ("PP"); laser-treated parchment paper ("LTPP"); parchment paper calendered by rollers 1 and 2 ("Cal1-2"); parchment paper calendered by rollers 2 and 3 ("Cal2-3"); positive cytotoxicity control (PC"); negative cytotoxicity control ("NK")
Figure 35:
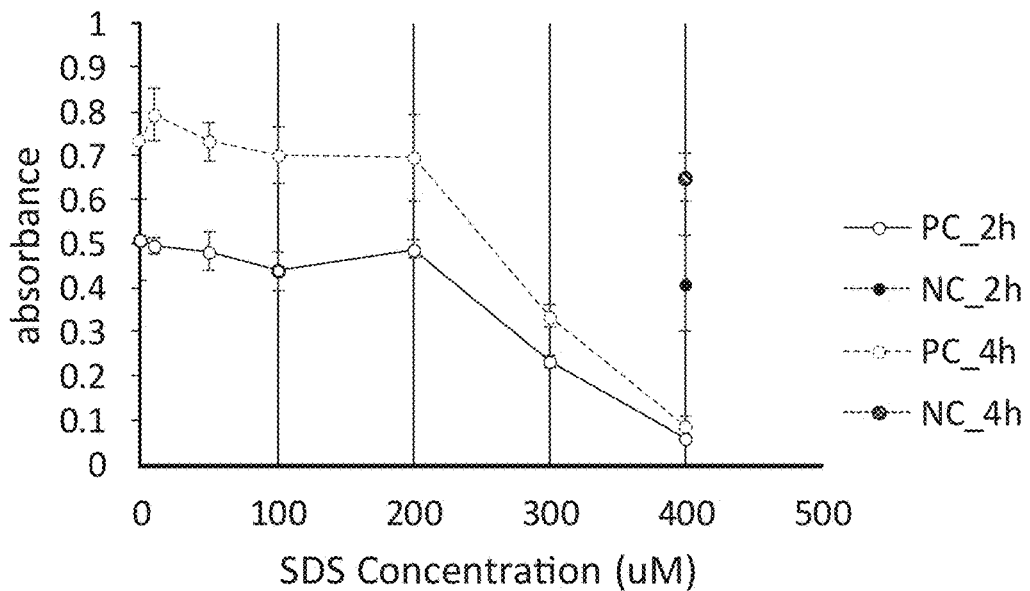
FIG. 35 is a graph showing positive and negative cytotoxicity controls.

To further examine a possible interaction between paper and the Sterrad® process, samples of filter paper and parchment paper were treated with the Sterrad® process or sterilized by immersion in 70% isopropanol. Additional samples of parchment paper calendered between specific rollers were sterilized by the Sterrad® process to determine if the devices could be the source of the toxic contaminants. FIG. 34 shows that extracts of filter paper ("FP"), parchment paper ("PP"), laser-treated parchment paper ("LTPP") and calendered parchment paper ("Cal1-2" and "Cal 2-3") sterilized by the Sterrad® process were significantly cytotoxic and comparable to the cytotoxicity of 400 µM SDS (FIG. 35). By contrast, extracts of filter paper and parchment paper dipped in isopropanol were not cytotoxic and were comparable to cells maintained in EMEM or extracts of double-sided tape without backing. This confirms the previous findings of an interaction between paper and the Sterrad® process, which renders the paper cytotoxic.

Sterilized samples of parchment paper appeared to be cytotoxic due to possible contaminants resulting from the Sterrad® process. The cytotoxicity associated with the Sterrad® process was reduced by washing parchment paper samples for 5 minutes in HBSS followed by equilibration for 5 minutes in complete growth medium.

LIST OF NON-LIMITING EMBODIMENTS

Embodiment A is a fluorescent oxygen sensing ink. The composition of Embodiment A includes an organic solvent, polymer binder in the organic solvent, and fluorescent dye particles disposed in the organic solvent wherein the fluorescent dye particles bind to the alkyl cellulose particles after printing to form a moisture-resistant flexible and conformable film.

The composition of Embodiment A wherein the polymer binder includes alkyl cellulose particles comprising methyl cellulose, ethyl cellulose, propyl cellulose, isopropyl cellulose, n-butyl cellulose, sec-butyl cellulose, pentyl cellulose, or combinations thereof; silicone-based polymers such as polydimethylsiloxane (PDMS), Ecoflex™; or polystyrene.

The composition of Embodiment A or Embodiment A with any of the intervening features wherein the alkyl cellulose particles have a degree of substitution from about 1.0 to about 3.0.

The composition of Embodiment A or Embodiment A with any of the intervening features wherein the organic solvent includes at least one substance or a mixture of substances chosen from the group consisting of ethanol, dimethyl sulfoxide (DMSO), dimethyl-formamide, isopropyl alcohol, acetone, and toluene.

The composition of Embodiment A or Embodiment A with any of the intervening features wherein the fluorescent dye particles comprise a material selected from the group consisting of ruthenium, osmium tetroxide, rhodium acetate, palladium, and chromium.

The composition of Embodiment A or Embodiment A with any of the intervening features wherein the size of particles in the fluorescent oxygen sensing ink should be less than 1/100 of the nozzle diameter to avoid agglomeration and clogging of print nozzles during inkjet printing. For example, if the nozzle diameter is 21 µm, then the particle size should be less than 0.2 µm to avoid agglomeration and clogging of print head nozzles.

The composition of Embodiment A or Embodiment A with any of the intervening features wherein the ink is capable of being printed on hydrophobic to partially hydrophilic substrates, but not completely hydrophilic substrates.

Embodiment B is a method of fabricating an oxygen sensor. The method comprising: providing a liquid ink solution including a solvent, fluorescent ink particles dispersed in the solvent, and a polymer binder dissolved in the solution, wherein the polymer binder particles are bound to the fluorescent ink particles, providing a thin flexible substrate having a surface that is hydrophobic to partially hydrophilic, and printing the liquid ink solution on the surface of the thin flexible substrate.

The method of Embodiment B wherein the polymer binder includes an alkyl cellulose, silicone based polymers such as PDMS, Ecoflex™, or polystyrene.

The method of Embodiment B or Embodiment B with any of the intervening features wherein the alkyl cellulose comprises methyl cellulose, ethyl cellulose, propyl cellulose, isopropyl cellulose, n-butyl cellulose, sec-butyl cellulose, pentyl cellulose, or combinations thereof.

The method of Embodiment B or Embodiment B with any of the intervening features wherein the alkyl cellulose has a degree of substitution from about 1.0 to about 3.0.

The method of Embodiment B or Embodiment B with any of the intervening features wherein the size of particles in the ink system should be less than 1/100 of the nozzle diameter to avoid agglomeration and clogging of print nozzles during inkjet printing. For example, if the nozzle diameter is 21 µm, then the particle size should be less than 0.2 µm to avoid agglomeration and clogging of print head nozzles.

The method of Embodiment B or Embodiment B with any of the intervening features wherein the fluorescent dye complexes comprise a material selected from the group consisting of ruthenium, osmium tetroxide, rhodium acetate, palladium and chromium.

The method of Embodiment B or Embodiment B with any of the intervening features wherein the substrate comprises any paper/coated papers such as parchment, TYVEK®, wax coated, chromatography; any polyester films such as polyethylene terephthalate (PET), polyethylene-naphthalate (PEN); any polyimide films such as KAPTON™, UPILEX™; any polyurethane plastics/thermoplastic elastomers such as thermoplastic polyurethane; any silicon-based organic polymers such as polydimethylsiloxane (PDMS) and ECOFLEX™.

The method of Embodiment B or Embodiment B with any of the intervening features including treating a surface of the substrate, to alter its surface energy, by utilizing a process selected from the group consisting of UV treatment, corona treatment, plasma treatment, sintering, and laser engraving.

The method of Embodiment B or Embodiment B with any of the intervening features wherein the organic solvent includes at least one substance chosen from the group consisting of ethanol, DMSO, dimethyl formamide, isopropyl alcohol, acetone, and toluene.

The method of Embodiment B or Embodiment B with any of the intervening features wherein the ink can be deposited on the substrate using additive print manufacturing processes such as screen, inkjet, flexography, aerosol jet, or gravure.

The method of Embodiment B or Embodiment B with any of the intervening features wherein the organic solvent includes at least one substance or a mixture of substances chosen from the group consisting of ethanol, DMSO, dimethyl formamide, isopropyl alcohol, acetone, and toluene.

The method of Embodiment B or Embodiment B with any of the intervening features wherein the liquid ink solution includes about 75% to about 99% solvent, from about 0.1% to about 5% fluorescent ink particles, and from about 0.1% to about 20% polymer binder particles.

The invention claimed is:

1. A fluorescent oxygen sensing ink suitable for forming a moisture-resistant film for use in liquid environments, comprising:
    at least one organic solvent;
    at least one polymer binder disposed in the at least one organic solvent; and
    an oxygen-sensitive fluorescent dye disposed in the at least one organic solvent;
    wherein the oxygen-sensitive fluorescent dye and the at least one polymer interact to form a moisture-resistant film for use in liquid environments and that emits light within the visible light range in response to excitation light within the visible light range to measure dissolved oxygen levels in liquid.

2. The fluorescent oxygen sensing ink of claim 1, wherein: the at least one polymer binder comprises polystyrene, silicone-based polymers, alkyl cellulose materials, and combinations thereof.

3. The fluorescent oxygen sensing ink of claim 2, wherein: the at least one polymer binder is an alkyl cellulose material selected from the group comprising methyl cellulose, ethyl cellulose, propyl cellulose, isopropyl cellulose, n-butyl cellulose, sec-butyl cellulose, pentyl cellulose, and combinations thereof.

4. The fluorescent oxygen sensing ink of claim 2, wherein: the at least one polymer binder comprises an alkyl cellulose material that does not contain any sulphonic or phosphonic groups.

5. The fluorescent oxygen sensing ink of claim 1, wherein: the at least one organic solvent is selected from the group consisting of ethanol, dimethyl sulfoxide (DMSO), dimethyl formamide, isopropyl alcohol, acetone, toluene, and combinations thereof.

6. The fluorescent oxygen sensing ink of claim 1, wherein: the oxygen-sensitive fluorescent dye comprises a material selected from the group consisting of ruthenium, osmium tetroxide, rhodium acetate, palladium, and chromium.

7. The fluorescent oxygen sensing ink of claim 1, wherein: the at least one polymer binder and the fluorescent dye each have a particle size of less than 0.2 μm.

8. The fluorescent oxygen sensing ink of claim 1, wherein: the at least one organic solvent is present in an amount of about 75 wt % to about 99 wt %, the at least one polymer binder is present in an amount of from about 0.1 wt % to about 20 wt %, and the oxygen-sensitive fluorescent dye is present in an amount of from about 0.1 wt % to about 5 wt %.

9. An oxygen sensing wound dressing, comprising:
    a substrate;
    at least one fluid channel bonded to the substrate; and
    an oxygen sensing ink printed on the substrate;
    wherein the oxygen sensing ink comprises:
        at least one organic solvent;
        at least one polymer binder; and
        an oxygen-sensitive dye capable of fluorescing in the presence of oxygen.

10. The oxygen sensing wound dressing of claim 9, wherein:
    the substrate comprises rastered or unrastered materials selected from the group comprising: paper, coated paper, parchment paper, wax coated paper, chromatography paper, polyester films, polyethylene terephthalate (PET), polyethylene-naphthalate (PEN), polyimide films, polyurethane materials, silicone-based polymers, polydimethylsiloxane (PDMS), and Tyvek®.

11. The oxygen sensing wound dressing of claim 9, wherein:
    the at least one fluid channel is formed from polydimethylsiloxane (PDMS).

12. The oxygen sensing wound dressing of claim 9, wherein:
    the oxygen sensing ink forms a moisture-resistant film on the substrate.

13. The oxygen sensing wound dressing of claim 9, wherein:
    the at least one polymer binder comprises polystyrene, silicone-based polymers, alkyl cellulose materials, and combinations thereof.

14. The oxygen sensing wound dressing of claim 9, wherein:
    a surface energy of the substrate is higher than a surface tension of the oxygen sensing ink.

15. The oxygen sensing wound dressing of claim 9, wherein:
    the oxygen-sensitive dye comprises a material selected from the group consisting of ruthenium, osmium tetroxide, rhodium acetate, palladium, and chromium.

16. A method of fabricating an oxygen sensor for use in liquid environments, the method comprising:
providing a substrate;
providing an oxygen sensing ink, comprising:
- at least one organic solvent;
- at least one polymer binder; and
- an oxygen-sensitive fluorescent dye that emits light within the visible light range in response to excitation light within the visible light range; and printing the oxygen sensing ink on a surface of the substrate to form a moisture-resistant film that is suitable for use in liquid environments to measure dissolved oxygen concentration of liquids.

17. The method of claim 16, wherein:
the at least one polymer binder comprises alkyl cellulose that does not contain any sulphonic or phosphonic groups.

18. The method of claim 16, wherein:
substrate comprises parchment paper; and including:
prior to printing the oxygen sensing ink, treating the parchment paper utilizing a laser rastering process to increase the surface energy of the parchment paper.

19. A method of fabricating an oxygen sensor, the method comprising:
providing a substrate;
providing an oxygen sensing ink, comprising:
- at least one organic solvent;
- at least one polymer binder; and
- an oxygen-sensitive fluorescent dye;

printing the oxygen sensing ink on a surface of the substrate; and
treating the surface of the substrate, to alter a surface energy of the surface, by at least one of a UV treatment, a corona treatment, a plasma treatment, sintering, or laser engraving.

20. The method of claim 16, wherein the step of printing the oxygen sensing ink on a surface of the substrate further comprises:
depositing the oxygen sensing ink on the surface by screen printing, inkjet printing, flexography, aerosol jet printing, or gravure printing.

21. A fluorescent oxygen sensing ink, comprising:
at least one organic solvent;
an ethyl cellulose binder disposed in the at least one organic solvent, wherein the ethyl cellulose binder does not contain any sulphonic or phosphonic groups; and
an oxygen-sensitive fluorescent dye disposed in the at least one organic solvent;
wherein the oxygen-sensitive fluorescent dye and the ethyl cellulose binder interact to form a moisture-resistant film that emits light in response to excitation light to measure dissolved oxygen concentration of liquids.

22. The fluorescent oxygen sensing ink of claim 21, wherein:
the moisture-resistant film emits light within the visible light range in response to excitation light within the visible range.

* * * * *

UNITED STATES PATENT AND TRADEMARK OFFICE
CERTIFICATE OF CORRECTION

| | |
|---|---|
| PATENT NO. | : 11,525,063 B2 |
| APPLICATION NO. | : 16/288819 |
| DATED | : December 13, 2022 |
| INVENTOR(S) | : Atashbar et al. |

It is certified that error appears in the above-identified patent and that said Letters Patent is hereby corrected as shown below:

In the Claims

Column 31, Line 19, Claim 18:
Before "substrate" insert --the--.

Signed and Sealed this
Twenty-fifth Day of April, 2023

*Katherine Kelly Vidal*

Katherine Kelly Vidal
*Director of the United States Patent and Trademark Office*